(12) United States Patent
Becker et al.

(10) Patent No.: US 12,329,759 B2
(45) Date of Patent: Jun. 17, 2025

(54) METHODS AND COMPOSITIONS RELATING TO LUNG FUNCTION

(71) Applicant: TRUSTEES OF BOSTON UNIVERSITY, Boston, MA (US)

(72) Inventors: Elizabeth Jeanne Becker, Cambridge, MA (US); Katrina Steiling, Boston, MA (US); Avrum E. Spira, Newton, MA (US); Marc E. Lenburg, Brookline, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 17/071,228

(22) Filed: Oct. 15, 2020

(65) Prior Publication Data

US 2021/0113581 A1  Apr. 22, 2021

Related U.S. Application Data

(60) Provisional application No. 62/916,431, filed on Oct. 17, 2019.

(51) Int. Cl.
| | | |
|---|---|---|
| *A61P 11/08* | (2006.01) | |
| *A61K 9/00* | (2006.01) | |
| *A61K 31/122* | (2006.01) | |
| *A61K 31/135* | (2006.01) | |
| *A61K 31/357* | (2006.01) | |
| *A61K 31/439* | (2006.01) | |
| *A61K 31/55* | (2006.01) | |

(52) U.S. Cl.
CPC ............ *A61K 31/55* (2013.01); *A61K 9/0073* (2013.01); *A61K 31/122* (2013.01); *A61K 31/135* (2013.01); *A61K 31/357* (2013.01); *A61K 31/439* (2013.01); *A61P 11/08* (2018.01)

(58) Field of Classification Search
CPC .... A61K 31/55; A61K 31/135; A61K 31/357; A61K 31/439; A61P 11/08
See application file for complete search history.

(56) References Cited

U.S. PATENT DOCUMENTS

| | | | |
|---|---|---|---|
| 4,767,753 A | 8/1988 | Pickart | |
| 7,632,803 B2 | 12/2009 | Bar-Or | |
| 9,585,930 B2 * | 3/2017 | Spira | G01N 33/6884 |
| 2009/0061454 A1 | 3/2009 | Brody et al. | |
| 2010/0048693 A1 | 2/2010 | Geraci et al. | |
| 2010/0119474 A1 * | 5/2010 | Crystal | C12Q 1/6883 424/85.2 |
| 2017/0112763 A1 | 4/2017 | Gerhart | |
| 2019/0292600 A1 | 9/2019 | Spira et al. | |
| 2019/0382745 A1 * | 12/2019 | Moss | A61K 38/4886 |

FOREIGN PATENT DOCUMENTS

| | | |
|---|---|---|
| EP | 0450991 A2 | 10/1991 |
| EP | 1014993 B1 | 8/2002 |
| EP | 1611898 A1 | 1/2006 |
| RU | 2214269 C1 | 10/2003 |
| WO | 1996039144 A1 | 12/1996 |
| WO | 2003068187 A1 | 8/2003 |
| WO | 2005047451 A2 | 5/2005 |
| WO | 2007035843 A2 | 3/2007 |
| WO | 2010028247 A2 | 3/2010 |
| WO | 2012129237 A2 | 9/2012 |
| WO | 2013177060 A2 | 11/2013 |
| WO | 2019152629 A1 | 8/2019 |

OTHER PUBLICATIONS

Hoshino et al. ("Effects of tiotropium and salmeterol/fluticasone propionate on airway wall thickness in chronic obstructive pulmonary disease." Respiration (2013);86(4):280-7). (Year: 2013).*
Wang et al. ("Genes associated with MUC5AC expression in small airway epithelium of human smokers and non-smokers." BMC Med Genomics. 2012; 5: 21.) (Year: 2012).*
Steiling et al. (Proc Am Thorac Soc (2009);6:697-700). (Year: 2009).*
Singh et al. "Superiority of "triple" therapy with salmeterol/fluticasone propionate and tiotropium bromide versus individual components in moderate to severe COPD." Thorax 2008;63:592-598. doi: 10.1136/thx.2007.08721.) (Year: 2007).*
Wang et al. (Am J Respir Crit Care Med vol. 198, Iss 12, pp. 1500-1518, Dec. 15, 2018). (Year: 2018).*
Anonymous, "Emphysema Guide: causes, symptoms and treatment options." http://www.drugs.com/health-guide/emphysema.html Dec. 23, 2010.
Arul et al., Life. Sci. 80(4):275-284 (2007). "A therapeutic approach for diabetic wound healing using biotinylated HK Incorporated collagen matrices."
Becker et al. "A Bronchial Airway Gene Expression Signature of Future Lung Function Decline Is Enriched in XBP1 Activity." D107. Mitochondria and ER Stress in Homeostasis and Repair. American Thoracic Society: A7234-A7234 (2019).
Becker et al. "A Bronchial Airway Gene Expression Signature of Lung Function Decline." D18. Who Does What in COPD: the Cellular Origins. American Thoracic Society: A7036-A7036 (2017).
Becker et al. "Derivation of a Bronchial Airway Gene Expression Signature Associated with FEV1 Decline." D53. Off the Beaten Path: New Approaches to COPD Pathogenesis. American Thoracic Society: A7159-A7159 (2018).
Becker et al. "Predicting Lung Function Decline in COPD Using Bronchial Airway Gene Expression." Chest 150(4): 912A (2016).
Bhattacharya et al., Am J Respir Cell Mol Biol. 40(3):359-67 (2009). "Molecular biomarkers for quantitative and discrete COPD phenotypes."

(Continued)

*Primary Examiner* — Amanda L. Aguirre
*Assistant Examiner* — Chris E Simmons
(74) *Attorney, Agent, or Firm* — Nixon Peabody LLP; Ronald I. Eisenstein; Nicole D. Kling

(57) ABSTRACT

The technology described herein is directed to methods and compositions for prognosis and treatment of respiratory disease, e.g., COPD.

29 Claims, 8 Drawing Sheets

(56) References Cited

OTHER PUBLICATIONS

Boudewijn et al. "Nasal gene expression differentiates COPD from controls and overlaps bronchial gene expression." Respiratory Research 18(1): 213 pp. 1-10 (2017).
Chung et al. "Cytokines in chronic obstructive pulmonary disease." European Respiratory Journal 18(34 Suppl): 50s-59s (2001).
Dekhuijzen et al., Eur Respir J. 23(4):629-36 (2004). "Antioxidant properties of N-acetylcysteine: their relevance in relation to chronic obstructive pulmonary disease."
Demeo et al., "α1-Antitrypsin deficiency. 2: Genetic aspects of a1-antitrypsin deficiency: phenotypes and genetic modifiers of emphysema risk." Thorax 59(3):259-264 (2004).
Demoor et al., Eur Respir J. 34(2):405-16 (2009). "Role of lymphotoxin-alpha in cigarette smoke-induced inflammation and lymphoid neogenesis."
Gauldie et al., Proc Am Thorac Soc. 3(8):696-702 (2006). "Smad3 signaling involved in pulmonary fibrosis and emphysema."
Golpon et al., Am J Respir Cell Mol Biol. 31(6):595-600 (2004). "Emphysema lung tissue gene expression profiling."
Geraghty et al. "Glutathione peroxidase-1 suppresses the unfolded protein response upon cigarette smoke exposure." Mediators of inflammation 2016: 9461289 pp. 1-16 (2016).
Gray et al.,Am J Respir Crit Care Med. 178(5):444-52 (2008). "Sputum proteomics in inflammatory and suppurative respiratory diseases."
Gregor et al. "The role of adipocyte XBP1 in metabolic regulation during lactation." Cell Reports 3(5): 1430-1439 (2013).
Jorgensen et al. "Cigarette smoke induces endoplasmic reticulum stress and the unfolded protein response in normal and malignant human lung cells." BMC Cancer 8(1): 229 pp. 1-30 (2008).
Kelsen. "The unfolded protein response in chronic obstructive pulmonary disease." Annals of the American Thoracic Society 13(Supplement 2): S138-S145 (2016).
Konigshoff et al., Swiss Med Wkly. 139(39-40):554-563 (2009). "TGF-beta signaling in COPD: deciphering genetic and cellular susceptibilities for future therapeutic regimen."
Lamson et al., Altern Med Rev. 5(5):429-31 (2000). "The use of nebulized glutathione in the treatment of emphysema: a case report."
Lau et al., "The intersection of copper(II) and glycyl=L-histidyl-L-lysine, a growth-modulating tripeptide from plasma." Biochem J. 199:649-656 (1981).
Liu et al. "Hepatocyte X-box binding protein 1 deficiency increases liver injury in mice fed a high-fat/sugar diet." American Journal of Physiology-Gastrointestinal and Liver Physiology 309(12): G965-G974 (2015).
Marquart et al., J Clin Invest. 92(5):2368-76 (1993). "In vivo stimulation of connective tissue accumulation by the tripeptide-copper complex glycyl-L-histidyl-L-lysine-Cu2+ in rat experimental wounds."
Mimura et al. "Blockade of XBP1 splicing by inhibition of IRE1a is a promising therapeutic option in multiple myeloma." Blood, The Journal of the American Society of Hematology 119(24): 5772-5781 (2012).
Min et al. "Critical role of proteostasis-imbalance in pathogenesis of COPD and severe emphysema." Journal of Molecular Medicine 89(6): 577-593 (2011).
Ning et al., Proc Natl Acad Sci U S A. 101(41):14895-14900 (2004). "Comprehensive gene expression profiles reveal pathways related to the pathogenesis of chronic obstructive pulmonary disease."
Overley-Adamson et al. "Targeting the unfolded protein response, XBP1, and the NLRP3 inflammasome in fibrosis and cancer." Cancer Biology & Therapy 15(4): 452-462 (2014).
Pickart et al., 19(8):969-88 (2008). J Biomater Sci Polym Ed. "The human tri-peptide GHK and tissue remodeling."
Pons et al., Eur Respir J. 26(1):60-6 (2005). "Decreased macrophage release of TGF-beta and TIMP-1 in chronic obstructive pulmonary disease."
Roberts et al., Nature 422(6928):130-1 (2003). "Medicine: Smoke signals for lung disease."
Simeon et al., J Invest Dermatol. 115(6):962-8. "Expression of glycosaminoglycans and small proteoglycans in wounds: modulation by the tripeptide-copper complex glycyl-L-histidyl-L-lysine-Cu2+."
Soskel et al., "Mechanisms of lung injury in the copper-deficient hamster model of emphysema." Chest 85 (Supplemen):70S-73S (1984).
Spira et al., Am J Respir Cell Mol Biol. 31(6):601-10 (2004). "Gene expression profiling of human lung tissue from smokers with severe emphysema."
Springer et al., Biol Chem. 385(7):649-53. (2004). "SMAD-signaling in chronic obstructive pulmonary disease: transcriptional down-regulation of inhibitory SMAD 6 and 7 by cigarette smoke."
Steiling et al. "A dynamic bronchial airway gene expression signature of chronic obstructive pulmonary disease and lung function impairment." American Journal of Respiratory and Critical Care Medicine 187(9): 933-942 (2013).
Vassallo et al., Respir Res. 11:45-58 (2010). "Cigarette smoke promotes dendritic cell accumulation in COPD; a Lung Tissue Research Consortium study."
Wang et al., Am J Respir Crit Care Med. 177(4):402-11 (2008). "Gene expression profiling in patients with chronic obstructive pulmonary disease and lung cancer."
Zandvoort et al., Eur Respir J. 28(3):533-41 (2006). "Altered expression of the Smad signalling pathway: implications for COPD pathogenesis."

* cited by examiner

METHODS AND COMPOSITIONS RELATING TO LUNG FUNCTION

CROSS-REFERENCE TO RELATED APPLICATIONS

This application claims benefit under 35 U.S.C. § 119(e) of U.S. Provisional Application No. 62/916,431 filed Oct. 17, 2019, the contents of which are incorporated herein by reference in their entirety.

GOVERNMENT SUPPORT

This invention was made with government support under Grant Nos. HL095388, HL118542-0, RR025770, and CA164783 awarded by the National Institutes of Health. The government has certain rights in the invention.

TECHNICAL FIELD

The technology described herein relates to methods of treating COPD.

BACKGROUND

Chronic Obstructive Pulmonary Disease (COPD) is the third leading cause of death in the world. Patients with COPD experience lung function decline over time, most commonly measured by change in the forced expiratory volume in one second ($FEV_1$). Lower FEV1 is associated with an increased risk of death, and even smokers who do not yet meet the clinical definition of COPD may experience more rapid FEV1 decline. The rate of FEV1 decline is highly variable between individuals. Though some risk factors for rapid FEV1 decline have been identified, such as cigarette smoking, higher blood neutrophil counts, albuminuria, and Alpha 1-antitrypsin deficiency, these do not fully explain the heterogeneity in COPD, and have not yet been useful in predicting FEV1 decline for individual patients. The ability to predict $FEV_1$ decline would permit clinicians to stratify at-risk patients towards more aggressive management. It can also facilitate clinical trials of therapies to modify the natural history of COPD, specifically targeting individuals more likely to experience greater decline in FEV1. Finally, it can lead to further indications for finding therapeutic targets to slow disease progression.

SUMMARY

As described herein, the inventors have identified a bronchial airway gene expression profile that is associated with the rate of subsequent lung function decline. This diagnostic assessment identifies individuals with incipient COPD prior to the loss of substantial lung function, permitting a window of opportunity so that early therapy can effectively lead to COPD interception.

In one aspect of any of the embodiments, described herein is a method of treating a respiratory disease, e.g., chronic obstructive pulmonary disease (COPD), the method comprising: a) administering one or more of an inhaled long acting antimuscarinic, an inhaled long-acting β2 agonist, and an inhaled corticosteroid to a subject determined to have an increased level of expression of one or more genes of Table 11 and/or a decreased level of expression of one or more genes of Table 12; and b) administering one or more of intensive smoking cessation therapy and an inhaled short-acting β2 agonist to a subject determined not to have an increased level of expression of one or more genes of Table 11 and/or a decreased level of expression of one or more genes of Table 12.

In one aspect of any of the embodiments, described herein is a method of determining if a subject has a high or increased rate of FEV1, is at risk of a high or increased rate of FEV1, or is in need of treatment for a high or increased rate of FEV1, the method comprising: determining the level of expression of one or more genes of Tables 11 and/or 12 in a sample obtained from the subject, wherein increased levels of expression of one or more genes of Table 11 and/or decreased levels of expression of one or more genes of Table 12 relative to a reference indicates the subject has a high or increased rate of FEV1, is at risk of a high or increased rate of FEV1, or is in need of treatment for a high or increased rate of FEV1. In one aspect of any of the embodiments, described herein is a non-invase method of identifying a subject at risk for a respiratory disease (e.g., COPD) comprising: determining the level of expression of one or more genes of Tables 11 and/or 12 in a sample obtained from the subject, wherein increased levels of expression of one or more genes of Table 11 and/or decreased levels of expression of one or more genes of Table 12 relative to a reference indicates the subject is at risk for the respiratory disease. In one aspect of any of the embodiments, described herein is a composition or combination comprising an inhaled long acting antimuscarinic, an inhaled long-acting β2 agonist, an inhaled corticosteroid, an inhibitor of at least one gene of Table 11, and/or an agonist of at least one gene of Table 12 for use in a method of treating a respiratory disease in a subject in need thereof, wherein the subject is one determined to have an increased level of expression of one or more genes of Table 11 and/or a decreased level of expression of one or more genes of Table 12.

In one aspect of any of the embodiments, described herein is a method comprising determining the level of expression of one or more genes of Table 11 and/or Table 12 in a sample obtained from a subject, wherein the sample is a bronchial brushing, bronchial biopsy, bronchial epithelium sample, airway epithelium sample, nasal brushing, and/or nasal epithelium sample.

In some embodiments of any of the aspects, the respiratory disease is COPD.

In some embodiments of any of the aspects, the one or more genes of Table 11 and/or at least one or more genes of Table 12 comprise at least one of GALE; SEC61A1; KDELR2; EIF2AK3; S100A16; ADAM9; TMED3; MIA3; SURF4; and TXNDC11. In some embodiments of any of the aspects, the one or more genes of Table 11 and/or at least one or more genes of Table 12 comprise GALE; SEC61A1; KDELR2; EIF2AK3; S100A16; ADAM9; TMED3; MIA3; SURF4; and TXNDC11. In some embodiments of any of the aspects, the one or more genes of Table 11 and/or at least one or more genes of Table 12 comprise EIF2AK3; S100A16; ADAM9; TMED3; MIA3; SURF4; and TXNDC11. In some embodiments of any of the aspects, the one or more genes of Table 11 and/or at least one or more genes of Table 12 comprise EIF2AK3; S100A16; ADAM9; MIA3; SURF4; and TXNDC11. In some embodiments of any of the aspects, the level of expression of one or more of NSUN7; LOC100128816; MTHFD2; KDELR2; SLC44A3; SLC16A9; TMED3; TSPAN13; SEC61A1; and FAM177B are not determined. In some embodiments of any of the aspects, the level of expression of one or both of ENO4 and CREB3L1 are not determined.

In some embodiments of any of the aspects, the expression of no more than 400 genes is determined. In some embodiments of any of the aspects, the expression of no more than 200 genes is determined. In some embodiments of any of the aspects, the expression of no more than 100 genes is determined.

In some embodiments of any of the aspects, an increased or decreased level is the level relative to a patient who has never been a smoker. In some embodiments of any of the aspects, an increased or decreased level is the level relative to an age-matched patient who has never been a smoker.

In some embodiments of any of the aspects, the level is the level in a bronchial brushing, bronchial biopsy, bronchial epithelium, airway epithelium, nasal brushing, and/or nasal epithelium. In some embodiments of any of the aspects, the level is the level in the nasal epithelium.

In some embodiments of any of the aspects, the subject is a current or former tobacco smoker. In some embodiments of any of the aspects, the subject has been exposed to asbestos, air pollution, or environmental hazards. In some embodiments of any of the aspects, the environmental hazard is dust, chemicals, fire, or smoke.

In some embodiments of any of the aspects, the subject has or is diagnosed as having COPD.

In some embodiments of any of the aspects, the subject is a mammal. In some embodiments of any of the aspects, the subject is a human. In some embodiments of any of the aspects, the human subject is at least 49 years old. In some embodiments of any of the aspects, the human subject is at least 58 years old. In some embodiments of any of the aspects, the subject has a GOLD grade of 2 or lower.

In some embodiments of any of the aspects, the inhaled long-acting antimuscarinic is selected from the group consisting of: tiotropium; ipratropium; umiclinidium; aclidinium; and diphenhydramine. In some embodiments of any of the aspects, the inhaled long-acting agonist is selected from the group consisting of: fomoterol; salmeterol; arformoterol; bambuterol; clenbuterol abediterol; carmoterol; olodaterol; indacaterol; and vlianterol. In some embodiments of any of the aspects, the inhaled corticosteroid is selected from the group consisting of: budesonide; fluticasone; flunisolide; triamcinolone acetonide; beclomethasone dipropionate; mometasone furoate; and ciclesonide. In some embodiments of any of the aspects, the inhaled short-acting β2 agonist is selected from the group consisting of: albuterol; bitolterol; fenoterol; isoprenaline; isoproterenol; levosalbutamol; levalbuterol; orciprenaline; metaproterenol; pirbuterol; procaterol; ritodrine; salbutamol; and terbutaline. In some embodiments of any of the aspects, the treatment administered to a subject determined to have an increased level of expression of one or more genes of Table 11 and/or a decreased level of expression of one or more genes of Table 12 further comprises administration of an inhibitor of one or more genes of Table 11 and/or an agonist of one or more genes of Table 12.

In one aspect of any of the embodiments, described herein is a method of treating a respiratory disease (e.g., COPD) comprising administering an inhibitor of one or more genes of Table 11 and/or an agonist of one or more genes of Table 12. In some embodiments of any of the aspects, the subject is determined to have an increased level of expression of one or more genes of Table 11 and/or a decreased level of expression of one or more genes of Table 12. In some embodiments of any of the aspects, the administering step comprises the administration of a vector comprising a nucleic acid encoding the agonist and/or inhibitor.

BRIEF DESCRIPTION OF THE DRAWINGS

(FIG. 3A) Genes that increase in individuals with more rapid FEV1 decline are significantly enriched among the genes that are most induced by XBP1 overexpression in murine adipocytes (GSEA p<0.001). The vertical lines are the position of the genes with increased expression in individuals with more rapid FEV1 decline in a list of all genes ranked from most induced by XBP1 overexpression to most repressed. The height of the vertical line represents the running enrichment score, and the lines highlighted in red represent the leading edge. (FIG. 3B) Heatmap of the expression of the leading edge genes in the discovery set. Samples are ordered by rate of $FEV_1$ decline. (FIG. 3C) Heatmap of the expression of the leading edge genes in the XBP1 overexpression dataset. The genes are in the same order as in FIG. 3B.

(FIG. 4A) Genes that increase in individuals with more rapid FEV1 decline are significantly enriched among the genes that are most repressed in murine hepatocytes deleted for XBP1 (GSEA p=0.025). (FIG. 4B) Heatmap of the expression of the leading edge genes in the discovery set. (FIG. 4C) Heatmap of the expression of the leading edge genes in the XBP1 deletion dataset. The genes are in the same order as in FIG. 4B.

FIG. 6A: An example gene from only the participants who were current smokers, TCN1. FIG. 6B: An example gene from only the participants who were former smokers, GALNT4. FIG. 6C: An example gene from only the participants who were not on inhaled corticosteroids, GALNT12.

DETAILED DESCRIPTION

Figure 1:
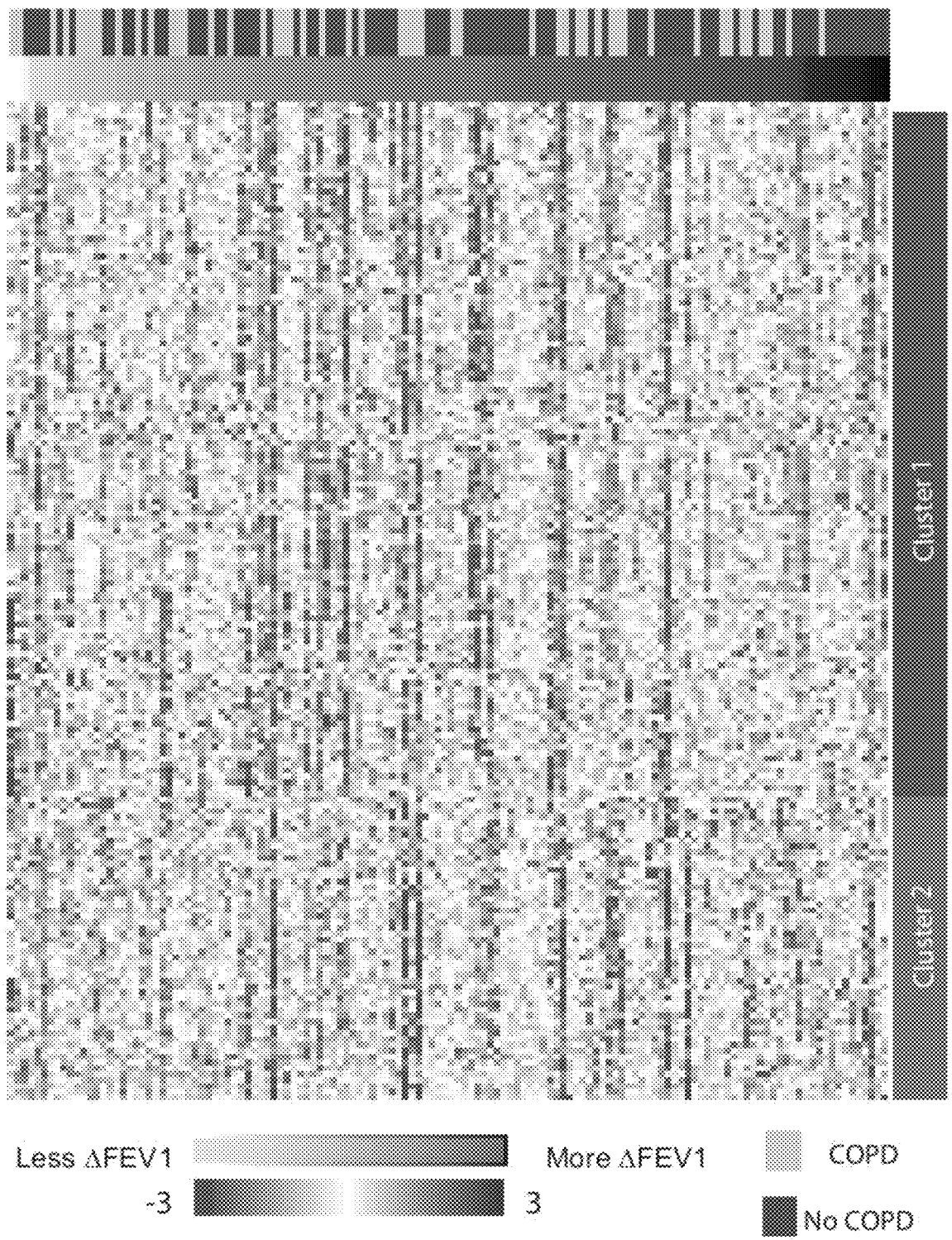
FIG. 1 depicts a heatmap of 171 Genes Associated with Change in $FEV_1$. One hundred and seventy one genes were associated with the change in the rate of $FEV_1$ decline using a linear model controlling for age, sex, smoking status, pack years, and baseline $FEV_1$ (FDR<0.05). The patients (columns) are arranged from least $FEV_1$ decline (white) to most $FEV_1$ decline (black). These genes were grouped into two clusters based on unsupervised hierarchical clustering, which corresponds in this case to the direction the genes were altered in advance of $FEV_1$ decline. Cluster 1 are genes that increase with greater $FEV_1$ decline and cluster 2 are genes that decrease with greater $FEV_1$ decline.

The inventors have found that subjects who will suffer particularly high rates of FEV1 decline are those with increased levels of expression of one or more genes of Table 11 and/or decreased levels of expression of one or more genes of Table 12. Conversely, subjects who will not suffer particularly high rates of FEV1 decline are those who do not have increased levels of expression of one or more genes of Table 11 and/or decreased levels of expression of one or more genes of Table 12. This advancement has also provided a number of novel and improved therapeutic and prognostic methods as described herein.

In one aspect of any of the embodiments, described herein is a method of treating a respiratory disease, e.g., treating chronic obstructive pulmonary disease (COPD), the method comprising a) administering one or more of an inhaled long acting antimuscarinic, an inhaled long-acting β2 agonist, and an inhaled corticosteroid to a subject determined to have an increased level of expression of one or more genes of Table 11 and/or a decreased level of expression of one or more genes of Table 12; and b) administering one or more of intensive smoking cessation therapy and an inhaled short-acting β2 agonist to a subject determined not to have an increased level of expression of one or more genes of Table 11 and/or a decreased level of expression of one or more genes of Table 12. In some embodiments of any of the aspects described herein, the respiratory disease is asthma and methods described for the treatment of COPD can be applied instead to the treatment of asthma.

In some embodiments of any of the aspects, the treatment of COPD is prophylactic, e.g., the subject does not yet meet the criteria for a COPD diagnosis. In such cases, the methods can be methods of treating respiratory disease. The terms "respiratory disorder" and "respiratory disease" are used interchangeably herein and refer to any condition and/or disorder relating to respiration and/or the respiratory system. The respiratory disorder can be allergic or non-allergic. In some embodiments, the respiratory disorder is selected from the group consisting of asthma, atopic asthma, non-atopic asthma, emphysema, bronchitis, chronic obstructive pulmonary disease (COPD), sinusitis, allergic rhinitis. In some embodiments, the respiratory disorder is characterized by increased responsiveness of the tracheas and bronchi to various stimuli, i.e., allergens, resulting in a widespread narrowing of the airways. The term "COPD" is generally applied to chronic respiratory disease processes characterized by the persistent obstruction of bronchial air flow. COPD patients can suffer from conditions such as bronchitis, cystic fibrosis, asthma or emphysema.

In some embodiments of any of the aspects, the method comprises administering one or more of an inhaled long acting antimuscarinic, an inhaled long-acting β2 agonist, and an inhaled corticosteroid to a subject previously determined to have increased levels of expression of one or more genes of Table 11 and/or decreased levels of expression of one or more genes of Table 12 relative to a reference; and/or administering one or more of intensive smoking cessation therapy and an inhaled short-acting β2 agonist to a subject previously determined not to have an increased level of expression of one or more genes of Table 11 and/or a decreased level of expression of one or more genes of Table 12 relative to a reference.

In some embodiments of any of the aspects, described herein is a method of treating COPD in a subject in need thereof, the method comprising: a) first determining the level of expression of one or more genes of Table 11 and/or Table 12 in a sample obtained from a subject; and b) then administering one or more of an inhaled long acting antimuscarinic, an inhaled long-acting β2 agonist, and an inhaled corticosteroid to the subject if it is determined they have increased levels of expression of one or more genes of Table 11 and/or decreased levels of expression of one or more genes of Table 12 relative to a reference; and/or administering one or more of intensive smoking cessation therapy and an inhaled short-acting β2 agonist to the subject if it is determined they do not have an increased level of expression of one or more genes of Table 11 and/or a decreased level of expression of one or more genes of Table 12 relative to a reference.

In one aspect of any of the embodiments, described herein is a method of treating COPD in a subject in need thereof, the method comprising: a) determining if the subject has increased levels of expression of one or more genes of Table 11 and/or decreased levels of expression of one or more genes of Table 12; and b) instructing or directing that the subject be administered one or more of an inhaled long acting antimuscarinic, an inhaled long-acting β2 agonist, and an inhaled corticosteroid to the subject if it is determined they have increased levels of expression of one or more genes of Table 11 and/or decreased levels of expression of one or more genes of Table 12 relative to a reference; and/or administered one or more of intensive smoking cessation therapy and an inhaled short-acting β2 agonist to the subject if it is determined they do not have an increased level of expression of one or more genes of Table 11 and/or a decreased level of expression of one or more genes of Table 12 relative to a reference.

In some embodiments of any of the aspects, the step of determining if the subject has increased levels of expression of one or more genes of Table 11 and/or decreased levels of expression of one or more genes of Table 12 can comprise i) obtaining or having obtained a sample from the subject and ii) performing or having performed an assay on the sample obtained from the subject to determine/measure the level of expression of one or more genes of Tables 11 and/or 12 in the subject. In some embodiments of any of the aspects, the step of determining if the subject has increased levels of expression of one or more genes of Table 11 and/or decreased levels of expression of one or more genes of Table 12 can comprise performing or having performed an assay on a sample obtained from the subject to determine/measure the level of expression of one or more genes of Tables 11 and/or 12 in the subject. In some embodiments of any of the aspects, the step of determining if the subject has increased levels of expression of one or more genes of Table 11 and/or decreased levels of expression of one or more genes of Table 12 can comprise ordering or requesting an assay on a sample obtained from the subject to determine/measure the level of expression of one or more genes of Tables 11 and/or 12 in the subject. In some embodiments of any of the aspects, the step of determining if the subject has increased levels of expression of one or more genes of Table 11 and/or decreased levels of expression of one or more genes of Table 12 can comprise receiving the results of an assay on a sample obtained from the subject to determine/measure the level of expression of one or more genes of Tables 11 and/or 12 in the subject. In some embodiments of any of the aspects, the step of determining if the subject has a increased levels of expression of one or more genes of Table 11 and/or decreased levels of expression of one or more genes of Table 12 can comprise receiving a report, results, or other means of identifying the subject as a subject with increased levels of expression of one or more genes of Table 11 and/or decreased levels of expression of one or more genes of Table 12.

In some embodiments of any of the aspects, the step of instructing or directing that the subject be administered a particular treatment can comprise providing a report of the assay results. In some embodiments of any of the aspects, the step of instructing or directing that the subject be administered a particular treatment can comprise providing a report of the assay results and/or treatment recommendations in view of the assay results.

In one aspect of any of the embodiments, described herein is a method of determining if a subject has a high or increased rate of FEV1, is at risk of a high or increased rate of FEV1, or is in need of treatment for a high or increased rate of FEV1, the method comprising: determining the level of expression of one or more genes of Tables 11 and/or 12 in a sample obtained from the subject, wherein increased levels of expression of one or more genes of Table 11 and/or decreased levels of expression of one or more genes of Table 12 relative to a reference indicates the subject has a high or increased rate of FEV1, is at risk of a high or increased rate of FEV1, or is in need of treatment for a high or increased rate of FEV1.

In some embodiments of any of the aspects, the methods described herein are directed to determination of the expression level of a gene product (e.g. protein and/or gene transcript such as mRNA) in a biological sample of a subject. In some embodiments of any of the aspects, the methods described herein are directed to determination of the expression level of a gene product of at least two genes in a biological sample of a subject, i.e. at least two genes, at least three genes, at least four genes, at least five genes, at least six genes, at least seven genes, at least eight genes, at least nine genes, at least 10 genes . . . at least 15 genes, . . . at least 25 genes, . . . at least 30 genes, or more genes, or any number of genes selected from any in a combination of Table 11 and Table 12 as described herein. In some embodiments of any of the aspects, one looks at a group of genes where some increase in expression and others decrease in expression. In some embodiments of any of the aspects, the expression level of a gene product of the same number of genes from each of Tables 11 and 12 is determined, e.g. two genes from each table. In some embodiments of any of the aspects, the expression level of a gene product of different numbers of genes from each of Tables 11 and 12 is determined, e.g. two genes from Table 11 and 4 genes from Table 12 or 6 genes from Table 11 and 3 genes from Table 12.

The gene names listed in Tables 11 and 12 are common names. The NCBI Gene ID numbers for each of the genes listed in Tables 11 and 12 are provided, and sequences for the genes and gene products in the Tables, as well as orthologs and annotation can be accessed via the NCBI entry associated with each Gene ID. In some embodiments of any of the aspect, the sequences of a gene expression product of a gene of Table 11 and/or Table 12 is the sequence deposited in the NCBI database for the relevant NCBI gene ID as of the filing date of this application.

TABLE 11

| cluster | Gene Name | NCBI Gene ID |
|---|---|---|
| 1 | Transcobalamin 1 (TCN1) | 6947 |
| 1 | Adenosylhomocysteinease like 2 (AHCYL2) | 23382 |
| 1 | N-acetylgalactosaminyltransferase 4 (GALNT4) | 8693 |
| 1 | major facilitator superfamily domain containing 4A (MFSD4) | 148808 |
| 1 | phospholipase A2 group IVA (PLA2G4A) | 5321 |
| 1 | tetraspanin 13 (TSPAN13) | 27075 |
| 1 | transmembrane 9 superfamily member 3 (TM9SF3) | 56889 |
| 1 | N-acetylgalactosaminyltransferase 5 (GALNT5) | 11227 |
| 1 | N-acetylgalactosaminyltransferase 7 (GALNT7) | 51809 |
| 1 | prostate androgen-regulated mucin-like protein 1 (PARM1) | 25849 |
| 1 | surfeit 4 (SURF4) | 6836 |
| 1 | N-acetylgalactosaminyltransferase 12 (GALNT12) | 79695 |
| 1 | armadillo repeat containing X-linked 3 (ARMCX3) | 51566 |
| 1 | CEA cell adhesion molecule 5 (CEACAM5) | 1048 |
| 1 | retinol dehydrogenase 10 (RDH10) | 157506 |
| 1 | ectonucleoside triphosphate diphosphohydrolase 4 (ENTPD4) | 9583 |
| 1 | fucosyltransferase 6 (FUT6) | 2528 |
| 1 | parathyroid hormone like hormone (PTHLH) | 5744 |
| 1 | asparaginase and isoaspartyl peptidase 1 (ASRGL1) | 80150 |
| 1 | S100 calcium binding protein A16 (S100A16) | 140576 |
| 1 | solute carrier family 26 member 2 (SLC26A2) | 1836 |
| 1 | cathepsin C (CTSC) | 1075 |
| 1 | leucine rich repeat containing 8 VRAC subunit A (LRRC8A) | 56262 |
| 1 | transmembrane protein 165 (TMEM165) | 55858 |
| 1 | pyridoxal dependent decarboxylase domain containing 1 (PDXDC1) | 23042 |
| 1 | glucosamine-phosphate N-acetyltransferase 1 (GNPNAT1) | 64841 |
| 1 | tetraspanin 8 (TSPAN8) | 7103 |
| 1 | solute carrier family 39 member 8 (SLC39A8) | 64116 |
| 1 | Magnesium transporter 1 (MAGT1) | 84061 |
| 1 | ATPase 13A5 (ATP13A5) | 344905 |
| 1 | claudin 10 (CLDN10) | 9071 |
| 1 | ectonucleoside triphosphate diphosphohydrolase 3 (ENTPD3) | 956 |
| 1 | fer-1 like family member 6 (FER1L6) | 654463 |
| 1 | phospholipid phosphatase 5 (PLPP5 or PPAPDC1B) | 84513 |
| 1 | adaptor related protein complex 2 subunit beta 1 (AP2B1) | 163 |
| 1 | S100 calcium binding protein A14 (S100A14) | 57402 |
| 1 | Sciellin (SCEL) | 8796 |
| 1 | UDP-galactose-4-epimerase (GALE) | 2582 |
| 1 | SEC31 homolog A, COPII coat complex component (SEC31A) | 22872 |
| 1 | alpha-2-glycoprotein 1, zinc-binding (AZGP1) | 563 |
| 1 | nicotinamide nucleotide transhydrogenase (NNT) | 23530 |
| 1 | armadillo repeat containing X-linked 6 (ARMCX6) | 54470 |
| 1 | uroplakin 1B (UPK1B) | 7348 |
| 1 | MORC family CW-type zinc finger 4 (MORC4) | 79710 |

TABLE 11-continued

| cluster | Gene Name | NCBI Gene ID |
|---|---|---|
| 1 | serine protease 23 (PRSS23) | 11098 |
| 1 | eukaryotic translation initiation factor 2 alpha kinase 3 (EIF2AK3) | 9451 |
| 1 | thioredoxin domain containing 11 (TXNDC11) | 51061 |
| 1 | solute carrier family 31 member 1 (SLC31A1) | 1317 |
| 1 | S100 calcium binding protein P (S100P) | 6286 |
| 1 | transmembrane serine protease 4 (TMPRSS4) | 56649 |
| 1 | frizzled class receptor 5 (FZD5) | 7855 |
| 1 | cAMP responsive element binding protein 3 like 1 (CREB3L1) | 90993 |
| 1 | family with sequence similarity 177 member B (FAM177B) | 400823 |
| 1 | MIA SH3 domain ER export factor 3 (MIA3) | 375056 |
| 1 | 3-hydroxy-3-methylglutaryl-CoA synthase 2 (HMGCS2) | 3158 |
| 1 | mucin 2 (MUC2) | 4583 |
| 1 | selenoprotein I (SELENO1 or EPT1) | 85465 |
| 1 | solute carrier family 44 member 3 (SLC44A3) | 126969 |
| 1 | WD repeat domain 72 (WDR72) | 256764 |
| 1 | serine/threonine kinase 38 like (STK38L) | 23012 |
| 1 | methylenetetrahydrofolate dehydrogenase (NADP + dependent) 2 (MTHFD2) | 10797 |
| 1 | V-set domain containing T cell activation inhibitor 1 (VTCN1) | 79679 |
| 1 | proline rich coiled-coil 1 (PRRC1) | 133619 |
| 1 | dispatched RND transporter family member 1 (DISP1) | 84976 |
| 1 | KDEL endoplasmic reticulum protein retention receptor 2 (KDELR2) | 11014 |
| 1 | SEC24 homolog A (SEC24A) | 10802 |
| 1 | potassium two pore domain channel subfamily K member 6 (KCNK6) | 9424 |
| 1 | diacylglycerol kinase alpha (DGKA) | 1606 |
| 1 | myosin 1C (MYO1C) | 4641 |
| 1 | ribophorin II (RPN2) | 6185 |
| 1 | ATPase H + transporting V0 subunit e1 (ATP6V0E1) | 8992 |
| 1 | fucosyltransferase 2 (FUT2) | 2524 |
| 1 | acyl-CoA binding domain containing 3 (ACBD3) | 64746 |
| 1 | cytochrome P450 family 2 subfamily C member 18 (CYP2C18) | 1562 |
| 1 | beta-1,4-galactosyltransferase 4 (B4GALT4) | 8702 |
| 1 | Anoctamin 10 (ANO10) | 55129 |
| 1 | serine protease 8 (PRSS8) | 5652 |
| 1 | vasoactive intestinal peptide receptor 1 (VIPR1) | 7433 |
| 1 | major facilitator superfamily domain containing 1 (MFSD1) | 64747 |
| 1 | glucosamine (UDP-N-acetyl)-2-epimerase/N-acetylmannosamine kinase (GNE) | 10020 |
| 1 | tetraspanin 5 (TSPAN5) | 10098 |
| 1 | transmembrane protein 39A (TMEM39A) | 55254 |
| 1 | solute carrier family 1 member 5 (SLC1A5) | 6510 |
| 1 | fucosyltransferase 3 (FUT3) | 2525 |
| 1 | LOC100128816 or | 100128816 |
| | an intron or splice variant of EF-hand calcium binding domain 4B (EFCAG4B) | 84766 |
| 1 | transmembrane protein 263 (TMEM263 or C12orf23) | 90488 |
| 1 | isocitrate dehydrogenase 1 (IDH1) | 3417 |
| 1 | transmembrane protein 167A (TMEM167A) | 153339 |
| 1 | adaptor related protein complex 4 subunit beta 1 (AP4B1) | 10717 |
| 1 | pyruvate dehydrogenase kinase 1 (PDK1) | 5163 |
| 1 | serine palmitoyltransferase small subunit A (SPTSSA) | 171546 |
| 1 | sphingomyelin phosphodiesterase acid like 3A (SMPDL3A) | 10924 |
| 1 | ADAM metallopeptidase domain 9 (ADAM9) | 8754 |
| 1 | solute carrier family 16 member 9 (SLC16A9) | 220963 |
| 1 | SEC61 translocon subunit alpha 1 (SEC61A1) | 29927 |
| 1 | acidic nuclear phosphoprotein 32 family member E (ANP32E) | 81611 |
| 1 | CEA cell adhesion molecule 6 (CEACAM6) | 4680 |
| 1 | transmembrane protein 211 (TMEM211) | 255349 |
| 1 | opsin 1, long wave sensitive (OPN1LW) | 5956 |
| 1 | fibroblast growth factor binding protein 1 (FGFBP1) | 9982 |
| 1 | solute carrier family 12 member 8 (SLC12A8) | 84561 |
| 1 | serpin family B member 8 (SERPINB8) | 5271 |
| 1 | cortactin binding protein 2 (CTTNBP2) | 83992 |
| 1 | BCL2 like 15 (BCL2L15) | 440603 |
| 1 | UDP-N-acetylglucosaminyltransferase subunit (ALG14) | 199857 |
| 1 | FKBP prolyl isomerase 14 (FKBP14) | 55033 |
| 1 | Zinc finger 391 (ZNF391) | 346157 |
| 1 | DEAH-box helicase 15 (DHX15) | 1665 |
| 1 | tubulin alpha 1c (TUBA1C) | 84790 |
| 1 | MOB family member 4 (MOB4 | 25843 |
| 1 | piggyBac transposable element derived 2 (PGBD2) | 267002 |
| 1 | potassium two pore domain channel subfamily K member 1 (KCNK1) | 3775 |
| 1 | mal, T cell differentiation protein 2 (MAL2) | 114569 |
| 1 | protein disulfide isomerase family A member 5 (PDIA5) | 10954 |
| 1 | trophoblast glycoprotein (TPBG) | 7162 |
| 1 | glutamic--pyruvic transaminase 2 (GPT2) | 84706 |
| 1 | transmembrane p24 trafficking protein 3 (TMED3) | 23423 |

TABLE 11-continued

| cluster | Gene Name | NCBI Gene ID |
|---|---|---|
| 1 | TIMP metallopeptidase inhibitor 1 (TIMP1) | 7076 |
| 1 | calcium activated nucleotidase 1 (CANT1) | 124583 |
| 1 | NIPA magnesium transporter 2 (NIPA2) | 81614 |

TABLE 12

| cluster | Gene Name | NCBI Gene ID |
|---|---|---|
| 2 | kinesin family member 13A (KIF13A) | 63971 |
| 2 | TBC1 domain family member 22B (TBC1D22B) | 55633 |
| 2 | coiled-coil domain containing 69 (CCDC69) | 26112 |
| 2 | protein kinase C epsilon (PRKCE) | 5581 |
| 2 | Bardet-Biedl syndrome 1 (BBS1) | 582 |
| 2 | family with sequence similarity 53 member B (FAM53B) | 9679 |
| 2 | spectrin repeat containing nuclear envelope family member 3 (SYNE3 or LINC00341) | 161176 |
| 2 | mastermind like transcriptional coactivator 2 (MAML2) | 84441 |
| 2 | SLIT-ROBO Rho GTPase activating protein 2 (SRGAP2) | 23380 |
| 2 | coiled-coil domain containing 170 (CCDC170) | 80129 |
| 2 | cyclin and CBS domain divalent metal cation transport mediator 2 (CNNM2) | 54805 |
| 2 | WW and C2 domain containing 1 (WWC1) | 23286 |
| 2 | Cluster of differentiation 38 (CD38) | 952 |
| 2 | H2B.U histone 1 (H2BU1 or HIST3H2BB) | 128312 |
| 2 | potassium voltage-gated channel subfamily B member 1 (KCNB1) | 3745 |
| 2 | hes related family bHLH transcription factor with YRPW motif 2 (HEY2) | 23493 |
| 2 | pericentrin (PCNT) | 5116 |
| 2 | junctional cadherin complex regulator (JHY or C11orf63) | 79864 |
| 2 | GRB2 associated binding protein 2 (GAB2) | 9846 |
| 2 | kinesin family member 24 (KIF24) | 347240 |
| 2 | zinc finger protein 709 (ZNF709) | 163051 |
| 2 | cytochrome P450 family 27 subfamily A member 1 (CYP27A1) | 1593 |
| 2 | forkhead associated phosphopeptide binding domain 1 (FHAD1) | 114827 |
| 2 | suppressor of cancer cell invasion (SCAI) | 286205 |
| 2 | BRF1 RNA polymerase III transcription initiation factor subunit (BRF1) | 2972 |
| 2 | zinc finger protein 382 (ZNF382) | 84911 |
| 2 | zinc finger protein 473 (ZNF473) | 25888 |
| 2 | zinc finger protein 544 (ZNF544) | 27300 |
| 2 | SNF related kinase (SNRK) | 54861 |
| 2 | centrosomal protein 250 (CEP250) | 11190 |
| 2 | ubiquitin specific peptidase 2 (USP2) | 9099 |
| 2 | syntaxin binding protein 1 (STXBP1) | 6812 |
| 2 | enolase 4 (ENO4) | 387712 |
| 2 | retrotransposon Gag like 5 (RTL5 or RGAG4) | 340526 |
| 2 | sperm tail PG-rich repeat containing 1 (STPG1) | 90529 |
| 2 | interleukin 5 receptor subunit alpha (IL5RA) | 3568 |
| 2 | unc-51 like autophagy activating kinase 2 (ULK2) | 9706 |
| 2 | zinc finger and BTB domain containing 44 (ZBTB44) | 29068 |
| 2 | NOP2/Sun RNA methyltransferase family member 7 (NSUN7) | 79730 |
| 2 | potassium inwardly rectifying channel subfamily J member 2 (KCNJ2) | 3759 |
| 2 | NIMA related kinase 4 (NEK4) | 6787 |
| 2 | centrosomal protein 104 (CEP104) | 9731 |
| 2 | outer dynein arm docking complex subunit 3 (ODAD3 or CCDC151) | 115948 |
| 2 | laminin subunit gamma 2 (LAMC2) | 3918 |
| 2 | NIMA related kinase 11 (NEK11) | 79858 |
| 2 | Zinc finger protein 82 (ZFP82) | 284406 |
| 2 | enhancer of zeste 1 (EZH1) | 2145 |
| 2 | proprotein convertase subtilisin/kexin type 6 (PCSK6) | 5046 |
| 2 | serine protease 12 (PRSS12) | 8492 |
| 2 | pygopus family PHD finger 1 (PYGO1) | 26108 |
| 2 | FXYD domain containing ion transport regulator 6 (FXYD6) | 53826 |

In some embodiments of any of the aspects, the level of expression of at least one of GALE, SEC61A1, KDELR2, EIF2AK3, S100A16, ADAM9, TMED3, MIA3, SURF4, and TXNDC11 is determined and/or the at least one gene of Tables 11 and/or 12 is at least one of GALE, SEC61A1, KDELR2, EIF2AK3, S100A16, ADAM9, TMED3, MIA3, SURF4, and TXNDC11. In some embodiments of any of the aspects, the level of expression of at least two of GALE, SEC61A1, KDELR2, EIF2AK3, S100A16, ADAM9, TMED3, MIA3, SURF4, and TXNDC11 is determined and/or the at least one gene of Tables 11 and/or 12 is at least two of GALE, SEC61A1, KDELR2, EIF2AK3, S100A16, ADAM9, TMED3, MIA3, SURF4, and TXNDC11. In some embodiments of any of the aspects, the level of expression of at least three of GALE, SEC61A1, KDELR2, EIF2AK3, S100A16, ADAM9, TMED3, MIA3, SURF4, and TXNDC11 is determined and/or the at least one gene of Tables 11 and/or 12 is at least three of GALE, SEC61A1, KDELR2, EIF2AK3, S100A16, ADAM9, TMED3, MIA3, SURF4, and TXNDC11. In some embodiments of any of the aspects, the level of expression of at least four of GALE, SEC61A1, KDELR2, EIF2AK3, S100A16, ADAM9, TMED3, MIA3, SURF4, and TXNDC11 is determined and/or the at least one gene of Tables 11 and/or 12 is at least four of GALE, SEC61A1, KDELR2, EIF2AK3, S100A16, ADAM9, TMED3, MIA3, SURF4, and TXNDC11. In some embodiments of any of the aspects, the level of expression of at least five of GALE, SEC61A1, KDELR2, EIF2AK3, S100A16, ADAM9, TMED3, MIA3, SURF4, and TXNDC11 is determined and/or the at least one gene of Tables 11 and/or 12 is at least five of GALE, SEC61A1, KDELR2, EIF2AK3, S100A16, ADAM9, TMED3, MIA3, SURF4, and TXNDC11. In some embodiments of any of the aspects, the level of expression of at least six of GALE, SEC61A1, KDELR2, EIF2AK3, S100A16, ADAM9, TMED3, MIA3, SURF4, and TXNDC11 is determined and/or the at least one gene of Tables 11 and/or 12 is at least six of GALE, SEC61A1, KDELR2, EIF2AK3, S100A16, ADAM9, TMED3, MIA3, SURF4, and TXNDC11. In some embodiments of any of the aspects, the level of expression of at least seven of GALE, SEC61A1, KDELR2, EIF2AK3, S100A16, ADAM9, TMED3, MIA3, SURF4, and TXNDC11 is determined and/or the at least one gene of Tables 11 and/or 12 is at least seven of GALE, SEC61A1, KDELR2, EIF2AK3, S100A16, ADAM9, TMED3, MIA3, SURF4, and TXNDC11. In some embodiments of any of the aspects, the level of expression of at least eight of GALE, SEC61A1, KDELR2, EIF2AK3, S100A16, ADAM9, TMED3, MIA3, SURF4, and TXNDC11 is determined and/or the at least one gene of Tables 11 and/or 12 is at least eight of GALE, SEC61A1, KDELR2, EIF2AK3, S100A16, ADAM9, TMED3, MIA3, SURF4, and TXNDC11. In some embodiments of any of the aspects, the level of expression of at least nine of GALE, SEC61A1, KDELR2, EIF2AK3, S100A16, ADAM9, TMED3, MIA3, SURF4, and TXNDC11 is determined and/or the at least one gene of Tables 11 and/or 12 is at least nine of GALE, SEC61A1, KDELR2, EIF2AK3, S100A16, ADAM9, TMED3, MIA3, SURF4, and TXNDC11. In some embodiments of any of the aspects, the level of expression of GALE, SEC61A1, KDELR2, EIF2AK3, S100A16, ADAM9, TMED3, MIA3, SURF4, and TXNDC11 is determined and/or the at least one gene of Tables 11 and/or 12 comprises GALE, SEC61A1, KDELR2, EIF2AK3, S100A16, ADAM9, TMED3, MIA3, SURF4, and TXNDC11.

EIF2AK3, S100A16, ADAM9, TMED3, MIA3, SURF4, and TXNDC11 are not direct targets of XBP1 regulation, e.g., XBP1 does not bind to/near and regulate transcription of these genes. In some embodiments of any of the aspects, the level of expression of at least one of EIF2AK3, S100A16, ADAM9, TMED3, MIA3, SURF4, and TXNDC11 is determined and/or the at least one gene of Tables 11 and/or 12 is at least one of EIF2AK3, S100A16, ADAM9, TMED3, MIA3, SURF4, and TXNDC11. In some embodiments of any of the aspects, the level of expression of at least two of EIF2AK3, S100A16, ADAM9, TMED3, MIA3, SURF4, and TXNDC11 is determined and/or the at least one gene of Tables 11 and/or 12 is at least two of EIF2AK3, S100A16, ADAM9, TMED3, MIA3, SURF4, and TXNDC11. In some embodiments of any of the aspects, the level of expression of at least three of EIF2AK3, S100A16, ADAM9, TMED3, MIA3, SURF4, and TXNDC11 is determined and/or the at least one gene of Tables 11 and/or 12 is at least three of EIF2AK3, S100A16, ADAM9, TMED3, MIA3, SURF4, and TXNDC11. In some embodiments of any of the aspects, the level of expression of at least four of EIF2AK3, S100A16, ADAM9, TMED3, MIA3, SURF4, and TXNDC11 is determined and/or the at least one gene of Tables 11 and/or 12 is at least four of EIF2AK3, S100A16, ADAM9, TMED3, MIA3, SURF4, and TXNDC11. In some embodiments of any of the aspects, the level of expression of at least five of EIF2AK3, S100A16, ADAM9, TMED3, MIA3, SURF4, and TXNDC11 is determined and/or the at least one gene of Tables 11 and/or 12 is at least five of EIF2AK3, S100A16, ADAM9, TMED3, MIA3, SURF4, and TXNDC11. In some embodiments of any of the aspects, the level of expression of at least six of EIF2AK3, S100A16, ADAM9, TMED3, MIA3, SURF4, and TXNDC11 is determined and/or the at least one gene of Tables 11 and/or 12 is at least six of EIF2AK3, S100A16, ADAM9, TMED3, MIA3, SURF4, and TXNDC11. In some embodiments of any of the aspects, the level of expression of at least EIF2AK3, S100A16, ADAM9, TMED3, MIA3, SURF4, and TXNDC11 is determined and/or the at least one gene of Tables 11 and/or 12 comprises EIF2AK3, S100A16, ADAM9, TMED3, MIA3, SURF4, and TXNDC11.

In some embodiments of any of the aspects, the level of expression of at least one of EIF2AK3, S100A16, ADAM9, MIA3, SURF4, and TXNDC11 is determined and/or the at least one gene of Tables 11 and/or 12 is at least one of EIF2AK3, S100A16, ADAM9, MIA3, SURF4, and TXNDC11. In some embodiments of any of the aspects, the level of expression of at least two of EIF2AK3, S100A16, ADAM9, MIA3, SURF4, and TXNDC11 is determined and/or the at least one gene of Tables 11 and/or 12 is at least two of EIF2AK3, S100A16, ADAM9, MIA3, SURF4, and TXNDC11. In some embodiments of any of the aspects, the level of expression of at least three of EIF2AK3, S100A16, ADAM9, MIA3, SURF4, and TXNDC11 is determined and/or the at least one gene of Tables 11 and/or 12 is at least three of EIF2AK3, S100A16, ADAM9, MIA3, SURF4, and TXNDC11. In some embodiments of any of the aspects, the level of expression of at least four of EIF2AK3, S100A16, ADAM9, MIA3, SURF4, and TXNDC11 is determined and/or the at least one gene of Tables 11 and/or 12 is at least four of EIF2AK3, S100A16, ADAM9, MIA3, SURF4, and TXNDC11. In some embodiments of any of the aspects, the level of expression of at least five of EIF2AK3, S100A16, ADAM9, MIA3, SURF4, and TXNDC11 is determined and/or the at least one gene of Tables 11 and/or 12 is at least five of EIF2AK3, S100A16, ADAM9, MIA3, SURF4, and TXNDC11. In some embodiments of any of the aspects, the level of expression of at least EIF2AK3, S100A16, ADAM9, MIA3, SURF4, and TXNDC11 is determined and/or the at least one gene of Tables 11 and/or 12 comprises EIF2AK3, S100A16, ADAM9, MIA3, SURF4, and TXNDC11.

In some embodiments of any of the aspects, the level of expression of only EIF2AK3, S100A16, ADAM9, MIA3, SURF4, and TXNDC11 is determined and/or the at least one gene of Tables 11 and/or 12 consists of EIF2AK3, S100A16, ADAM9, MIA3, SURF4, and TXNDC11. In some embodiments of any of the aspects, the level of expression of only EIF2AK3, S100A16, ADAM9, TMED3, MIA3, SURF4, and TXNDC11 is determined and/or the at least one gene of Tables 11 and/or 12 consists of EIF2AK3, S100A16, ADAM9, TMED3, MIA3, SURF4, and TXNDC11. In some embodiments of any of the aspects, the level of expression of only GALE, SEC61A1, KDELR2, EIF2AK3, S100A16, ADAM9, TMED3, MIA3, SURF4, and TXNDC1 is determined and/or the at least one gene of Tables 11 and/or 12 consists of GALE, SEC61A1, KDELR2, EIF2AK3, S100A16, ADAM9, TMED3, MIA3, SURF4, and TXNDC11.

In some embodiments of any of the aspects, the level of expression of one or more of NSUN7; LOC100128816; MTHFD2; KDELR2; SLC44A3; SLC16A9; TMED3; TSPAN13; SEC61A1; and FAM177B are not determined. In some embodiments of any of the aspects, the level of expression of NSUN7; LOC100128816; MTHFD2; KDELR2; SLC44A3; SLC16A9; TMED3; TSPAN13; SEC61A1; and FAM177B are not determined. In some embodiments of any of the aspects, the one or more genes of Tables 11 and/or 12 do not include NSUN7; LOC100128816; MTHFD2; KDELR2; SLC44A3; SLC16A9; TMED3; TSPAN13; SEC61A1; and FAM177B.

In some embodiments of any of the aspects, the level of expression of TCN1 is not determined. In some embodiments of any of the aspects, the one or more genes of Tables 11 and/or 12 do not include TCN1.

In some embodiments of any of the aspects, the level of expression of one of GALNT4, GALNT5, GALNT12, and/or MUC2 are not determined. In some embodiments of any of the aspects, the level of expression of GALNT4, GALNT5, GALNT12, and MUC2 are not determined. In some embodiments of any of the aspects, the one or more genes of Tables 11 and/or 12 do not include GALNT4, GALNT5, GALNT12, and/or MUC2.

In some embodiments of any of the aspects, the level of expression of one of ENO4 and CREB3L1 are not determined. In some embodiments of any of the aspects, the level of expression of ENO4 and CREB3L1 are not determined. In some embodiments of any of the aspects, the one or more genes of Tables 11 and/or 12 do not include ENO4 and CREB3L1.

In some embodiments of any of the aspects, measurement of the level of a target and/or detection of the level or presence of a target, e.g. of an expression product (nucleic acid or polypeptide of one of the genes described herein) or a mutation can comprise a transformation. As used herein, the term "transforming" or "transformation" refers to changing an object or a substance, e.g., biological sample, nucleic acid or protein, into another substance. The transformation can be physical, biological or chemical. Exemplary physical transformation includes, but is not limited to, pre-treatment of a biological sample, e.g., from whole blood to blood serum by differential centrifugation. A biological/chemical transformation can involve the action of at least one enzyme and/or a chemical reagent in a reaction. For example, a DNA sample can be digested into fragments by one or more restriction enzymes, or an exogenous molecule can be attached to a fragmented DNA sample with a ligase. In some embodiments of any of the aspects, a DNA sample can undergo enzymatic replication, e.g., by polymerase chain reaction (PCR).

Transformation, measurement, and/or detection of a target molecule, e.g. a mRNA or polypeptide can comprise contacting a sample obtained from a subject with a reagent (e.g. a detection reagent) which is specific for the target, e.g., a target-specific reagent. In some embodiments of any of the aspects, the target-specific reagent is detectably labeled. In some embodiments of any of the aspects, the target-specific reagent is capable of generating a detectable signal. In some embodiments of any of the aspects, the target-specific reagent generates a detectable signal when the target molecule is present.

Methods to measure gene expression products are known to a skilled artisan. Such methods to measure gene expression products, e.g., protein level, include ELISA (enzyme linked immunosorbent assay), western blot, immunoprecipitation, and immunofluorescence using detection reagents such as an antibody or protein binding agents. Alternatively, a peptide can be detected in a subject by introducing into a subject a labeled anti-peptide antibody and other types of detection agent. For example, the antibody can be labeled with a detectable marker whose presence and location in the subject is detected by standard imaging techniques.

For example, antibodies for the various targets described herein are commercially available and can be used for the purposes of the invention to measure protein expression levels, e.g. anti-GALE antibodies are commercially available (e.g., Cat. Nos. ab155997, ab155277, and ab118033; Abcam, Cambridge MA). Alternatively, since the amino acid sequences for the targets described herein are known and publically available at the NCBI website, one of skill in the art can raise their own antibodies against these polypeptides of interest for the purpose of the methods described herein.

The amino acid sequences of the polypeptides described herein have been assigned NCBI accession numbers for different species such as human, mouse and rat.

In some embodiments of any of the aspects, immunohistochemistry ("IHC") and immunocytochemistry ("ICC") techniques can be used. IHC is the application of immunochemistry to tissue sections, whereas ICC is the application of immunochemistry to cells or tissue imprints after they have undergone specific cytological preparations such as, for example, liquid-based preparations. Immunochemistry is a family of techniques based on the use of an antibody, wherein the antibodies are used to specifically target molecules inside or on the surface of cells. The antibody typically contains a marker that will undergo a biochemical reaction, and thereby experience a change of color, upon encountering the targeted molecules. In some instances, signal amplification can be integrated into the particular protocol, wherein a secondary antibody, that includes the marker stain or marker signal, follows the application of a primary specific antibody.

In some embodiments of any of the aspects, the assay can be a Western blot analysis. Alternatively, proteins can be separated by two-dimensional gel electrophoresis systems. Two-dimensional gel electrophoresis is well known in the art and typically involves iso-electric focusing along a first dimension followed by SDS-PAGE electrophoresis along a second dimension. These methods also require a considerable amount of cellular material. The analysis of 2D SDS-PAGE gels can be performed by determining the intensity of protein spots on the gel, or can be performed using immune detection. In other embodiments, protein samples are analyzed by mass spectroscopy.

Immunological tests can be used with the methods and assays described herein and include, for example, competitive and non-competitive assay systems using techniques such as Western blots, radioimmunoassay (RIA), ELISA (enzyme linked immunosorbent assay), "sandwich" immunoassays, immunoprecipitation assays, immunodiffusion assays, agglutination assays, e.g. latex agglutination, complement-fixation assays, immunoradiometric assays, fluorescent immunoassays, e.g. FIA (fluorescence-linked immunoassay), chemiluminescence immunoassays (CLIA), electrochemiluminescence immunoassay (ECLIA, counting immunoassay (CIA), lateral flow tests or immunoassay (LFIA), magnetic immunoassay (MIA), and protein A immunoassays. Methods for performing such assays are known in the art, provided an appropriate antibody reagent is available. In some embodiments of any of the aspects, the immunoassay can be a quantitative or a semi-quantitative immunoassay.

An immunoassay is a biochemical test that measures the concentration of a substance in a biological sample, typically a fluid sample such as blood or serum, using the interaction of an antibody or antibodies to its antigen. The assay takes advantage of the highly specific binding of an antibody with its antigen. For the methods and assays described herein, specific binding of the target polypeptides with respective proteins or protein fragments, or an isolated peptide, or a fusion protein described herein occurs in the immunoassay to form a target protein/peptide complex. The complex is then detected by a variety of methods known in the art. An immunoassay also often involves the use of a detection antibody.

Enzyme-linked immunosorbent assay, also called ELISA, enzyme immunoassay or EIA, is a biochemical technique used mainly in immunology to detect the presence of an antibody or an antigen in a sample. The ELISA has been used as a diagnostic tool in medicine and plant pathology, as well as a quality control check in various industries.

In one embodiment, an ELISA involving at least one antibody with specificity for the particular desired antigen (e.g., any of the targets as described herein) can also be performed. A known amount of sample and/or antigen is immobilized on a solid support (usually a polystyrene micro titer plate). Immobilization can be either non-specific (e.g., by adsorption to the surface) or specific (e.g. where another antibody immobilized on the surface is used to capture antigen or a primary antibody). After the antigen is immobilized, the detection antibody is added, forming a complex with the antigen. The detection antibody can be covalently linked to an enzyme, or can itself be detected by a secondary antibody which is linked to an enzyme through bio-conjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates with much higher sensitivity.

In another embodiment, a competitive ELISA is used. Purified antibodies that are directed against a target polypeptide or fragment thereof are coated on the solid phase of multi-well plate, i.e., conjugated to a solid surface. A second batch of purified antibodies that are not conjugated on any solid support is also needed. These non-conjugated purified antibodies are labeled for detection purposes, for example, labeled with horseradish peroxidase to produce a detectable signal. A sample (e.g., a blood sample) from a subject is mixed with a known amount of desired antigen (e.g., a known volume or concentration of a sample comprising a target polypeptide) together with the horseradish peroxidase labeled antibodies and the mixture is then are added to coated wells to form competitive combination. After incubation, if the polypeptide level is high in the sample, a complex of labeled antibody reagent-antigen will form. This complex is free in solution and can be washed away. Washing the wells will remove the complex. Then the wells are incubated with TMB (3,3',5,5'-tetramethylbenzidene) color development substrate for localization of horseradish peroxidase-conjugated antibodies in the wells. There will be no color change or little color change if the target polypeptide level is high in the sample. If there is little or no target polypeptide present in the sample, a different complex in formed, the complex of solid support bound antibody reagents-target polypeptide. This complex is immobilized on the plate and is not washed away in the wash step. Subsequent incubation with TMB will produce significant color change. Such a competitive ELSA test is specific, sensitive, reproducible and easy to operate.

There are other different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; and Oellerich, M. 1984, J. Clin. Chem. Clin. Biochem. 22:895-904. These references are hereby incorporated by reference in their entirety.

In one embodiment, the levels of a polypeptide in a sample can be detected by a lateral flow immunoassay test (LFIA), also known as the immunochromatographic assay, or strip test. LFIAs are a simple device intended to detect the presence (or absence) of antigen, e.g. a polypeptide, in a fluid sample. There are currently many LFIA tests used for medical diagnostics, either for home testing, point of care testing, or laboratory use. LFIA tests are a form of immunoassay in which the test sample flows along a solid substrate via capillary action. After the sample is applied to the test strip it encounters a colored reagent (generally comprising antibody specific for the test target antigen) bound to microparticles which mixes with the sample and transits the substrate encountering lines or zones which have been pretreated with another antibody or antigen. Depending upon the level of target polypeptides present in the sample the colored reagent can be captured and become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water, and/or homogenized tissue samples etc. Strip tests are also known as dip stick tests, the name bearing from the literal action of "dipping" the test strip into a fluid sample to be tested. LFIA strip tests are easy to use, require minimum training and can easily be included as components of point-of-care test (POCT) diagnostics to be use on site in the field. LFIA tests can be operated as either competitive or sandwich assays. Sandwich LFIAs are similar to sandwich ELISA. The sample first encounters colored particles which are labeled with antibodies raised to the target antigen. The test line will also contain antibodies to the same target, although it may bind to a different epitope on the antigen. The test line will show as a colored band in positive samples. In some embodiments of any of the aspects, the lateral flow immunoassay can be a double antibody sandwich assay, a competitive assay, a quantitative assay or variations thereof. Competitive LFIAs are similar to competitive ELISA. The sample first encounters colored particles which are labeled with the target antigen or an analogue. The test line contains antibodies to the target/its analogue. Unlabelled antigen in the sample will block the binding sites on the antibodies preventing uptake of the colored particles. The test line will show as a colored band in negative samples. There are a number of variations on lateral flow technology. It is also possible to apply multiple capture zones to create a multiplex test.

The use of "dip sticks" or LFIA test strips and other solid supports have been described in the art in the context of an immunoassay for a number of antigen biomarkers. U.S. Pat. Nos. 4,943,522; 6,485,982; 6,187,598; 5,770,460; 5,622,871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Examples of patents that describe the use of "dip stick"

technology to detect soluble antigens via immunochemical assays include, but are not limited to U.S. Pat. Nos. 4,444,880; 4,305,924; and 4,135,884; which are incorporated by reference herein in their entireties. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teachings of this "dip stick" technology for the detection of polypeptides using antibody reagents as described herein.

Other techniques can be used to detect the level of a polypeptide in a sample. One such technique is the dot blot, an adaptation of Western blotting (Towbin et at., Proc. Nat. Acad. Sci. 76:4350 (1979)). In a Western blot, the polypeptide or fragment thereof can be dissociated with detergents and heat, and separated on an SDS-PAGE gel before being transferred to a solid support, such as a nitrocellulose or PVDF membrane. The membrane is incubated with an antibody reagent specific for the target polypeptide or a fragment thereof. The membrane is then washed to remove unbound proteins and proteins with non-specific binding. Detectably labeled enzyme-linked secondary or detection antibodies can then be used to detect and assess the amount of polypeptide in the sample tested. A dot blot immobilizes a protein sample on a defined region of a support, which is then probed with antibody and labelled secondary antibody as in Western blotting. The intensity of the signal from the detectable label in either format corresponds to the amount of enzyme present, and therefore the amount of polypeptide. Levels can be quantified, for example by densitometry.

In some embodiments of any of the aspects, the level of a target can be measured, by way of non-limiting example, by Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy and/or immunoelectrophoresis assay.

In certain embodiments, the expression levels as described herein can be determined by determining the level of messenger RNA (mRNA) expression of the genes described herein. Such molecules can be isolated, derived, or amplified from a biological sample, such as a blood sample. Techniques for the detection of mRNA expression is known by persons skilled in the art, and can include but not limited to, PCR procedures, RT-PCR, quantitative RT-PCR Northern blot analysis, differential gene expression, RNAse protection assay, microarray based analysis, next-generation sequencing; hybridization methods, etc.

In general, the PCR procedure describes a method of gene amplification which is comprised of (i) sequence-specific hybridization of primers to specific genes or sequences within a nucleic acid sample or library, (ii) subsequent amplification involving multiple rounds of annealing, elongation, and denaturation using a thermostable DNA polymerase, and (iii) screening the PCR products for a band of the correct size. The primers used are oligonucleotides of sufficient length and appropriate sequence to provide initiation of polymerization, i.e. each primer is specifically designed to be complementary to a strand of the genomic locus to be amplified. In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art.

In some embodiments of any of the aspects, the level of an mRNA can be measured by a quantitative sequencing technology, e.g. a quantitative next-generation sequence technology. Methods of sequencing a nucleic acid sequence are well known in the art. Briefly, a sample obtained from a subject can be contacted with one or more primers which specifically hybridize to a single-strand nucleic acid sequence flanking the target gene sequence and a complementary strand is synthesized. In some next-generation technologies, an adaptor (double or single-stranded) is ligated to nucleic acid molecules in the sample and synthesis proceeds from the adaptor or adaptor compatible primers. In some third-generation technologies, the sequence can be determined, e.g. by determining the location and pattern of the hybridization of probes, or measuring one or more characteristics of a single molecule as it passes through a sensor (e.g. the modulation of an electrical field as a nucleic acid molecule passes through a nanopore). Exemplary methods of sequencing include, but are not limited to, Sanger sequencing, dideoxy chain termination, high-throughput sequencing, next generation sequencing, 454 sequencing, SOLiD sequencing, polony sequencing, Illumina sequencing, Ion Torrent sequencing, sequencing by hybridization, nanopore sequencing, Helioscope sequencing, single molecule real time sequencing, RNAP sequencing, and the like. Methods and protocols for performing these sequencing methods are known in the art, see, e.g. "Next Generation Genome Sequencing" Ed. Michal Janitz, Wiley-VCH; "High-Throughput Next Generation Sequencing" Eds. Kwon and Ricke, Humanna Press, 2011; and Sambrook et al., Molecular Cloning: A Laboratory Manual (4 ed.), Cold Spring Harbor Laboratory Press, Cold Spring Harbor, N.Y., USA (2012); which are incorporated by reference herein in their entireties.

The nucleic acid sequences of the genes described herein have been assigned NCBI accession numbers for different species such as human, mouse and rat. Accordingly, a skilled artisan can design an appropriate primer based on the known sequence for determining the mRNA level of the respective gene.

Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)).

In some embodiments of any of the aspects, one or more of the reagents (e.g. an antibody reagent and/or nucleic acid probe) described herein can comprise a detectable label and/or comprise the ability to generate a detectable signal (e.g. by catalyzing reaction converting a compound to a detectable product). Detectable labels can comprise, for example, a light-absorbing dye, a fluorescent dye, or a radioactive label. Detectable labels, methods of detecting them, and methods of incorporating them into reagents (e.g. antibodies and nucleic acid probes) are well known in the art.

In some embodiments of any of the aspects, detectable labels can include labels that can be detected by spectroscopic, photochemical, biochemical, immunochemical, electromagnetic, radiochemical, or chemical means, such as fluorescence, chemifluoresence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the reagent. Alternatively, a detectable label can be linked such as by directly labeling a molecule that achieves binding to the reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection reagent is label with a fluorescent compound. When the fluorescently labeled reagent is exposed to light of the proper wavelength, its presence can then be detected due to fluorescence. In some embodiments of any of the aspects, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfhiorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. In some embodiments of any of the aspects, a detectable label can be a radiolabel including, but not limited to $^3$H, $^{125}$I, $^{35}$S, $^{14}$C, $^{32}$P, and $^{33}$P. In some embodiments of any of the aspects, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. In some embodiments of any of the aspects, a detectable label is a chemiluminescent label, including, but not limited to lucigenin, luminol, luciferin, isoluminol, theromatic acridinium ester, imidazole, acridinium salt and oxalate ester. In some embodiments of any of the aspects, a detectable label can be a spectral colorimetric label including, but not limited to colloidal gold or colored glass or plastic (e.g., polystyrene, polypropylene, and latex) beads.

In some embodiments of any of the aspects, detection reagents can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i.e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e.g. from DAKO; Carpinteria, CA A reagent can also be detectably labeled using fluorescence emitting metals such as $^{152}$Eu, or others of the lanthanide series. These metals can be attached to the reagent using such metal chelating groups as diethylenetriaminepentaacetic acid (DTPA) or ethylene diaminetetraacetic acid (EDTA).

In some embodiments of any of the aspects, an increased or decreased level of expression is increased or decreased relative to a reference, e.g., a reference level.

A level which is less than a reference level can be a level which is less by at least about 10%, at least about 20%, at least about 50%, at least about 60%, at least about 80%, at least about 90%, or less relative to the reference level. In some embodiments of any of the aspects, a level which is less than a reference level can be a level which is statistically significantly less than the reference level.

A level which is more than a reference level can be a level which is greater by at least about 10%, at least about 20%, at least about 50%, at least about 60%, at least about 80%, at least about 90%, at least about 100%, at least about 200%, at least about 300%, at least about 500% or more than the reference level. In some embodiments of any of the aspects, a level which is more than a reference level can be a level which is statistically significantly greater than the reference level.

In some embodiments of any of the aspects, the reference can be a level of the target molecule in a population of subjects who do not have or are not diagnosed as having, and/or do not exhibit signs or symptoms of COPD. In some embodiments of any of the aspects, the reference can be a level of the target molecule in a population of subjects who are never-smokers. In some embodiments of any of the aspects, the reference can also be a level of expression of the target molecule in a control sample, a pooled sample of control individuals or a numeric value or range of values based on the same. In some embodiments of any of the aspects, the reference can be the level of a target molecule in a sample obtained from the same subject at an earlier point in time, e.g., the methods described herein can be used to determine if a subject's sensitivity or response to a given therapy is changing over time.

In some embodiments of any of the aspects, the reference level can be the level in a sample of similar cell type, sample type, sample processing, and/or obtained from a subject of similar age, sex and other demographic parameters as the sample/subject for which the level of expression is to be determined. In some embodiments of any of the aspects, the reference level can be the level in a sample obtained from a reference subject of similar age as the subject for which the level of expression is to be determined. In some embodiments of any of the aspects, the test sample and control reference sample are of the same type, that is, obtained from the same biological source, and comprising the same composition, e.g. the same number and type of cells.

In some embodiments of any of the aspects, the level is the level in a bronchial brushing, bronchial biopsy, bronchial epithelium sample, airway epithelium sample, nasal brushing, and/or nasal epithelium sample. In some embodiments of any of the aspects, the level is the level in a bronchial brushing, bronchial biopsy, bronchial epithelium sample, and/or airway epithelium sample. In some embodiments of any of the aspects, the level is the level in a nasal epithelium sample.

In some embodiments of any of the aspects, the expression level of a given gene can be normalized relative to the expression level of one or more reference genes or reference proteins.

In some embodiments of any of the aspects, the level of expression products of no more than 400 other genes is determined. In some embodiments of any of the aspects, the level of expression products of no more than 200 other genes is determined. In some embodiments of any of the aspects, the level of expression products of no more than 100 other genes is determined. In some embodiments of any of the aspects, the level of expression products of no more than 20 other genes is determined. In some embodiments of any of the aspects, the level of expression products of no more than 10 other genes is determined.

In some embodiments of any of the aspects, the level of expression products of no more than 400 genes is determined. In some embodiments of any of the aspects, the level of expression products of no more than 200 genes is determined. In some embodiments of any of the aspects, the level of expression products of no more than 100 genes is determined. In some embodiments of any of the aspects, the level of expression products of no more than 20 genes is determined. In some embodiments of any of the aspects, the level of expression products of no more than 10 genes is determined.

The term "sample" or "test sample" as used herein denotes a sample taken or isolated from a biological organism, e.g., a blood or plasma sample from a subject. In some embodiments of any of the aspects, the present invention encompasses several examples of a biological sample. In some embodiments of any of the aspects, the biological sample is cells, or tissue, or peripheral blood, or bodily fluid. Exemplary biological samples include, but are not limited to, a biopsy, a tumor sample, biofluid sample; blood; serum; plasma; urine; sperm; mucus; tissue biopsy; organ biopsy; synovial fluid; bile fluid; cerebrospinal fluid; mucosal secretion; effusion; sweat; saliva; and/or tissue sample etc. The term also includes a mixture of the above-mentioned samples. The term "test sample" also includes untreated or pretreated (or pre-processed) biological samples. In some embodiments of any of the aspects, a test sample can comprise cells from a subject. In some embodiments of any of the aspects, the test sample can be a bronchial brushing, bronchial biopsy, bronchial epithelium sample, airway epithelium sample, nasal brushing, and/or nasal epithelium sample. In some embodiments of any of the aspects, the test sample can be a bronchial brushing, bronchial biopsy, bronchial epithelium sample, and/or airway epithelium sample. In some embodiments of any of the aspects, the test sample can be a nasal epithelium sample.

The test sample can be obtained by removing a sample from a subject, but can also be accomplished by using a previously isolated sample (e.g. isolated at a prior timepoint and isolated by the same or another person).

In some embodiments of any of the aspects, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments of any of the aspects, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments of any of the aspects, the test sample is a clarified test sample, for example, by centrifugation and collection of a supernatant comprising the clarified test sample. In some embodiments of any of the aspects, a test sample can be a pre-processed test sample, for example, supernatant or filtrate resulting from a treatment selected from the group consisting of centrifugation, filtration, thawing, purification, and any combinations thereof. In some embodiments of any of the aspects, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

In some embodiments of any of the aspects, the methods, assays, and systems described herein can further comprise a step of obtaining or having obtained a test sample from a subject. In some embodiments of any of the aspects, the subject can be a human subject. In some embodiments of any of the aspects, the subject can be a subject in need of treatment for (e.g. having or diagnosed as having) COPD or a subject at risk of or at increased risk of developing COPD as described elsewhere herein.

In some embodiments, the methods described herein relate to treating a subject having or diagnosed as having COPD. In some embodiments of any of the aspects, the subject is a current or former tobacco smoker. In some embodiments of any of the aspects, the subject has been exposed to asbestos, air pollution, or environmental hazards. In some embodiments of any of the aspects, the environmental hazard is dust, chemicals, fire, or smoke. In some embodiments of any of the aspects, the subject has or is diagnosed as having COPD. In some embodiments of any of the aspects, the subject has a GOLD grade of 2 or lower.

In some embodiments of any of the aspects, the subject is a mammal. In some embodiments of any of the aspects, the subject is a human. In some embodiments of any of the aspects, the subject is at least 49 years old. In some embodiments of any of the aspects, the subject is at least 58 years old.

In some embodiments of any of the aspects, a subject determined to have an increased level of expression of one or more genes of Table 11 and/or a decreased level of expression of one or more genes of Table 12 is administered one of an inhaled long acting antimuscarinic, an inhaled long-acting β2 agonist, and an inhaled corticosteroid. In some embodiments of any of the aspects, a subject determined to have an increased level of expression of one or more genes of Table 11 and/or a decreased level of expression of one or more genes of Table 12 is administered two of an inhaled long acting antimuscarinic, an inhaled long-acting β2 agonist, and an inhaled corticosteroid. In some embodiments of any of the aspects, a subject determined to have an increased level of expression of one or more genes of Table 11 and/or a decreased level of expression of one or more genes of Table 12 is administered an inhaled long acting antimuscarinic and an inhaled long-acting β2 agonist. In some embodiments of any of the aspects, a subject determined to have an increased level of expression of one or more genes of Table 11 and/or a decreased level of expression of one or more genes of Table 12 is administered an inhaled long acting antimuscarinic and an inhaled corticosteroid. In some embodiments of any of the aspects, a subject determined to have an increased level of expression of one or more genes of Table 11 and/or a decreased level of expression of one or more genes of Table 12 is administered an inhaled long-acting β2 agonist and an inhaled corticosteroid. In some embodiments of any of the aspects, a subject determined to have an increased level of expression of one or more genes of Table 11 and/or a decreased level of expression of one or more genes of Table 12 is administered all of an inhaled long acting antimuscarinic, an inhaled long-acting β2 agonist, and an inhaled corticosteroid.

As used herein, "long-acting" refers to therapeutics that control and prevent symptoms, while "short-acting" refers to therapeutics that provide quick relief from symptoms (usually bronchoconstriction). These terms are standard terms of art in the use of bronchodilators and one of ordinary skill in the art is aware of which agents and effects fall into each classification.

In some embodiments of any of the aspects, a subject is administered a long-acting antimuscarinic in accordance with the methods described herein. An antimuscarinic or muscarinic receptor antagonist is an anticholinergic agent that inhibits the muscarinic acetylcholine receptor. Long-acting antimuscarinics suitable for treatment of COPD and/or respiratory conditions are known in the art and include but are not limited to tiotropium; ipratropium; umiclinidium; aclidinium; and diphenhydramine. In some embodiments of any of the aspects, the long-acting antimuscarinic is tiotropium or umiclinidium.

In some embodiments of any of the aspects, a subject is administered a long-acting β2 agonist in accordance with the methods described herein. A long-acting β2 agonist is an agonist of the β2 adrenergic receptor to induce muscle relaxation. Long-acting β2 agonists suitable for treatment of COPD and/or respiratory conditions are known in the art and include but are not limited to fomoterol; salmeterol; arformoterol; bambuterol; and clenbuterol. Long-acting β2 agonists can also include ultra long-acting β2 agonists, e.g., abediterol, carmoterol, olodaterol, indacaterol, and vlianterol. In some embodiments of any of the aspects, the long-acting β2 agonist is fomoterol or salmeterol.

In some embodiments of any of the aspects, a subject is administered an inhaled corticosteroid in accordance with the methods described herein. "Corticosteroid" refers to a class of steroid hormones that are produced in the adrenal cortex or produced synthetically. Corticosteroids are involved in a wide range of physiologic systems such as stress response, immune response and regulation of inflammation, carbohydrate metabolism, protein catabolism, blood electrolyte levels, and behavior. Corticosteroids are generally grouped into four classes, based on chemical structure. Group A corticosteroids (short to medium acting glucocorticoids) include hydrocortisone, hydrocortisone acetate, cortisone acetate, tixocortol pivalate, prednisolone, methylprednisolone, and prednisone. Group B corticosteroids include triamcinolone acetonide, triamcinolone alcohol, mometasone, amcinonide, budesonide, desonide, fluocinonide, fluocinolone acetonide, and halcinonide. Group C corticosteroids include betamethasone, betamethasone sodium phosphate, dexamethasone, dexamethasone sodium phosphate, and fluocortolone. Group D corticosteroids include hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate. Inhaled corticosteroid suitable for treatment of COPD and/or respiratory conditions are known in the art and include but are not limited to budesonide; fluticasone; flunisolide; triamcinolone acetonide; beclomethasone dipropionate; mometasone furoate; and ciclesonide. In some embodiments of any of the aspects, the inhaled corticosteroid is budesonide or fluticasone.

In some embodiments of any of the aspects, a subject determined to not have an increased level of expression of one or more genes of Table 11 and/or a decreased level of expression of one or more genes of Table 12 is administered one of a short-acting β2 agonist and intensive smoking cessation therapy. In some embodiments of any of the aspects, a subject determined to not have an increased level of expression of one or more genes of Table 11 and/or a decreased level of expression of one or more genes of Table 12 is administered a short-acting β2 agonist and intensive smoking cessation therapy.

In some embodiments of any of the aspects, a subject is administered a short-acting β2 agonist in accordance with the methods described herein. A short-acting β2 agonist is an agonist of the β2 adrenergic receptor to induce muscle relaxation. Short-acting β2 agonists suitable for treatment of COPD and/or respiratory conditions are known in the art and include but are not limited to albuterol; bitolterol; fenoterol; isoprenaline; isoproterenol; levosalbutamol; levalbuterol; orciprenaline; metaproterenol; pirbuterol; procaterol; ritodrine; salbutamol; and terbutaline. In some embodiments of any of the aspects, the short-acting β2 agonist is albuterol.

In some embodiments of any of the aspects, a subject is administered intensive smoking cessation therapy in accordance with the methods described herein. Intensive smoking cessation therapy can include one or more of: nicotine replacement therapy, transdermal nicotine replacement therapy, counseling, and programs such as the Gold Standard Program.

In some embodiments of any of the aspects, the treatment administered to a subject determined to have an increased level of expression of one or more genes of Table 11 and/or a decreased level of expression of one or more genes of Table 12 further comprises administration of an inhibitor of one or more genes of Table 11 and/or an agonist of one or more genes of Table 12. In one aspect of any of the embodiments, provided herein is a method of treating COPD comprising administering an inhibitor of one or more genes of Table 11 and/or an agonist of one or more genes of Table 12. In one aspect of any of the embodiments, provided herein is an inhibitor of one or more genes of Table 11 and/or an agonist of one or more genes of Table 12 for use in a method of treating COPD. In some embodiments of any of the aspects, the subject is determined to have an increased level of expression of one or more genes of Table 11 and/or a decreased level of expression of one or more genes of Table 12. In some embodiments of any of the aspects, the method comprises a first step of determining the level of expression of one or more genes of Table 11 and/or Table 12 in a sample obtained from the subject.

As used herein, the terms "drug", "compound" or "agent" are used interchangeably and refer to molecules and/or compositions. The compounds/agents include, but are not limited to, chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; nucleic acids; nucleic acid analogs and derivatives; extracts made from biological materials such as bacteria, plants, fungi, or animal cells or tissues; naturally occurring or synthetic compositions; peptides; aptamers; and antibodies and intrabodies, or fragments thereof. In some embodiments, "drug" as used herein refers to an agent approved for medical use, e.g., by the FDA.

As used herein, "inhibitor" refers to an agent which can decrease the expression and/or activity of a target, e.g. by at least 10% or more, e.g. by 10% or more, 50% or more, 70% or more, 80% or more, 90% or more, 95% or more, or 98% or more. The efficacy of an inhibitor of one or more targets, e.g. its ability to decrease the level and/or activity of the target can be determined, e.g. by measuring the level of an expression product of the target and/or the activity of the target. In some embodiments of any of the aspects, the inhibitor can be an inhibitory nucleic acid; an aptamer; an antibody reagent; an antibody; or a small molecule. An inhibitor of a target described herein can inhibit the activity, expression, or accumulation of the target polypeptide. Inhibitors can include inhibitors that act directly on the target itself (e.g., that bind to the protein or transcript, e.g., direct inhibitors).

In some embodiments of any of the aspects, an inhibitor of a specified target is an antibody, antibody reagent, or antigen-binding fragment thereof, that specifically binds to the target.

In some embodiments of any of the aspects, the agent that inhibits one or more genes of Table 11 is an inhibitory nucleic acid. In some embodiments of any of the aspects, inhibitors of the expression of a given gene can be an inhibitory nucleic acid. As used herein, "inhibitory nucleic acid" refers to a nucleic acid molecule which can inhibit the expression of a target, e.g., double-stranded RNAs (dsRNAs), inhibitory RNAs (iRNAs), and the like. In some embodiments of any of the aspects, the inhibitory nucleic acid can be a silencing RNA (siRNA), microRNA (miRNA), or short hairpin RNA (shRNA). Inhibitory nucleic acids can also include guide sequence molecules (e.g., a guide RNA) that function, e.g., in combination with an enzyme, to induce insertions, deletions, indels, and/or mutations of a target, thereby inhibiting the expression of the target.

In some embodiments of any of the aspects, an iNA comprises a sequence that is complementary to at least a portion of a target sequence described herein. In some embodiments of any of the aspects, an iNA comprises a sequence at least 15 nucleotides in length that is complementary to at least a portion of a target sequence described herein. In some embodiments of any of the aspects, an iNA comprises a sequence at least 20 nucleotides in length that is complementary to at least a portion of a target sequence described herein.

In some embodiments of any of the aspects, an iNA comprises a sequence that is the reverse complement to at least a portion of a target sequence described herein. In some embodiments of any of the aspects, an iNA comprises a sequence at least 15 nucleotides in length that is the reverse complement to at least a portion of a target sequence described herein. In some embodiments of any of the aspects, an iNA comprises a sequence at least 20 nucleotides in length that is the reverse complement to at least a portion of a target sequence described herein.

In some embodiments of any of the aspects, an iNA comprises a sequence that can specifically hybridize to at least a portion of a target sequence described herein. In some embodiments of any of the aspects, an iNA comprises a sequence at least 15 nucleotides in length that can specifically hybridize to at least a portion of a target sequence described herein. In some embodiments of any of the aspects, an iNA comprises a sequence at least 20 nucleotides in length that can specifically hybridize to at least a portion of a target sequence described herein.

Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part the targeted mRNA transcript. The use of these iRNAs enables the targeted degradation of mRNA transcripts, resulting in decreased expression and/or activity of the target.

As used herein, the term "iRNA" refers to an agent that contains RNA (or modified nucleic acids as described below herein) and which mediates the targeted cleavage of an RNA transcript via an RNA-induced silencing complex (RISC) pathway. In some embodiments of any of the aspects, an iRNA as described herein effects inhibition of the expression and/or activity of a target. In some embodiments of any of the aspects, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA. In some embodiments of any of the aspects, administering an inhibitor (e.g. an iRNA) to a subject results in a decrease in the target mRNA level in the subject by at least about 5%, about 10%, about 20%, about 30%, about 40%, about 50%, about 60%, about 70%, about 80%, about 90%, about 95%, about 99%, up to and including 100% of the target mRNA level found in the subject without the presence of the iRNA.

In some embodiments of any of the aspects, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target, e.g., it can span one or more intron boundaries. The other strand (the sense strand) includes a region that is complementary to the antisense strand, such that the two strands hybridize and form a duplex structure when combined under suitable conditions. Generally, the duplex structure is between 15 and 30 base pairs in length inclusive, more generally between 18 and 25 base pairs in length inclusive, yet more generally between 19 and 24 base pairs in length inclusive, and most generally between 19 and 21 base pairs in length, inclusive. Similarly, the region of complementarity to the target sequence is between 15 and 30 base pairs in length inclusive, more generally between 18 and 25 base pairs in length inclusive, yet more generally between 19 and 24 base pairs in length inclusive, and most generally between 19 and 21 base pairs in length nucleotides in length, inclusive. In some embodiments of any of the aspects, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

Exemplary embodiments of types of inhibitory nucleic acids can include, e.g., siRNA, shRNA, miRNA, and/or amiRNA, which are well known in the art. One skilled in the art would be able to design further siRNA, shRNA, or miRNA to target the nucleic acid sequence of a gene of Table 11, e.g., using publically available design tools. siRNA, shRNA, or miRNA is commonly made using companies such as Dharmacon (Layfayette, CO) or Sigma Aldrich (St. Louis, MO).

In some embodiments of the various aspects described herein, the inhibitory nucleic acid is a guide nucleic acid (gNA). As used herein, the terms "guide nucleic acid," "guide sequence," "crRNA," "guide RNA," "single guide RNA," "gRNA" or "CRISPR guide sequence" refer to a nucleic acid comprising a sequence that determines the specificity of an enzyme, e.g., the Cas DNA binding protein of a CRISPR/Cas system, to a polynucleotide target. The gNA can comprise a polynucleotide sequence with at least partial complementarity with a target nucleic acid sequence, sufficient to hybridize with the target nucleic acid sequence and to direct sequence-specific binding of an enzyme, e.g, a nuclease, to the target nucleic acid sequence.

In some embodiments, the enzyme directed by the gNA is a gene-editing protein, e.g., any nuclease that induces a nick or double-strand break into a desired recognition site. Such enzymes can be native or engineered. These breaks can then be repaired by the cell in one of two ways: non-homologous end joining and homology-directed repair (homologous recombination). In non-homologous end joining (NHEJ), the double-strand breaks are repaired by direct ligation of the break ends to one another. As such, no new nucleic acid material is inserted into the site, although some nucleic acid material may be lost, resulting in a deletion. In homology-directed repair, a donor polynucleotide with homology to the cleaved target DNA sequence can be used as a template for repair of the cleaved target DNA sequence, resulting in the transfer of genetic information from the donor polynucleotide to the target DNA. Therefore, new nucleic acid material may be inserted/copied into the site. The modifications of the target DNA due to NHEJ and/or homology-directed repair can be used for gene correction, gene replacement, gene tagging, transgene insertion, nucleotide deletion, gene disruption, gene mutation, etc.

In one embodiment, the gene-editing protein is a CRISPR-associated nuclease. The native prokaryotic CRISPR-associated nuclease system comprises an array of short repeats with intervening variable sequences of constant length (i.e., clusters of regularly interspaced short palindromic repeats), and CRISPR-associated ("Cas") nuclease proteins. The RNA of the transcribed CRISPR array is processed by a subset of the Cas proteins into small guide RNAs, which generally have two components as discussed below. There are at least three different systems: Type I, Type II and Type III. The enzymes involved in the processing of the RNA into mature crRNA are different in the 3 systems. In the native prokaryotic system, the guide RNA ("gRNA") comprises two short, non-coding RNA species referred to as CRISPR RNA ("crRNA") and trans-acting RNA ("tracrRNA"). In an exemplary system, the gRNA forms a complex with a nuclease, for example, a Cas nuclease. The gRNA: nuclease complex binds a target polynucleotide sequence having a protospacer adjacent motif ("PAM") and a protospacer, which is a sequence complementary to a portion of the gRNA. The recognition and binding of the target polynucleotide by the gRNA: nuclease complex induces cleavage of the target.

Any CRISPR-associated nuclease can be used in the system and methods of the invention. CRISPR nuclease systems are known to those of skill in the art, e.g. Cas9, Cas12, Cas12a, or the like, see U.S. Pat. No. 8,993,233, US 2015/0291965, US 2016/0175462, US 2015/0020223, US 2014/0179770, 8,697,359; 8,771,945; 8, 795,965; WO 2015/191693; U.S. Pat. No. 8,889,418; WO 2015/089351; WO 2015/089486; WO 2016/028682; WO 2016/049258; WO 2016/094867; WO 2016/094872; WO 2016/094874; WO 2016/112242; US 2016/0153004; US 2015/0056705; US 2016/0090607; US 2016/0029604; 8,865,406; 8,871,445; each of which are incorporated by reference in their entirety. The nuclease can also be a phage Cas nuclease, e.g., CasΦ (e.g., Pausch et al. Science 369:333-7 (2020); which is incorporated by reference herein in its entirety).

The full-length guide nucleic acid strand can be any length. For example, the guide nucleic acid strand can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments of the various aspects described herein, a nucleic acid strand is less than about 75, 50, 45, 40, 35, 30, 25, 20, 15, 12, or fewer nucleotides in length. For example, the guide nucleic acid sequence is 10-30 nucleotides long.

In addition to a sequence that is complementary to a target nucleic acid, in some embodiments, the gNA also comprises a scaffold sequence. Expression of a gNA encoding both a sequence complementary to a target nucleic acid and scaffold sequence has the dual function of both binding (hybridizing) to the target nucleic acid and recruiting the endonuclease to the target nucleic acid, which may result in site-specific CRISPR activity. In some embodiments, such a chimeric gNA may be referred to as a single guide RNA (sgRNA).

In some embodiments of the various aspects described herein, the guide nucleic acid is designed using a guide design tool (e.g., Benchling™; Broad Institute GPP™; CasOFFinder™; CHOPCHOP™; CRISPOR™; Deskgen™; E-CRISP™; Geneious™; GenHub™; GUIDES™ (e.g., for library design); Horizon Discovery™; IDT™; Off-Spotter™; and Synthego™; which are available on the world wide web).

In some embodiments of any of the aspects, the RNA of an iRNA, e.g., a dsRNA, is chemically modified to enhance stability or other beneficial characteristics. The nucleic acids described herein may be synthesized and/or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments of any of the aspects, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; others having mixed N, O, S and CH2 component parts, and oligonucleosides with heteroatom backbones, and in particular —CH2-NH—CH2-, —CH2-N(CH3)-O—CH2-[known as a methylene (methylimino) or MMI backbone], —CH2-O—N(CH3)-CH2-, —CH2-N(CH3)-N(CH3)-CH2- and —N(CH3)-CH2-CH2—[wherein the native phosphodiester backbone is represented as —O—P—O—CH2-].

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) Nucleic Acids Research 33(1):439-447; Mook, O R. et al., (2007) Mol Canc Ther 6(3):833-843; Grunweller, A. et al., (2003) Nucleic Acids Research 31(12): 3185-3193).

Modified RNAs can also contain one or more substituted sugar moieties. The iRNAs, e.g., dsRNAs, described herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include O[(CH2)nO]mCH3, O(CH2)·nOCH3, O(CH2)nNH2, O(CH2)nCH3, O(CH2)nONH2, and O(CH2)nON[(CH2)nCH3)]2, where n and m are from 1 to about 10. In some embodiments of any of the aspects, dsRNAs include one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments of any of the aspects, the modification includes a 2' methoxyethoxy (2'-O—CH2CH2OCH3, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2, also described in examples herein below.

Other modifications include 2'-methoxy (2'-OCH3), 2'-aminopropoxy (2'-OCH2CH2CH2NH2) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar.

An inhibitory nucleic acid can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Certain of these nucleobases are particularly useful for increasing the binding affinity of the inhibitory nucleic acids featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

The preparation of the modified nucleic acids, backbones, and nucleobases described above are well known in the art.

Another modification of an inhibitory nucleic acid featured in the invention involves chemically linking to the inhibitory nucleic acid to one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylaminocarbonyloxycholesterol moiety (Crooke et al., J. Pharmacol. Exp. Ther., 1996, 277:923-937).

In some embodiments of any of the aspects, the inhibitor of one or more genes of Table 11 can be an antibody reagent, e.g., an antibody reagent that binds specifically to and inhibits one or more genes of Table 11. Antibody reagents specific for the targets and/or markers described herein, e.g., Table 11 are known in the art. For example, such reagents are readily commercially available. By way of non-limiting example anti-GALE antibodies are commercially available (e.g., Cat. Nos. ab155997, ab155277, and ab118033; Abcam, Cambridge MA).

As used herein, the term "agonist" refers to an agent which increases the expression and/or activity of the target by at least 10% or more, e.g. by 10% or more, 50% or more, 100% or more, 200% or more, 500% or more, or 1000% or more. The efficacy of an agonist, e.g. its ability to increase the level and/or activity of the target can be determined, e.g. by measuring the level of an expression product of the target and/or the activity of the target. Methods for measuring the level of a given mRNA and/or polypeptide are known to one of skill in the art, e.g. RTPCR with primers can be used to determine the level of RNA, and Western blotting with an antibody can be used to determine the level of a polypeptide.

Suitable primers for a given target are readily identified by one of skill in the art, e.g., using software widely available for this purpose (e.g., Primer3 or PrimerBank, which are both available on the world wide web). Antibodies to polypeptide gene expression products of the immune response regulators described herein are commercially available, e.g., from AbCam (Cambridge, MA). Assays for measuring the activity of the targets described herein are provided elsewhere herein. In some embodiments of any of the aspects, an agonist of a given polypeptide can be the polypeptide, a nucleic acid encoding the polypeptide, or a small molecule.

Non-limiting examples of agonists of a given polypeptide target, can include the target polypeptides or variants or functional fragments thereof and nucleic acids encoding the polypeptide or variants or functional fragments thereof. In some embodiments of any of the aspects, the agonist of a given target, is a polypeptide of that target or variants or functional fragment thereof and/or a nucleic acid encoding the polypeptide or variant or functional fragment thereof. In some embodiments of any of the aspects, the polypeptide agonist can be an engineered and/or recombinant polypeptide. In some embodiments of any of the aspects, the polypeptide agonist can be a nucleic acid encoding a polypeptide, e.g. a functional fragment thereof. In some embodiments of any of the aspects, the nucleic acid can be comprised by a vector.

In some embodiments of any of the aspects, a polypeptide agonist can comprise one of the sequences provided herein for each target. In some embodiments of any of the aspects, a polypeptide agonist can consist essentially of one of the sequences provided below herein for each target. In some embodiments of any of the aspects, a polypeptide agonist can consist of one of the sequences provided below herein for each target. In some embodiments of any of the aspects, an agonist can comprise a nucleic acid encoding one of the sequences provided below herein for each target. In some embodiments of any of the aspects, an agonist can be a polypeptide comprising a reference/wild-type sequence provided herein with at least 80%, at least 85%, at least 90%, at least 95%, or at least 98% identity to the reference/wild-type sequence and which retains the activity of the reference/wild-type sequence. In some embodiments of any of the aspects, an agonist can be a polypeptide comprising a reference/wild-type sequence provided herein with at least 95% identity to the reference/wild-type sequence and which retains the activity of the reference/wild-type sequence.

In some embodiments of any of the aspects, the agonist is an exogenous polypeptide. In some embodiments of any of the aspects, the subject is administered exogenous polypeptide, e.g., the polypeptide is produced in vitro and/or synthesized and purified polypeptide is provided to the subject. In some embodiments of any of the aspects, the agonist is an ectopic polypeptide. In some embodiments of any of the aspects, the subject is administered ectopic polypeptide, e.g., the polypeptide is produced in vitro and/or synthesized and purified polypeptide is provided to the subject.

In some embodiments of any of the aspects, the agonist can be a nucleic acid encoding a polypeptide (or a variant or functional fragment thereof) and/or a vector comprising a nucleic acid encoding a polypeptide (or a variant or functional fragment thereof). A nucleic acid encoding a polypeptide can be, e.g., an RNA molecule, a plasmid, and/or an expression vector. In some embodiments of any of the aspects, the nucleic acid encoding a polypeptide can be an mRNA. In some embodiments of any of the aspects, the nucleic acid encoding a polypeptide can be a modified mRNA. In some embodiments of any of the aspects, the agonist can be a nucleic acid encoding a polypeptide, e.g., exogenous and/or ectopic polypeptide. In some embodiments of any of the aspects, the subject is administered the nucleic acid encoding exogenous and/or ectopic polypeptide, e.g., the nucleic acid is transcribed and/or translated after the administering step to provide exogenous and/or ectopic polypeptide to the subject.

In some embodiments of any of the aspects, a polypeptide or nucleic acid as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments of any of the aspects, the agonist and/or inhibitor is administered as a nucleic acid. In some embodiments of any of the aspects, a nucleic acid encoding the agonist and/or inhibitor is administered. In some embodiments of any of the aspects, the subject is administered a vector comprising a nucleic acid. Vectors can be, e.g., a DNA or RNA vector.

Certain aspects of the invention provided herein relate to methods of treating COPD in a subject. COPD can be characterized as a destruction of both small airways and parenchyma resulting in a progressive impairment in pulmonary function. The disease may be divided into two subgroups, namely chronic bronchitis and emphysema. Chronic bronchitis is characterized by mucus hypersecretion from the conducting airways, inflammation and eventual scarring of the bronchi (airway tubes). Many persons with COPD have a component of both of these conditions.

The interaction between parenchymal disease and the vasculature is often clinically evident by the observation that patients with severe COPD have mild or moderate pulmonary hypertension at rest. Histopathologically and microscopically, the pulmonary vasculature in COPD is typically characterized by initial thickening with smooth muscle deposition as well as a loss of both alveolar septal structures and microvasculature. Furthermore, in COPD it has been observed that both alveolar septal and endothelial cells undergo apoptosis.

The presenting symptoms for COPD are typically breathlessness accompanied by a decline in FEV1 (i.e., forced expiratory volume in 1 second). COPD patients have difficulty breathing because they develop smaller, inflamed air passageways and have partially destroyed alveoli. Chronic bronchitis can also be diagnosed by asking the patient whether they have a "productive cough," i.e. one that yields sputum. The patients' symptoms are cough and expectoration of sputum. Chronic bronchitis can lead to more frequent and severe respiratory infections, narrowing and plugging of the bronchi, difficult breathing and disability. If airflow obstruction is present and reversibility less than 15%, particularly in a smoker, then they are often diagnosed as having COPD.

Subjects having COPD can be identified by a physician using current methods of diagnosing emphysema and/or COPD. Symptoms of COPD which characterize these conditions and aid in diagnosis are described above.

Subjects at risk of having or developing COPD include subjects who have smoked tobacco or been exposed to tobacco smoke. Cigarette smoke is considered to be a major risk factor in the development of COPD and its effects on the lung epithelium have been well characterized. Without wishing to be constrained by theory, it is believed that cigarette smoke induces necrosis and apoptosis of both epithelial and endothelial cells which contributes to the pathogenesis of COPD.

Additional factors which increase the likelihood of a subject developing COPD include, but are not limited to, asbestos, environmental factors, predisposed genetic factor (e.g. AAT deficiency), exposure to tobacco products, exposure to chemicals, pollutants, and other factors that are known to increase the risk of COPD. For example, smokers are at a higher risk in developing COPD compared to non-smokers. In one particular embodiment, a subject at risk of developing COPD emphysema refers to a subject who has been smoking at least ½ to one pack of cigarettes for at least 1 year, typically at least 3 years, more typically at least 5 years, still more typically at least 10 years, and most typically at least 20 years. In certain embodiments, a subject at risk of having or developing COPD emphysema is a subject who has been exposed to asbestos or a subject having a decreased level of AAT in the blood.

The compositions and methods described herein can be administered to a subject having or diagnosed as having COPD. In some embodiments, the methods described herein comprise administering an effective amount of compositions described herein to a subject in order to alleviate a symptom of COPD. As used herein, "alleviating a symptom" is ameliorating any condition or symptom associated with the disease. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

The term "effective amount" as used herein refers to the amount of an agent needed to alleviate at least one or more symptom of the disease or disorder, and relates to a sufficient amount of pharmacological composition to provide the desired effect. The term "therapeutically effective amount" therefore refers to an amount of an agent that is sufficient to provide a particular therapeutic effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of an agent, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay or test, e.g., for FEV1, among others. The dosage can be determined by a physician and adjusted, as necessary, to suit observed effects of the treatment.

In some embodiments, the technology described herein relates to a pharmaceutical composition comprising an agonist and/or inhibitor as described herein, and optionally a pharmaceutically acceptable carrier. In some embodiments, the active ingredients of the pharmaceutical composition comprise an agonist and/or inhibitor as described herein. In some embodiments, the active ingredients of the pharmaceutical composition consist essentially of an agonist and/or inhibitor as described herein. In some embodiments, the active ingredients of the pharmaceutical composition consist of an agonist and/or inhibitor as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent as described herein.

In some embodiments, the pharmaceutical composition described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of an agent as disclosed herein can also be incorporated into the parenteral dosage forms of the disclosure, including conventional and controlled-release parenteral dosage forms.

Pharmaceutical compositions can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia PA (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the composition can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments of any of the aspects, an agent or treatment described herein is administered as a monotherapy, e.g., another treatment for COPD is not administered to the subject.

In some embodiments of any of the aspects, the methods described herein can further comprise administering a second agent and/or treatment to the subject, e.g. as part of a combinatorial therapy.

In certain embodiments, an effective dose of a composition as described herein can be administered to a patient once. In certain embodiments, an effective dose of a composition can be administered to a patient repeatedly. For systemic administration, subjects can be administered a therapeutic amount of a composition such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active ingredient. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition can be administered over a period of time, such as over a 5 minute, 10 minute, 15 minute, 20 minute, or 25 minute period.

The dosage ranges, according to the methods described herein depend upon, for example, the form of the active ingredient, its potency, and the extent to which symptoms, markers, or indicators of a condition described herein are desired to be reduced, for example the percentage reduction desired for COPD symptoms. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of an agent or treatment in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. FEV1 or the rate of change thereof. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of COPD. When using an experimental animal model, efficacy of treatment is evidenced when a statistically significant change in a marker is observed, e.g. one or more of the genes described herein.

In one aspect of any of the embodiments, provided herein is method comprising determining the level of expression of one or more genes of Table 11 and/or Table 12 in a sample obtained from a subject, wherein the sample is a bronchial brushing, bronchial biopsy, bronchial epithelium sample, airway epithelium sample, nasal brushing, and/or nasal epithelium sample.

In one aspect of any of the embodiments, described herein is a method of identifying a treatment as effective in treating respiratory disease (e.g., COPD and/or FEV1 decrease), the method comprising: contacting cell with a candidate agent, or administering to subject a candidate treatment agent; and identifying the candidate treatment agent as effective if the level of expression of one or more genes of Table 11 decreases, and/or the level of expression of one or more genes of Table 12 increases.

As used herein, the terms "candidate compound" or "candidate agent" refer to a compound or agent and/or compositions thereof that are to be screened for their ability to, e.g., treat a respiratory disease. Candidate compounds and/or agents can be produced recombinantly using methods well known to those of skill in the art (see Sambrook et al., Molecular Cloning: A Laboratory Manual (2 ed.), Cold Spring Harbor Laboratory Press, Cold Spring Harbor, N.Y., USA (1989)) or synthesized. Candidate compounds and agents can be screened for their ability treat a respiratory disease as described herein. In one embodiment, candidate agents are screened using the assays described herein.

Compounds can be tested at any concentration that can modulate expression or protein activity relative to a control over an appropriate time period. In some embodiments of any of the aspects, compounds are tested at concentrations in the range of about 0.1 nM to about 1000 mM. In one embodiment, the compound is tested in the range of about 0.1 µM to about 20 µM, about 0.1 µM to about 10 µM, or about 0.1 µM to about 5 µM. In one embodiment, compounds are tested at 1 µM. Depending upon the particular embodiment being practiced, the test compounds can be provided free in solution, or may be attached to a carrier, or a solid support, e.g., beads. A number of suitable solid supports may be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds may be screened individually, or in groups. Group screening is particularly useful where hit rates for effective test compounds are expected to be low such that one would not expect more than one positive result for a given group.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of COPD. A subject can be male or female.

A subject can be one who has been previously diagnosed with or identified as suffering from or having a condition in need of treatment (e.g. COPD) or one or more complications related to such a condition, and optionally, have already undergone treatment for COPD or the one or more complications related to COPD. Alternatively, a subject can also be one who has not been previously diagnosed as having COPD or one or more complications related to COPD. For example, a subject can be one who exhibits one or more risk factors for COPD or one or more complications related to COPD or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing. The terms also refer to fragments or variants of the polypeptide that maintain at least 50% of the activity or effect, of the full length polypeptide. Conservative substitution variants that maintain the activity of the wildtype will include a conservative substitution as defined herein. The identification of amino acids most likely to be tolerant of conservative substitution while maintaining at least 50% of the activity of the wildtype is guided by, for example, sequence alignment with homologs or paralogs from other species. Amino acids that are identical between homologs are less likely to tolerate change, while those showing conservative differences are obviously much more likely to tolerate conservative change in the context of an artificial variant. Similarly, positions with non-conservative differences are less likely to be critical to function and more likely to tolerate conservative substitution in an artificial variant. Variants, fragments, and/or fusion proteins can be tested for activity, for example, by administering the variant to an appropriate animal model of COPD as described herein.

One method of identifying amino acid residues which can be substituted is to align, for example, the human sequence to a homolog from one or more non-human species. Alignment can provide guidance regarding not only residues likely to be necessary for function but also, conversely, those residues likely to tolerate change. Where, for example, an alignment shows two identical or similar amino acids at corresponding positions, it is more likely that that site is important functionally. Where, conversely, alignment shows residues in corresponding positions to differ significantly in size, charge, hydrophobicity, etc., it is more likely that that site can tolerate variation in a functional polypeptide. The variant amino acid or DNA sequence can be at least 90%, at least 95%, at least 96%, at least 97%, at least 98%, at least 99%, or more, identical to a native or reference sequence, or a nucleic acid encoding one of those amino acid sequences. The degree of homology (percent identity) between a native and a mutant sequence can be determined, for example, by comparing the two sequences using freely available computer programs commonly employed for this purpose on the world wide web. The variant amino acid or DNA sequence can be at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp or BLASTn (available on the world wide web at blast.ncbi.nlm.nih.gov), with default parameters set.

In some embodiments, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (mRNA) or antisense RNA derived from a nucleic acid fragment or fragments of the invention and/or to the translation of mRNA into a polypeptide.

In some embodiments, the expression of a biomarker(s), target(s), or gene/polypeptide described herein is/are tissue-specific. In some embodiments, the expression of a biomarker(s), target(s), or gene/polypeptide described herein is/are global. In some embodiments, the expression of a biomarker(s), target(s), or gene/polypeptide described herein is systemic.

"Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

"Marker" in the context of the present invention refers to an expression product, e.g., nucleic acid or polypeptide which is differentially present in a sample taken from subjects having a condition or risk, as compared to a comparable sample taken from control subjects (e.g., a healthy subject). The term "biomarker" is used interchangeably with the term "marker."

In some embodiments, the methods described herein relate to measuring, detecting, or determining the level of at least one marker. As used herein, the term "detecting" or "measuring" refers to observing a signal from, e.g. a probe, label, or target molecule to indicate the presence of an analyte in a sample. Any method known in the art for detecting a particular label moiety can be used for detection. Exemplary detection methods include, but are not limited to, spectroscopic, fluorescent, photochemical, biochemical, immunochemical, electrical, optical or chemical methods. In some embodiments of any of the aspects, measuring can be a quantitative observation.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments of any of the aspects, an agent (e.g, inhibitor or agonist) described herein is exogenous. In some embodiments of any of the aspects, the agent described herein is ectopic. In some embodiments of any of the aspects, the agent described herein is not endogenous.

The term "exogenous" refers to a substance present in a cell other than its native source. The term "exogenous" when used herein can refer to a nucleic acid (e.g. a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell. As used herein, "ectopic" refers to a substance that is found in an unusual location and/or amount. An ectopic substance can be one that is normally found in a given cell, but at a much lower amount and/or at a different time. Ectopic also includes substance, such as a polypeptide or nucleic acid that is not naturally found or expressed in a given cell in its natural environment.

In some embodiments, a nucleic acid as described herein (e.g. encoding an inhibitory nucleic acid or a polypeptide) is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

In some embodiments of any of the aspects, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

In some embodiments of any of the aspects, the vector or nucleic acid described herein is codon-optimized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments of any of the aspects, the expression system is an organism other than the source of the native/wild-type sequence (or a cell obtained from such organism). In some embodiments of any of the aspects, the vector and/or nucleic acid sequence described herein is codon-optimized for expression in a mammal or mammalian cell, e.g., a mouse, a murine cell, or a human cell. In some embodiments of any of the aspects, the vector and/or nucleic acid sequence described herein is codon-optimized for expression in a human cell. In some embodiments of any of the aspects, the vector and/or nucleic acid sequence described herein is codon-optimized for expression in a yeast or yeast cell. In some embodiments of any of the aspects, the vector and/or nucleic acid sequence described herein is codon-optimized for expression in a bacterial cell. In some embodiments of any of the aspects, the vector and/or nucleic acid sequence described herein is codon-optimized for expression in an *E. coli* cell.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art.

It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. COPD. The term "treating" includes reducing or alleviating at least one adverse effect or symptom of a condition, disease or disorder associated with COPD. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

In some embodiments of any of the aspects, described herein is a prophylactic method of treatment. As used herein "prophylactic" refers to the timing and intent of a treatment relative to a disease or symptom, that is, the treatment is administered prior to clinical detection or diagnosis of that particular disease or symptom in order to protect the patient from the disease or symptom. Prophylactic treatment can encompass a reduction in the severity or speed of onset of the disease or symptom, or contribute to faster recovery from the disease or symptom. Accordingly, the methods described herein can be prophylactic relative to a worsening of COPD or onset of symptoms not already present. In some embodiments of any of the aspects, prophylactic treatment is not prevention of all symptoms or signs of a disease.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

In a combination of agents, the different agents can be provided in a mixture or single formulation. Alternatively, the different agents can be provided in separate formulations that are packaged or provided as a set or kit.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject. In some embodiments, administration comprises physical human activity, e.g., an injection, act of ingestion, an act of application, and/or manipulation of a delivery device or machine. Such activity can be performed, e.g., by a medical professional and/or the subject being treated.

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art. In some embodiments, contacting comprises physical human activity, e.g., an injection; an act of dispensing, mixing, and/or decanting; and/or manipulation of a delivery device or machine.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments as well as complete antibodies.

As used herein, the term "antibody" refers to immunoglobulin molecules and immunologically active portions of immunoglobulin molecules, i.e., molecules that contain an antigen binding site that immunospecifically binds an antigen. The term also refers to antibodies comprised of two immunoglobulin heavy chains and two immunoglobulin light chains as well as a variety of forms including full length antibodies and antigen-binding portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding portion thereof, and/or bifunctional hybrid antibodies. Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

Antibodies and/or antibody reagents can include an immunoglobulin molecule, a monoclonal antibody, a chimeric antibody, a CDR-grafted antibody, a humanized antibody, a fully human antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a functionally active epitope-binding portion thereof.

As used herein, the term "nanobody" or single domain antibody (sdAb) refers to an antibody comprising the small single variable domain (VHH) of antibodies obtained from camelids and dromedaries. Antibody proteins obtained from members of the camel and dromedary (*Camelus baclrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994; which is incorporated by reference herein in its entirety).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J. 17: 3512-3520; each of which is incorporated by reference herein in its entirety. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody. The low molecular weight and compact size further result in camelid nanobodies being extremely thermostable, stable to extreme pH and to proteolytic digestion, and poorly antigenic. See U.S. patent application 20040161738 published Aug. 19, 2004; which is incorporated by reference herein in its entirety. These features combined with the low antigenicity to humans indicate great therapeutic potential.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of treating chronic obstructive pulmonary disease (COPD), the method comprising:
   a. administering one or more of an inhaled long acting antimuscarinic, an inhaled long-acting β2 agonist, and an inhaled corticosteroid to a subject determined to have an increased level of expression of one or more genes of Table 11 and/or a decreased level of expression of one or more genes of Table 12; and
   b. administering one or more of intensive smoking cessation therapy and an inhaled short-acting β2 agonist to a subject determined not to have an increased level of expression of one or more genes of Table 11 and/or a decreased level of expression of one or more genes of Table 12.
2. The method of any of the preceding paragraphs, wherein the one or more genes of Table 11 and/or one or more genes of Table 12 comprise at least one of GALE; SEC61A1; KDELR2; EIF2AK3; S100A16; ADAM9; TMED3; MIA3; SURF4; and TXNDC11.
3. The method of any of the preceding paragraphs, wherein the one or more genes of Table 11 and/or one or more genes of Table 12 comprise GALE; SEC61A1; KDELR2; EIF2AK3; S100A16; ADAM9; TMED3; MIA3; SURF4; and TXNDC11.

4. The method of any of the preceding paragraphs, wherein the one or more genes of Table 11 and/or one or more genes of Table 12 comprise EIF2AK3; S100A16; ADAM9; TMED3; MIA3; SURF4; and TXNDC11.

5. The method of any of the preceding paragraphs, wherein the one or more genes of Table 11 and/or one or more genes of Table 12 comprise EIF2AK3; S100A16; ADAMS; MIA3; SURF4; and TXNDC11.

6. The method of any of the preceding paragraphs, wherein the level of expression of one or more of NSUN7; LOC100128816; MTHFD2; KDELR2; SLC44A3; SLC16A9; TMED3; TSPAN13; SEC61A1; and FAM177B are not determined.

7. The method of any of the preceding paragraphs, wherein the level of expression of one or both of ENO4 and CREB3L1 are not determined.

8. The method of any of the preceding paragraphs, wherein the expression of no more than 400 genes is determined.

9. The method of any of the preceding paragraphs, wherein the expression of no more than 200 genes is determined.

10. The method of any of the preceding paragraphs, wherein the expression of no more than 100 genes is determined.

11. The method of any of the preceding paragraphs, wherein an increased or decreased level is the level relative to a patient who has never been a smoker.

12. The method of any of the preceding paragraphs, wherein an increased or decreased level is the level relative to an age-matched patient who has never been a smoker.

13. The method of any of the preceding paragraphs, wherein the level is the level in a bronchial brushing, bronchial biopsy, bronchial epithelium, airway epithelium, nasal brushing, and/or nasal epithelium.

14. The method of any of the preceding paragraphs, wherein the level is the level in the nasal epithelium.

15. The method of any of the preceding paragraphs, wherein the subject is a current or former tobacco smoker.

16. The method of any of the preceding paragraphs, wherein the subject has been exposed to asbestos, air pollution, or environmental hazards.

17. The method of paragraph 11, wherein the environmental hazard is dust, chemicals, fire, or smoke.

18. The method of any of the preceding paragraphs, wherein the subject has or is diagnosed as having COPD.

19. The method of any of the preceding paragraphs, wherein the subject is a mammal.

20. The method of any of the preceding paragraphs, wherein the subject is a human.

21. The method of any of the preceding paragraphs, wherein the human subject is at least 49 years old.

22. The method of any of the preceding paragraphs, wherein the human subject is at least 58 years old.

23. The method of any of the preceding paragraphs, wherein the subject has a GOLD grade of 2 or lower.

24. The method of any of the preceding paragraphs, wherein the inhaled long-acting antimuscarinic is selected from the group consisting of: tiotropium; ipratropium; umiclinidium; aclidinium; and diphenhydramine.

25. The method of any of the preceding paragraphs, wherein the inhaled long-acting β2 agonist is selected from the group consisting of: fomoterol; salmeterol; arformoterol; bambuterol; clenbuterol abediterol; carmoterol; olodaterol; indacaterol; and vlianterol.

26. The method of any of the preceding paragraphs, wherein the inhaled corticosteroid is selected from the group consisting of: budesonide; fluticasone; flunisolide; triamcinolone acetonide; beclomethasone dipropionate; mometasone furoate; and ciclesonide.

27. The method of any of the preceding paragraphs, wherein the inhaled short-acting β2 agonist is selected from the group consisting of: albuterol; bitolterol; fenoterol; isoprenaline; isoproterenol; levosalbutamol; levalbuterol; orciprenaline; metaproterenol; pirbuterol; procaterol; ritodrine; salbutamol; and terbutaline.

28. The method of any of the preceding paragraphs, wherein the treatment administered to a subject determined to have an increased level of expression of one or more genes of Table 11 and/or a decreased level of expression of one or more genes of Table 12 further comprises administration of an inhibitor of one or more genes of Table 11 and/or an agonist of one or more genes of Table 12.

29. A method of treating COPD comprising administering an inhibitor of one or more genes of Table 11 and/or an agonist of one or more genes of Table 12.

30. The method of paragraph 29, wherein the subject is determined to have an increased level of expression of one or more genes of Table 11 and/or a decreased level of expression of one or more genes of Table 12.

31. The method of any of paragraphs 29-30, wherein the administering step comprises the administration of a vector comprising a nucleic acid encoding the agonist and/or inhibitor.

32. A method of determining if a subject has a high or increased rate of FEV1, is at risk of a high or increased rate of FEV1, or is in need of treatment for a high or increased rate of FEV1, the method comprising:
determining the level of expression of one or more genes of Tables 11 and/or 12 in a sample obtained from the subject,
wherein increased levels of expression of one or more genes of Table 11 and/or decreased levels of expression of one or more genes of Table 12 relative to a reference indicates the subject has a high or increased rate of FEV1, is at risk of a high or increased rate of FEV1, or is in need of treatment for a high or increased rate of FEV1.

33. A non-invase method of identifying a subject at risk for COPD comprising:
determining the level of expression of one or more genes of Tables 11 and/or 12 in a sample obtained from the subject,
wherein increased levels of expression of one or more genes of Table 11 and/or decreased levels of expression of one or more genes of Table 12 relative to a reference indicates the subject is at risk for COPD.

34. A composition or combination comprising an inhaled long acting antimuscarinic, an inhaled long-acting β2 agonist, an inhaled corticosteroid, an inhibitor of at least one gene of Table 11, and/or an agonist of at least one gene of Table 12 for use in a method of treating a respiratory disease in a subject in need thereof, wherein the subject is one determined to have an increased level of expression of one or more genes of Table 11 and/or a decreased level of expression of one or more genes of Table 12.

35. The composition or combination of paragraph 34, wherein the respiratory disease is COPD.

36. A method comprising determining the level of expression of one or more genes of Table 11 and/or Table 12 in a sample obtained from a subject, wherein the sample is a bronchial brushing, bronchial biopsy, bronchial epithelium sample, airway epithelium sample, nasal brushing, and/or nasal epithelium sample.

37. The method, composition, or combination of any of paragraphs 32-36, wherein the one or more genes of Table 11 and/or at least one or more genes of Table 12 comprise at least one of GALE; SEC61A1; KDELR2; EIF2AK3; S100A16; ADAM9; TMED3; MIA3; SURF4; and TXNDC11.

38. The method, composition, or combination of any of paragraphs 32-37, wherein the one or more genes of Table 11 and/or at least one or more genes of Table 12 comprise GALE; SEC61A1; KDELR2; EIF2AK3; S100A16; ADAM9; TMED3; MIA3; SURF4; and TXNDC11.

39. The method, composition, or combination of any of paragraphs 32-38, wherein the one or more genes of Table 11 and/or at least one or more genes of Table 12 comprise EIF2AK3; S100A16; ADAM9; TMED3; MIA3; SURF4; and TXNDC11.

40. The method, composition, or combination of any of paragraphs 32-39, wherein the one or more genes of Table 11 and/or at least one or more genes of Table 12 comprise EIF2AK3; S100A16; ADAM9; MIA3; SURF4; and TXNDC11.

41. The method, composition, or combination of any of paragraphs 32-40, wherein the level of expression of one or more of NSUN7; LOC100128816; MTHFD2; KDELR2; SLC44A3; SLC16A9; TMED3; TSPAN13; SEC61A1; and FAM177B are not determined.

42. The method, composition, or combination of any of paragraphs 32-41, wherein the level of expression of one or both of ENO4 and CREB3L1 are not determined.

43. The method, composition, or combination of any of paragraphs 32-42, wherein the expression of no more than 400 genes is determined.

44. The method, composition, or combination of any of paragraphs 32-43, wherein the expression of no more than 200 genes is determined.

45. The method, composition, or combination of any of paragraphs 32-44, wherein the expression of no more than 100 genes is determined.

46. The method, composition, or combination of any of paragraphs 32-45, wherein an increased or decreased level is the level relative to a patient who has never been a smoker.

47. The method, composition, or combination of any of paragraphs 32-46, wherein an increased or decreased level is the level relative to an age-matched patient who has never been a smoker.

48. The method, composition, or combination of any of paragraphs 32-47, wherein the level is the level in a bronchial brushing, bronchial biopsy, bronchial epithelium, airway epithelium, nasal brushing, and/or nasal epithelium.

49. The method, composition, or combination of any of paragraphs 32-48, wherein the level is the level in the nasal epithelium.

50. The method, composition, or combination of any of paragraphs 32-49, wherein the subject is a current or former tobacco smoker.

51. The method, composition, or combination of any of paragraphs 32-50, wherein the subject has been exposed to asbestos, air pollution, or environmental hazards.

52. The method, composition, or combination of paragraph 51, wherein the environmental hazard is dust, chemicals, fire, or smoke.

53. The method, composition, or combination of any of paragraphs 32-52, wherein the subject has or is diagnosed as having COPD.

54. The method, composition, or combination of any of paragraphs 32-53, wherein the subject is a mammal.

55. The method, composition, or combination of any of paragraphs 32-54, wherein the subject is a human.

56. The method, composition, or combination of any of paragraphs 32-55, wherein the human subject is at least 49 years old.

57. The method, composition, or combination of any of paragraphs 32-56, wherein the human subject is at least 58 years old.

58. The method, composition, or combination of any of paragraphs 32-57, wherein the subject has a GOLD grade of 2 or lower.

59. The method, composition, or combination of any of paragraphs 32-58, wherein the inhaled long-acting anti-muscarinic is selected from the group consisting of: tiotropium; ipratropium; umiclinidium; aclidinium; and diphenhydramine.

60. The method, composition, or combination of any of paragraphs 32-59, wherein the inhaled long-acting β2 agonist is selected from the group consisting of: fomoterol; salmeterol; arformoterol; bambuterol; clenbuterol abediterol; carmoterol; olodaterol; indacaterol; and vlianterol.

61. The method, composition, or combination of any of paragraphs 32-60, wherein the inhaled corticosteroid is selected from the group consisting of: budesonide; fluticasone; flunisolide; triamcinolone acetonide; beclomethasone dipropionate; mometasone furoate; and ciclesonide.

62. The method, composition, or combination of any of paragraphs 32-61, wherein the inhaled short-acting β2 agonist is selected from the group consisting of: albuterol; bitolterol; fenoterol; isoprenaline; isoproterenol; levosalbutamol; levalbuterol; orciprenaline; metaproterenol; pirbuterol; procaterol; ritodrine; salbutamol; and terbutaline.

63. The method, composition, or combination of any of paragraphs 32-62, wherein the treatment administered to a subject determined to have an increased level of expression of one or more genes of Table 11 and/or a decreased level of expression of one or more genes of Table 12 further comprises administration of an inhibitor of one or more genes of Table 11 and/or an agonist of one or more genes of Table 12.

Some embodiments of the technology described herein can be defined according to any of the following numbered paragraphs:
1. A method of treating chronic obstructive pulmonary disease (COPD), the method comprising:
   a. administering one or more of:
      an inhaled long acting antimuscarinic; an inhaled long-acting β2 agonist; and an inhaled corticosteroid;
      to a subject determined to have an increased level of expression of one or more genes of Table 11 or a decreased level of expression of one or more genes of Table 12; and
   b. administering one or more of intensive smoking cessation therapy and an inhaled short-acting β2 agonist to a subject determined not to have an increased level of expression of one or more genes of Table 11 or a decreased level of expression of one or more genes of Table 12.
2. The method of paragraph 1, wherein the one or more genes of Table 11 or one or more genes of Table 12 comprise at least one of GALE; SEC61A1; KDELR2; EIF2AK3; S100A16; ADAM9; TMED3; MIA3; SURF4; and TXNDC11.
3. The method of paragraph 1, wherein the one or more genes of Table 11 or one or more genes of Table 12 comprise GALE; SEC61A1; KDELR2; EIF2AK3; S100A16; ADAM9; TMED3; MIA3; SURF4; and TXNDC11.
4. The method of paragraph 1, wherein the one or more genes of Table 11 or one or more genes of Table 12 comprise EIF2AK3; S100A16; ADAM9; TMED3; MIA3; SURF4; and TXNDC11.
5. The method of paragraph 1, wherein the one or more genes of Table 11 or one or more genes of Table 12 comprise EIF2AK3; S100A16; ADAM9; MIA3; SURF4; and TXNDC11.
6. The method of paragraph 1, wherein the level of expression of one or more of NSUN7; LOC100128816; MTHFD2; KDELR2; SLC44A3; SLC16A9; TMED3; TSPAN13; SEC61A1; and FAM177B are not determined.
7. The method of paragraph 1, wherein the level of expression of one or both of ENO4 and CREB3L1 are not determined.
8. The method of paragraph 1, wherein the expression of no more than 400 genes is determined.
9. The method of paragraph 1, wherein an increased or decreased level is the level relative to a patient who has never been a smoker or an age-matched patient who has never been a smoker.
10. The method of paragraph 1, wherein the level is the level in a bronchial brushing, bronchial biopsy, bronchial epithelium, airway epithelium, nasal brushing, or nasal epithelium.
11. The method of paragraph 1, wherein the level is the level in the nasal epithelium.
12. The method of paragraph 1, wherein the subject is a current or former tobacco smoker.
13. The method of paragraph 1, wherein the subject is a human.
14. The method of paragraph 13, wherein the human subject is at least 49 years old.
15. The method of paragraph 13, wherein the human subject is at least 58 years old.
16. The method of paragraph 1, wherein the subject has a GOLD grade of 2 or lower.
17. The method of paragraph 1, wherein the inhaled long-acting antimuscarinic is selected from the group consisting of: tiotropium; ipratropium; umiclinidium; aclidinium; and diphenhydramine.
18. The method of paragraph 1, wherein the inhaled long-acting β2 agonist is selected from the group consisting of: fomoterol; salmeterol; arformoterol; bambuterol; clenbuterol abediterol; carmoterol; olodaterol; indacaterol; and vlianterol.
19. The method of paragraph 1, wherein the inhaled corticosteroid is selected from the group consisting of: budesonide; fluticasone; flunisolide; triamcinolone acetonide; beclomethasone dipropionate; mometasone furoate; and ciclesonide.
20. The method of paragraph 1, wherein the inhaled short-acting β2 agonist is selected from the group consisting of: albuterol; bitolterol; fenoterol; isoprenaline; isoproterenol; levosalbutamol; levalbuterol; orciprenaline; metaproterenol; pirbuterol; procaterol; ritodrine; salbutamol; and terbutaline.
21. The method of paragraph 1, wherein the treatment administered to a subject determined to have an increased level of expression of one or more genes of Table 11 or a decreased level of expression of one or more genes of Table 12 further comprises administration of an inhibitor of one or more genes of Table 11 or an agonist of one or more genes of Table 12.
22. A method of treating COPD comprising administering at least one of: an inhibitor of one or more genes of Table 11 or an agonist of one or more genes of Table 12.
23. The method of paragraph 22, wherein the subject is determined to have an increased level of expression of one or more genes of Table 11 or a decreased level of expression of one or more genes of Table 12.
24. The method of paragraph 22, wherein the administering step comprises the administration of a vector comprising a nucleic acid encoding the agonist or inhibitor.
25. A method comprising determining the level of expression of one or more genes of Table 11 and Table 12 in a sample obtained from a subject, wherein the sample is a bronchial brushing, bronchial biopsy, bronchial epithelium sample, airway epithelium sample, nasal brushing, or nasal epithelium sample.

EXAMPLES

Example 1: A Bronchial Gene Expression Signature Associated with Rate of Subsequent FEV1 Decline A bronchial airway gene expression profile that is associated with the rate of subsequent lung function decline has been developed and validated. Profiling for the diagnostic test is accomplished using microarrays, RNA sequencing and other methods. This diagnostic assessment permits identification of individuals with incipient COPD prior to the loss of substantial lung function. The invention provides for a diagnostic assessment with a window of opportunity so that early therapy could effectively lead to COPD interception. The gene expression signature also predicts the rate of lung function decline that will occur after the signature is measured, so it also reflects the underlying disease process that contributes to lung function decline. In other embodiments of the invention, the gene expression profiling test is a screening tool to identify promising new drug candidates (e.g. compounds that cause normalization of the gene signature), to monitor the efficacy of drug treatment, and to stratify patients for clinical trials.

Background Chronic Obstructive Pulmonary Disease (COPD) is characterized by progressive lung function decline. Leveraging prior work demonstrating bronchial airway gene-expression alterations associated with COPD, the inventors sought to determine if there are alterations associated with differences in the rate of $FEV_1$ decline.

Methods The inventors examined gene-expression among ever smokers with and without COPD who at baseline had bronchial brushings profiled by Affymetrix microarrays and had longitudinal lung function measurements (n=134; mean follow-up=6.38+/−2.48 years). Gene-expression profiles associated with the rate of $FEV_1$ decline were identified by linear modeling.

Results Expression differences in 171 genes were associated with rate of $FEV_1$ decline (FDR<0.05). The $FEV_1$-decline signature was replicated in an independent dataset of bronchial biopsies from COPD patients (n=46; p=0.018; mean follow-up=6.76+/−1.32 years). Genes elevated in individuals with more rapid $FEV_1$ decline are significantly enriched among the genes altered by modulation of XBP1 in two independent datasets (GSEA p<0.05).

Discussion The inventors have identified and replicated an airway gene expression signature associated with the rate of $FEV_1$ decline. Aspects of this signature are related to increased expression of XBP1-regulated genes, a transcription factor involved in the unfolded protein response. Collectively, these data indicate that molecular processes related to the rate of $FEV_1$ decline can be detected in airway epithelium, identify an indicator of $FEV_1$ decline, and make it possible to detect, in an early phase, ever smokers with and without COPD most at risk of rapid $FEV_1$ decline.

Demonstrated herein is an airway epithelium gene expression signature associated with the rate of subsequent decline in $FEV_1$. This signature is enriched for genes that are regulated by XBP1, a key transcription factor involved in the unfolded protein response. The present study highlights that molecular processes associated with the rate of $FEV_1$ decline can be detected by bronchial epithelial gene expression profiles. This work identifies an indicator of FEV1 decline and demonstrates the ability of bronchial gene expression to serve as an intermediate endpoint for studying the rate of $FEV_1$ decline.

Introduction

Chronic Obstructive Pulmonary Disease (COPD) is the third leading cause of death in the world.[1] In 2016, 3 million people died of COPD, which accounted for 6% of all deaths globally.[1] Patients with COPD experience lung function decline over time, most commonly measured by change in the forced expiratory volume in one second (FEV1). Lower FEV1 is associated with an increased risk of death,[2] and even smokers who do not yet meet the clinical definition of COPD may experience more rapid FEV1 decline.[3] The rate of FEV1 decline is highly variable between individuals.[4] Though some risk factors for rapid FEV1 decline have been identified, such as cigarette smoking,[5] higher blood neutrophil counts,[6] albuminuria,[7] and Alpha 1-antitrypsin deficiency,[8] these do not fully explain the heterogeneity in COPD, and have not yet been useful in predicting FEV1 decline for individual patients. The ability to predict $FEV_1$ decline would permit clinicians to stratify at-risk patients towards more aggressive management. It can also facilitate clinical trials of therapies to modify the natural history of COPD, specifically targeting individuals more likely to experience greater decline in FEV1. Finally, it can lead to further indications for finding therapeutic targets to slow disease progression.

Previous studies have demonstrated that bronchial epithelial gene expression is altered both by cigarette smoking and in diseases associated with cigarette smoking.[9-11] A bronchial airway gene expression signature of COPD and disease severity as measured by $FEV_1$ has been described [10] Provided herein are the identification and replication of a baseline gene expression signature associated with the rate of FEV1 decline observed during subsequent follow up. This signature is significantly enriched for genes with binding sites for the transcription factor encoded by XBP1, which is involved in the unfolded protein response to endoplasmic reticulum stress.

Methods

Primary Dataset and Longitudinal FEV1

The individuals included in this study were recruited as part of the British Columbia Lung Health Study (n=267).[16] Additional information about recruitment can be found in Example 2. Bronchial airway brushings obtained from current and former smokers were profiled using Affymetrix Human Gene 1.0 ST Arrays and these data have been previously published.[10] In the current study, we used this gene expression data together with spirometry data that was collected during longitudinal follow up subsequent to the bronchoscopy. $FEV_1$, $FEV_1$% predicted, and FVC were measured using a flow-sensitive spirometer. The ratio between $FEV_1$ and FVC were used to determine COPD status as previously described in Steiling et al. [10] Samples from individuals who did not have a spirometry recording within one year of their bronchoscopy (n=8), did not have at least two spirometry measurements at least four years apart (n=104), or that developed cancer (n=19) were excluded. As previously reported, two samples were excluded due to sample labeling errors[10]. Data from the remaining 134 current and former smokers were included in the analysis. The rate of FEV1 decline ($\Delta FEV_1$) for a study participant was estimated using linear regression with all available spirometry measurements from that individual subsequent bronchoscopy. The relationship between the rate of FEV1 decline and other clinical variables was evaluated by ANOVA of linear models.

Identification of a Rate of FEV1 Decline Gene-Expression Signature

Genes associated with the future rate of FEV1 decline were identified using the following linear models calculated using the lm function and the anova function using R statistical software version 3.4.0[17] and RStudio version 1.0.143.[18]

$$ge \sim \beta_0 + \beta_1 X_{age} + \beta_2 X_{Smoke\_Status} + \beta_3 X_{pack\_years} + \beta_4 X_{Sex} + \beta_5 X_{baseline\_FEV1} + \varepsilon \quad (1)$$

$$ge \sim \beta_0 + \beta_1 X_{age} + \beta_2 X_{Smoke\_Status} + \beta_3 X_{pack\_years} + \beta_4 X_{Sex} + \beta_5 X_{baseline\_FEV1} + \beta_6 X_{\Delta FEV1} + \varepsilon \quad (2)$$

where ge is the expression level of a single gene; age is the age at the time of bronchoscopy, pack years is the calculated cumulative cigarette smoke exposure at the time of bronchoscopy, and smoke status is the smoking status at the time of bronchoscopy (participants were considered former smokers if they had quit for at least a year). Baseline $FEV_1$ is the $FEV_1$ within one year of bronchoscopy. The rate of FEV1 decline ($\Delta FEV_1$) is calculated as described above. $\varepsilon$ is an error term. The False Discovery Rate (FDR) was calculated from the ANOVA p-values.[19] Genes with FDR<0.05 were considered to be associated with the rate of FEV1 decline and included in the signature. The signature was divided into genes that are increased or decreased with more rapid FEV1 decline by hierarchical clustering. The rate of FEV1 decline signature was compared to a previously published airway gene expression signature of COPD severity by determining the number of genes overlapping between the signatures, and by using Gene Set Enrichment Analysis (GSEA).[20]

Replication of the Gene Expression Signature of Rate of $FEV_1$ Decline in GLUCOLD The inventors investigated the association between the expression of genes in the rate of FEV1 decline signature and the observed rate of FEV1 decline in a previously published independent dataset of individuals with COPD who were enrolled in the GLUCOLD trial, a placebo controlled randomized double blind clinical trial of fluticasone with or without salmeterol[21,22] (GSE36221). Briefly, these participants underwent bronchoscopy with endobronchial biopsy followed by spirometry every three months during the 2.5-year trial. After the 2.5-year drug treatment trial, participants performed spirometry every year up to a total of 7.5 years (mean=6.91). The rate of FEV1 decline was estimated by the coefficient from a linear model for each individual using their baseline spirometry measurement (t=year 0), excluding their time on treatment (t=0.25 to t=2.5 years) and including measurements from 3.5 years forward, to control for treatment effect. In the GLUCOLD participants, the gene expression signature associated with subsequent FEV1 decline was calculated using principal components analysis. First, the eigenvector for the first principal component of the signature genes in the z-score normalized discovery set was calculated using the prcomp function in R. A summarized signature score for each sample in the discovery set and the GLUCOLD dataset was then calculated from the eigenvector and the z-score normalized expression data using the predict method of prcomp. The relationship between summarized signature score at baseline and the rate of FEV1 decline was evaluated using the linear model and anova strategy outlined above for the gene expression analysis.

Identification of Enriched Biologic Pathways

To identify transcription factors enriched in the $FEV_1$ decline signature we used the Molecular Signature Database (MSigDB)[20] to search computationally derived datasets of transcription factor binding sites. We divided the genes into two clusters when searching: genes that increase with worse FEV1 decline and genes that decrease with worse FEV1 decline. For each cluster of genes, we identified transcription factor binding sites for each gene cluster with an FDR<0.05. The transcription factor binding sites were based on Xie et al's work[23] and TRANSFAC v7.4.

The transcription factor XBP1, which was identified by the above method, was selected for in silico validation because it has previously been implicated in COPD[24] and because it is a well-studied transcription factor with several publicly available knockout out and overexpression datasets. The Gene Expression Omnibus (GEO) was searched using the key terms "XBP1 knock out" and "XBP1 overexpression" to identify potentially useful datasets. This identified 38 datasets.

After searching GEO to identify publicly available datasets investigating the gene expression effects of modulating XBP1 activity, we identified two datasets which we explored further: a dataset examining the effects of XBP1 overexpression in mouse adipocytes (GSE46178)[25] and a dataset examining the effects of XBP1 knockout in mouse hepatocytes (GSE64824).[26] Using t-statistics from a linear model, we ranked genes by their change in expression following XBP1 overexpression in mouse adipocytes (n controls=4, n overexpression=4) using data from Affymetrix Mouse Genome 430A 2.0 Arrays. For the XBP1 knockout study, we ranked genes according to their change in expression between WT and XBP1 knockout hepatocytes by subtracting the gene expression of the controls (n=2) from the knockout hepatocytes (n=2) which had been profiled by RNAseq using an Illumina HiSeq2000.[26] Before sequencing, the replicates were pooled. We explored the distribution of the two gene clusters from the rate of $FEV_1$ decline signature in these ranked lists using GSEA.[20]

A potential association between the $FEV_1$ decline signature and TH2 was investigated using a previously developed three gene TH2 signature developed in asthma patients[27]. The three genes, POSTN, SERPINB2, and CLCA1, were z-scored in the patient and then the first principle component was computed. An association between this TH2 score and lung function decline was tested using a linear model controlling for age, sex, smoking status, pack years, and baseline $FEV_1$. We also tested the association between the first principle component of the FEV1 decline signature and the TH2 score.

Results

Figure 5:
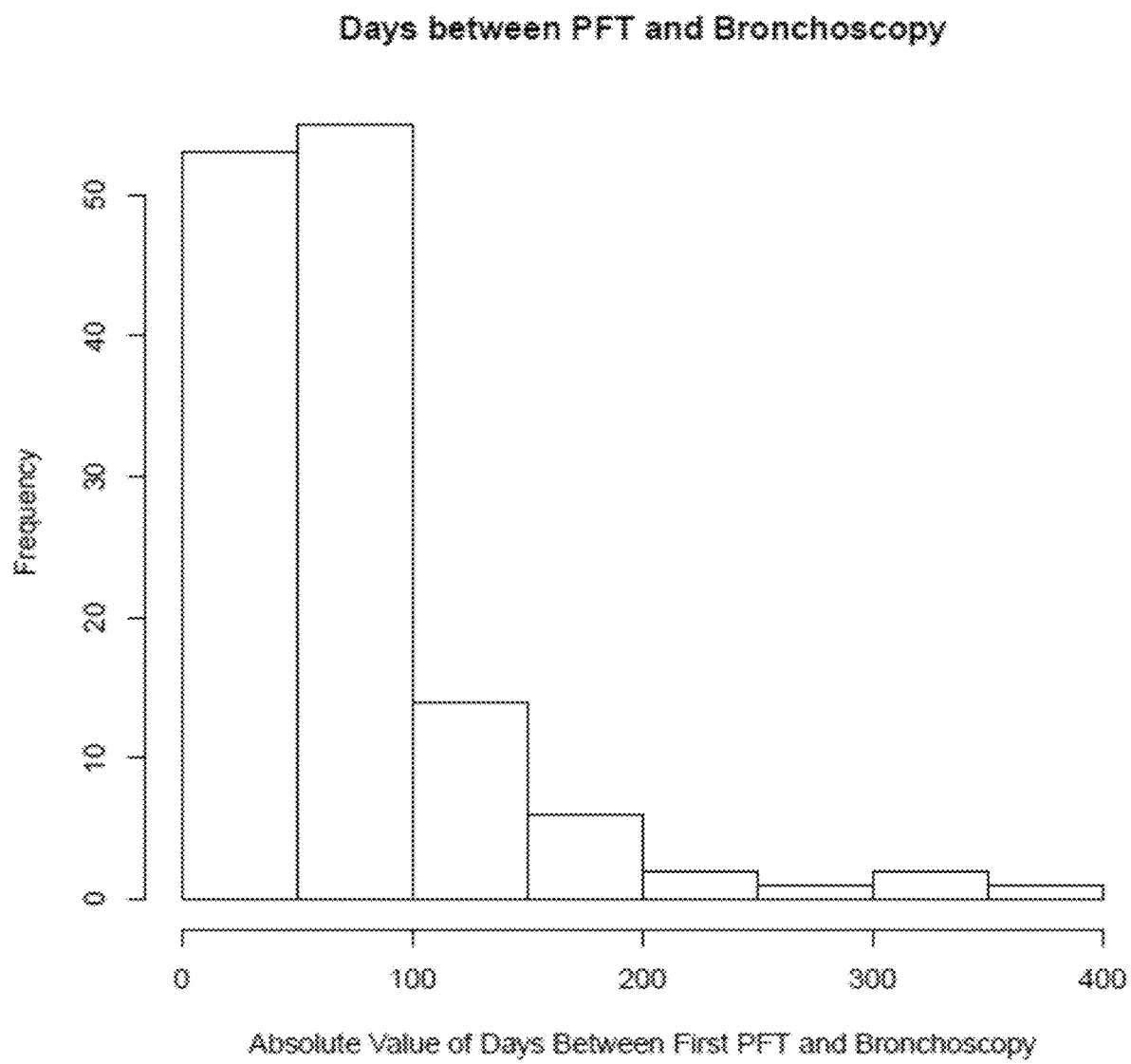
FIG. 5 depicts a histogram of the days between baseline spirometry measurement and bronchoscopy. For the majority of patients, their baseline spirometry measurement was within 100 days of the bronchoscopy.

Participant demographics. A total of 134 current and former smokers with (n=49) and without COPD (n=85) were included in this analysis. The average baseline FEV1 for participants with COPD was significantly lower than in participants without COPD. The rate of $FEV_1$ decline is significantly higher in individuals with lower baseline $FEV_1$ and/or COPD (p<0.05) (Table 2) Clinical and demographic characteristics of the study cohort are provided in 2 and 3. Demographic characteristics separated by GOLD status are available in Table 4. The initial spirometry measurements were performed within a year and the majority (70%) were performed within 90 days of the bronchoscopy (FIG. 5, Table 5).

TABLE 1

Characteristics of the study participants. All participants were current or former smokers. All participants had at least two spirometry measurements at least four years apart. The mean, standard deviation and range are reported for continuous measures.

| | N = 134 |
|---|---|
| Age | 64 +/− 6 (49.33-77.17) years |
| Pack years | 46 +/− 16 (12-102) (missing 8) |
| Smoking Status | 59 Current, 75 Former |
| Sex | 75M/59F |
| Inhaled medications | 20 yes, 114 no |
| COPD Status | 49 yes, 85 no |
| Baseline $FEV_1$ | 2.48 +/− 0.78 (0.95-4.52) L |
| $\Delta FEV_1$ | −33.72 +/− 47.78 (−170 to 170) mL/year |
| Follow up time | 6.38+/− 2.48 (4.08-12.64) years |

Bronchial Airway Gene Expression Signature of $FEV_1$ Rate of Decline. The expression levels of 171 genes were significantly associated with the rate $FEV_1$ decline (FDR<0.05) (FIG. 1 and Table 6). 120 genes had higher expression in individuals with faster $FEV_1$ decline (Cluster 1); while 51 genes had lower expression in individuals with faster $FEV_1$ decline (Cluster 2). This same set of genes were also identified when the linear model was repeated including individuals who had only 2 years or 3 years between their spirometry measurements. We next sought to determine whether there was a relationship between the longitudinal $FEV_1$ decline signature and a 98 bronchial gene expression signature of COPD severity we had previously identified in a cross-sectional analysis.[10] First, we evaluated the overlapping genes in these two signatures. A total of 10 genes were shared by the two signatures. Nine genes that were increased in association with worse FEV1 decline were also increased in COPD. One gene that was decreased with more rapid FEV1 decline was also decreased in COPD airway. Next, GSEA was also used to evaluate for enrichment between these signatures. There was significant concordant enrichment of the 171 gene signature associated with rate of $FEV_1$ decline and COPD status ranked list (positive FDR q<0.0001, negative FDR q<0.0001).

Figure 2A:
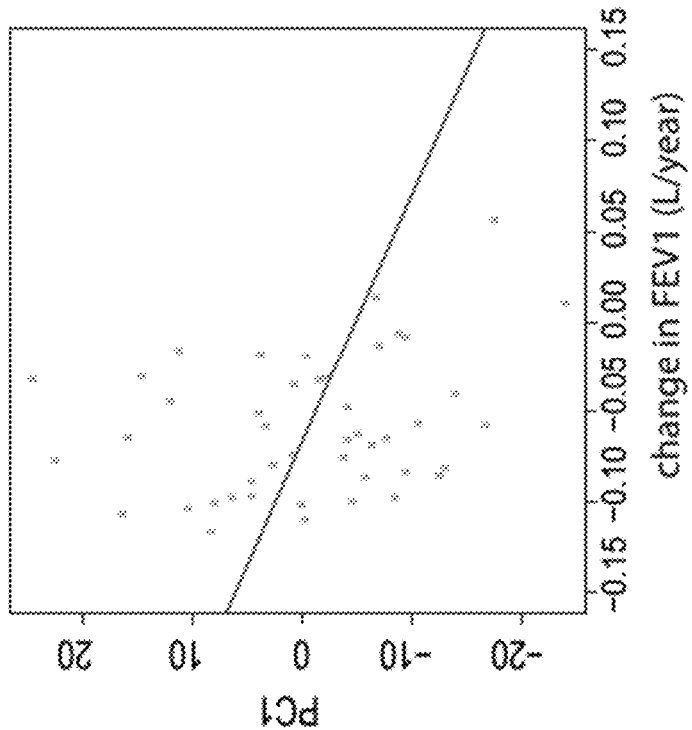
FIGS. 2A-2B depict graphs demonstrating that airway gene expression signature associated with rate of $FEV_1$ decline replicates in an independent dataset of COPD patients. The expression levels of the 171 genes associated with FEV1 decline were summarized into a single value using the eigenvector for the first principal component in the discovery dataset. This eigenvector was also used to generate signature summary values in an independent dataset of gene expression from baseline bronchial biopsies of COPD patients who were followed for subsequent change in $FEV_1$. The signature scores in the discovery dataset (FIG. 2A) and the independent dataset (FIG. 2B) are each significantly correlated with the rate of $FEV_1$ decline (p=0.000045 and p=0.018, respectively).
Figure 2B:
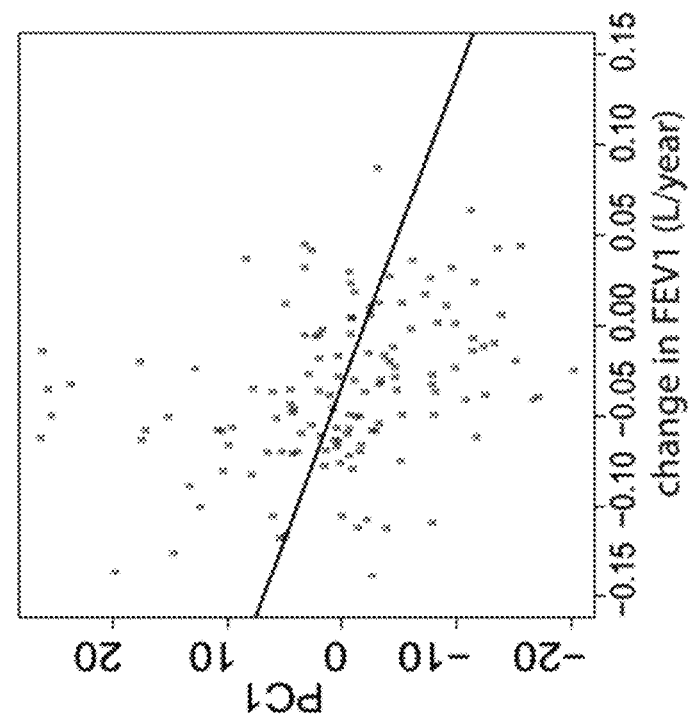

Replication of the Airway Gene Expression Signature of Rate of $FEV_1$ Decline in the GLUCOLD trial. We next sought to determine whether the rate of FEV1 decline signature is significantly associated with rate of $FEV_1$ change in an independent dataset using principal component analysis to generate a signature score. In the discovery dataset, higher signature scores are associated with a more rapid decrease in $FEV_1$ (p=0.000045; FIG. 2A). Signature scores generated in an independent dataset of individuals with COPD that were enrolled in a placebo controlled study of inhaled fluticasone+/−salmeterol[21] showed that the scores are significantly associated with future FEV1 decline in the independent dataset (p=0.018; FIG. 2B). Demographic information of the independent dataset is available in Table 4. These findings indicate that the airway gene expression signature for the rate of decline in $FEV_1$ is similarly associated with rate of $FEV_1$ decline in an independent dataset of participants with COPD.

Enrichment of Transcription Factor Binding Sites in the $FEV_1$ Rate of Decline Signature. To explore the potential regulators of the genes associated with the rate of $FEV_1$ decline, we queried MSigDB to identify transcription factors whose predicted binding sites are overrepresented among the signature genes. Genes whose expression levels are increased in individuals with more rapid FEV1 decline are enriched for genes with binding sites for ATF6 (FDR q=0.0325) and XBP1 (FDR q=0.0302) among other transcription factors. A full list of all the MSigDB results can be found in Tables 9 and 10.

We further investigated XBP1 due to its role in the unfolded protein response which has been shown to be involved in COPD[24] and because there are several useful publically available datasets investigating it. Using GEO, we identified a dataset examining the effect of XBP1 overexpression in mouse adipocytes (GSE46178)[25] and a dataset examining the effect of XBP1 knockout in mouse hepatocytes (GSE64824)[26] that we used in further analysis. These datasets were selected in part due to the lack of lung or epithelial cell XBP1 knockout or overexpression datasets. Additionally, prior studies have shown utility in using gene expression profiles of pertubragens [28] to identify novel therapies for emphysema [29].

Figure 3A:
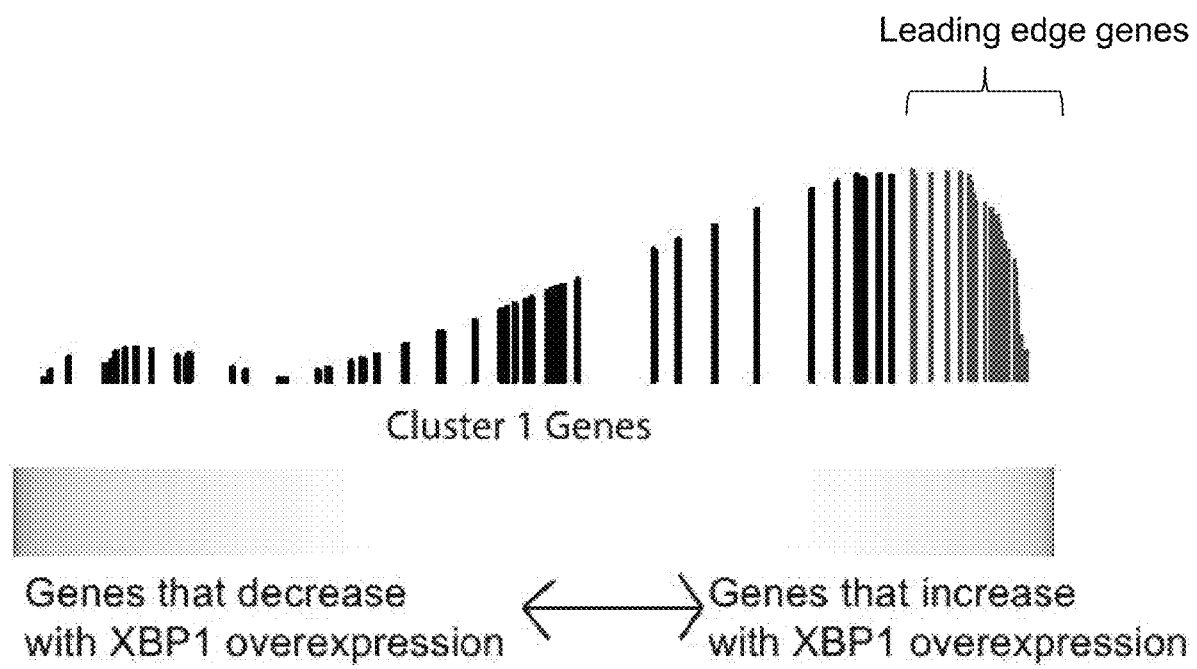
FIGS. 3A-3C demonstrate that genes increasing with faster $FEV_1$ decline are among the genes most induced by XBP1 overexpression.
Figure 3B:
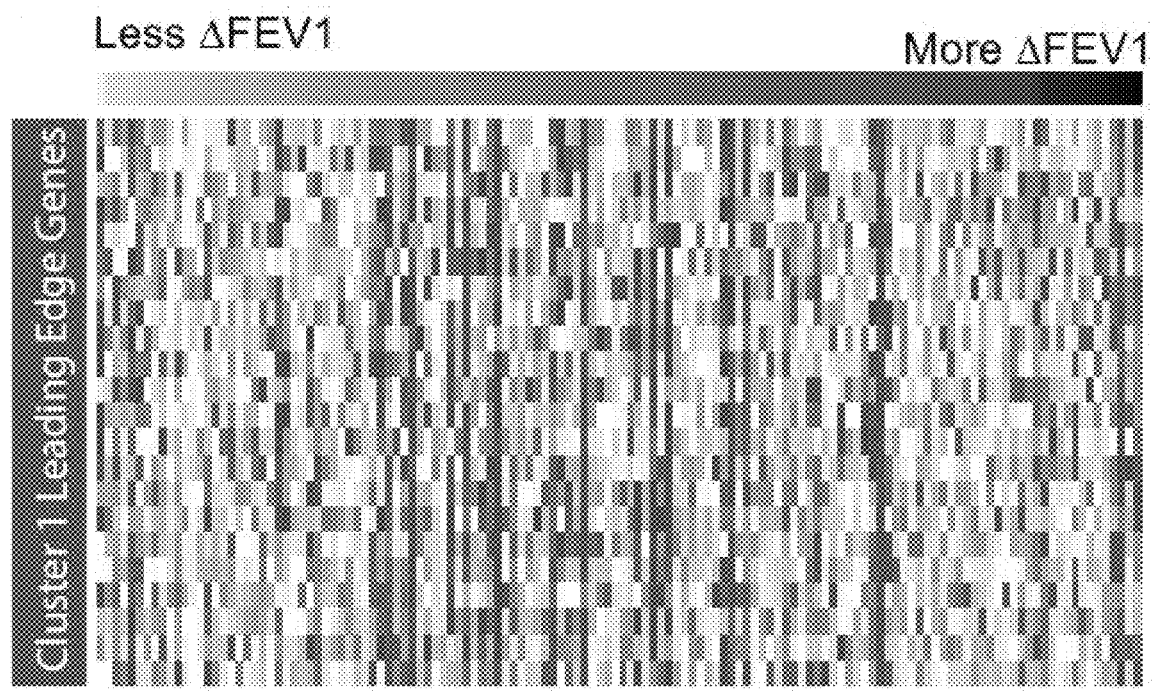
Figure 3C:
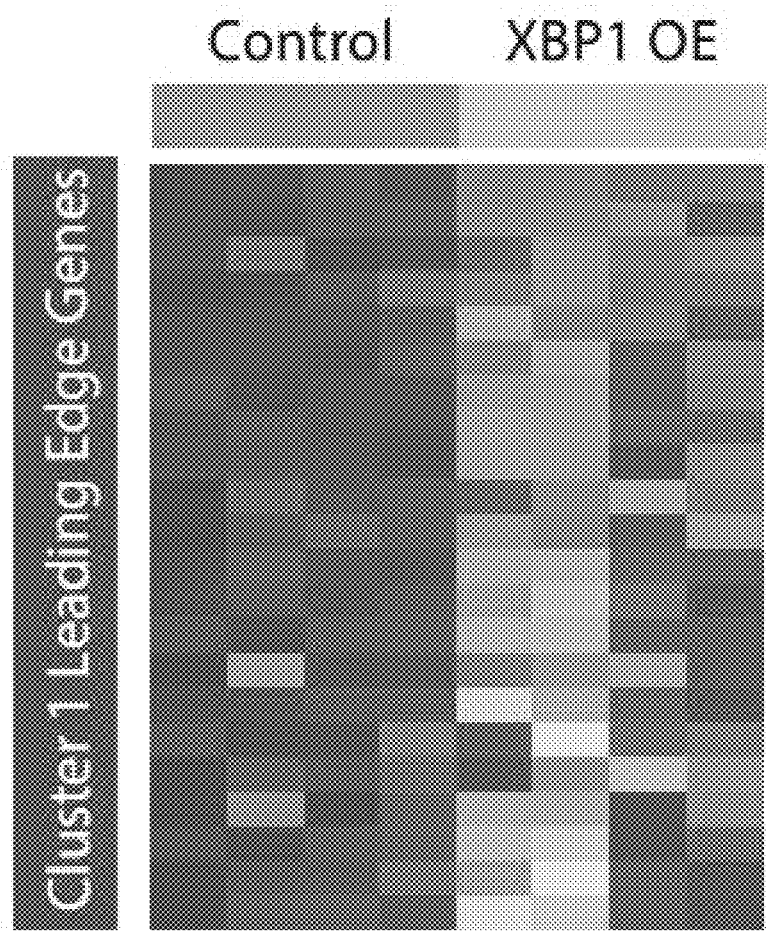

We ranked the genes that change with XBP1 overexpression in mouse adipocytes (n=4 controls, n=4 XBP1 overexpression) and used GSEA to examine the distribution of genes in the FEV1 decline signature in this ranked list. Genes whose expression is increased in individuals with more rapid decline in FEV1 are enriched among the genes that are induced by XBP1 overexpression (p<0.001) (FIGS. 3A-3C). We next selected the subset of genes contributing the most to this significant enrichment, which are also known as the leading edge genes. We used these leading edge genes to plot a heatmap across the human bronchial airway gene expression data, and the mouse adipocyte data. The leading edge genes that increased with more rapid FEV1 decline were also increased with XBP1 overexpression (FIGS. 3B and 3C).

Figure 4A:
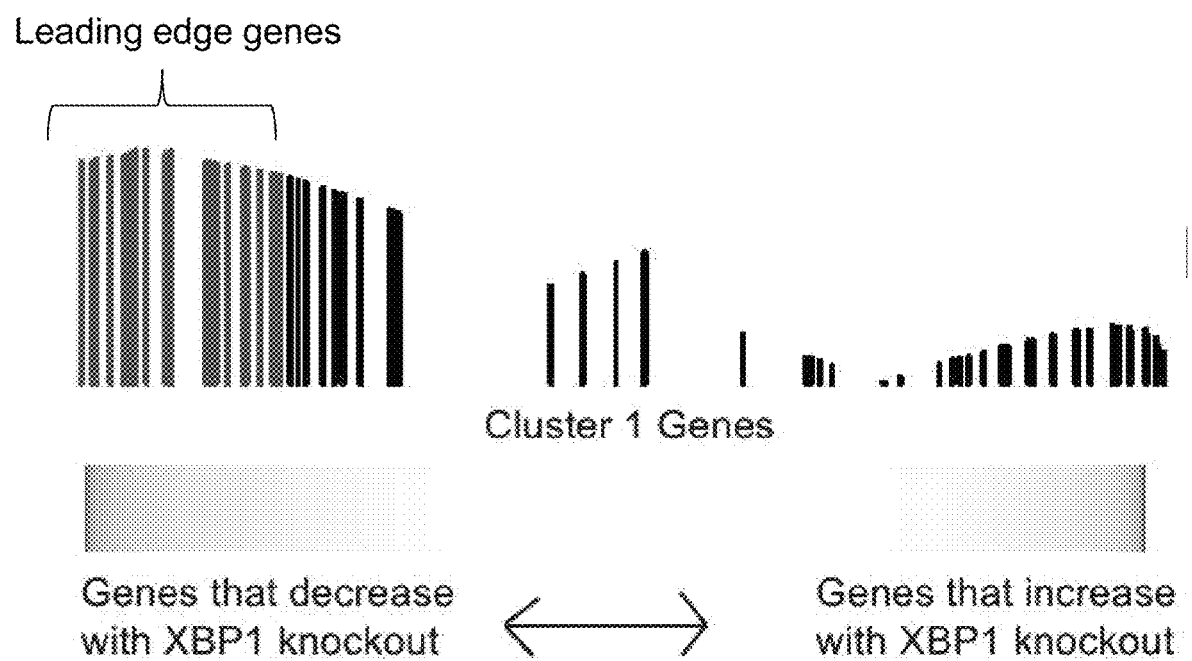
FIGS. 4A-4C demonstrate that genes increasing with faster $FEV_1$ decline are among the genes most decreased by XBP1 knockout.
Figure 4B:
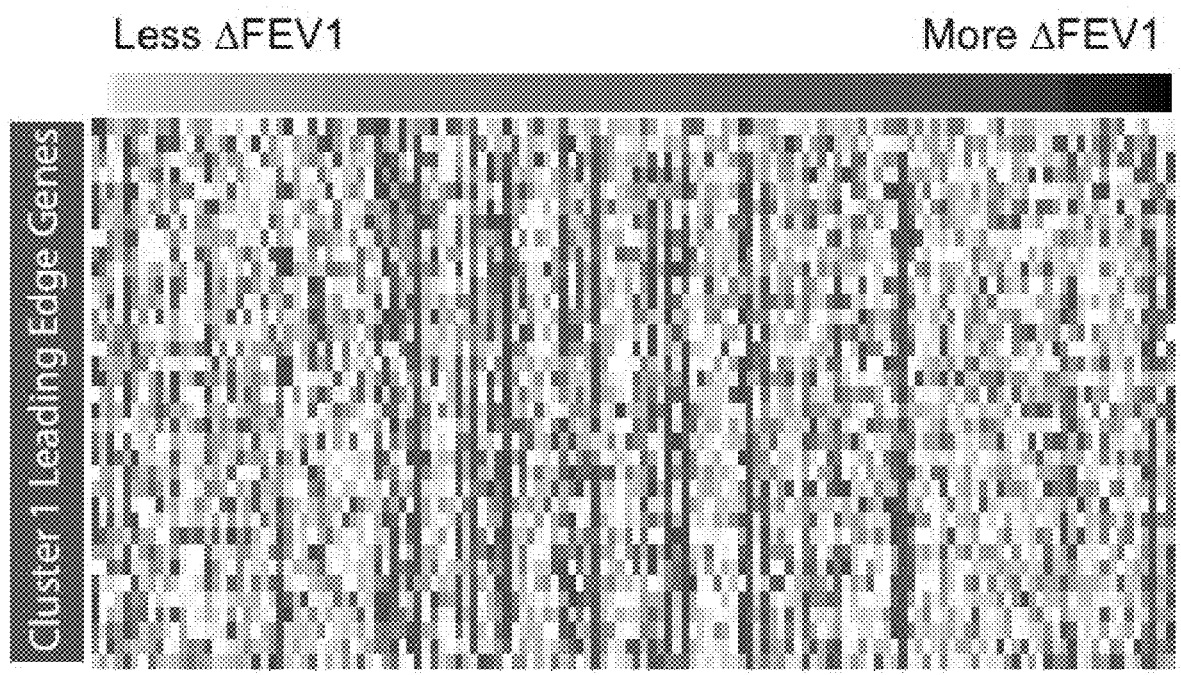
Figure 4C:

We also created a ranked list of genes based on expression changes in XBP1-knockout vs WT control hepatocytes from 16-week old mice (n=2 controls, n=2 XBP1 knockout).[26] Genes whose expression is increased in individuals with more rapid FEV1 decline are enriched among the genes that decreased in XBP1 knockout (p=0.025; FIGS. 4A-4C). There were 22 leading edge genes from the XBP1 overexpression analysis and 35 in the knockout analysis. Fifteen of these genes overlapped between the two sets. We also compared the leading edge genes to the signature genes that were in the XBP1 transcription binding site list (n=133). Of the four genes that overlap between the FEV1 decline signature and the XBP1 transcription factor binding site gene set, three of them were also in the leading edge of the analyses (GALE, SEC61A1, and ARMCX3). Together, these data indicate that XBP1-regulated genes are among the genes with increased expression in bronchial epithelial cells of individuals with more rapid $FEV_1$ decline.

Figure 6A:
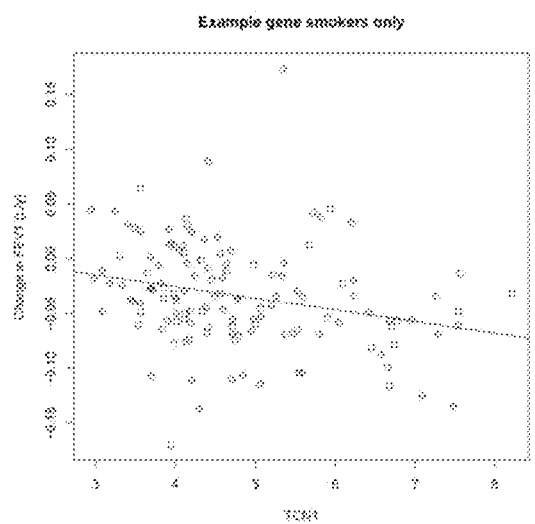
FIGS. 6A-6C depict example genes from the supplemental analysis. These genes were near the top of the ranked list of genes that increase in advance of $FEV_1$ decline in each subset of participants. There was a significant enrichment of the FEV1 decline signature in each ranked list.
Figure 6B:
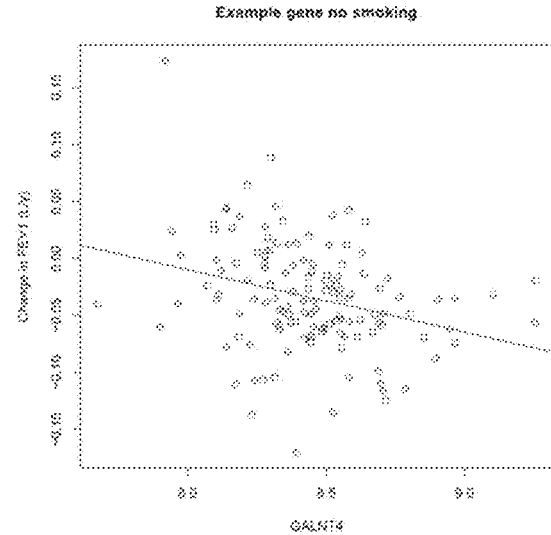
Figure 6C:
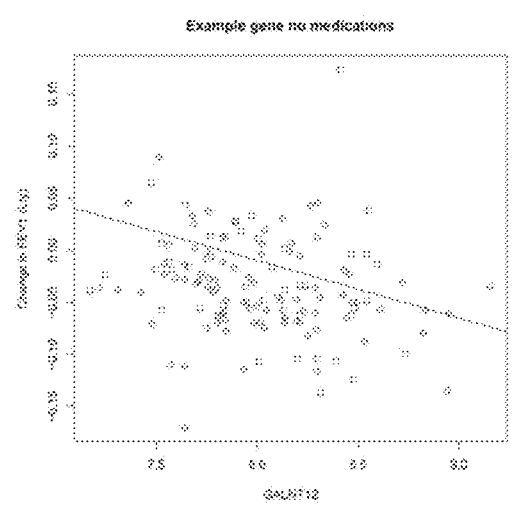

We identified an association between a TH2 score that had previously been developed in asthma patients[27], and change in $FEV_1$ when controlling for age, sex, smoking status, pack years, and baseline $FEV_1$ (p=0.045)(Tables 7 and 8, FIGS. 6A-6C).

DISCUSSION

We have identified gene expression differences at baseline in bronchial epithelium from current and former smokers that are associated with the subsequent rate of change in $FEV_1$. We have replicated the airway gene expression signature of $FEV_1$ decline in an independent dataset of participants with COPD. Interestingly, we find that a subset of the airway gene expression changes associated with more rapid $FEV_1$ decline may be in part explained by increased activity of the transcription factor XBP1.

The replication of the gene expression signature of $FEV_1$ decline in endobronchial biopsies from participants with COPD in the GLUCOLD trial is notable in two regards. First is the replication of the signature in a different sample type (bronchial biopsies vs. brushes). Second, as GLUCOLD is comprised of only COPD patients, replication in this cohort indicate that the signature can be relevant to COPD progression.

The relevance of the FEV1 decline signature is supported by the individual genes within it. TCN1, a gene we found to be increased with more rapid FEV1 decline has also been previously shown to be increased in peripheral blood in COPD patients who were admitted to the ICU for COPD exacerbation[30]. We also found GALNT4, GALNT5, and GALNT12 increased in expression in patients who undergo more rapid FEV1 decline. These genes are involved in the post-translational modification of mucin. They are also increased with elevated MUC5AC and are in general associated with mucus production.[31] Furthermore, we have identified MUC2 as increased in patients with more rapid decline in $FEV_1$, and MUC2 has previously been implicated in mucus hypersecretion.[32]

The transcription factor binding sites enriched in the rate of $FEV_1$ decline signature also support the biological plausibility of this signature. Notably, XBP1, which is involved in the unfolded protein response and whose targets are found to be increased in advance of FEV1 decline in our data, increases expression of cytokines in COPD even when controlled for smoking status. [33] This is the first study to our knowledge to identify XBP1 as a potential regulator of gene expression changes associated with the rate of $FEV_1$ decline. We have found that gene expression consequences of XBP1 perturbation in a cell line and a mouse model recapitulate components of the $FEV_1$ decline signature, supporting a potential regulatory role for XBP1 in the processes that contribute to the rate of FEV1 decline.

The data described here support that we have identified a replicable FEV1 decline gene expression signature of FEV1 decline possibly driven by XBP1. We have identified and replicated gene expression differences associated with the rate of subsequently observed FEV1 decline using baseline gene expression profiling of bronchoscopy brushings. It is also important to note that baseline FEV1 was controlled for in the linear model for the identification of this gene expression signature. The association between baseline $FEV_1$ and future decline has previously been observed, [42] so the genes identified here are a conservative set of genes. Such markers can be used to stratify patients with and at risk for COPD, and to evaluate the response to therapies aimed at diminishing the rate of $FEV_1$ decline.

CITATIONS

1. The top 10 causes of death. who.int/news-room/fact-sheets/detail/the-top-10-causes-of-death (accessed 6 Jun. 2019).
2. Mannino D M, Buist A S, Petty T L, et al. Lung function and mortality in the United States: data from the First National Health and Nutrition Examination Survey follow up study. Thorax 2003; 58:388-93. doi:10.1136/thorax.58.5.388
3. Anthonisen N R, Connett J E, Murray R P. Smoking and Lung Function of Lung Health Study Participants after 11 Years. Am J Respir Crit Care Med Published Online First: 20 Dec. 2012. doi:10.1164/rccm.2112096
4. Nishimura M, Makita H, Nagai K, et al. Annual Change in Pulmonary Function and Clinical Phenotype in Chronic Obstructive Pulmonary Disease. Am J Respir Crit Care Med 2012; 185:44-52. doi:10.1164/rccm.201106-0992OC
5. Scanlon P D, Connett J E, Waller L A, et al. Smoking Cessation and Lung Function in Mild-to-Moderate Chronic Obstructive Pulmonary Disease. Am J Respir Crit Care Med 2000; 161:381-90. doi:10.1164/ajrccm.161.2.9901044
6. Higashimoto Y, Iwata T, Okada M, et al. Serum biomarkers as predictors of lung function decline in chronic obstructive pulmonary disease. Respir Med 2009; 103:1231-8. doi:10.1016/j.rmed.2009.01.021
7. Oelsner E C, Balte P P, Grams M E, et al. Albuminuria, Lung Function Decline, and Risk of Incident Chronic Obstructive Pulmonary Disease. The NHLBI Pooled Cohorts Study. Am J Respir Crit Care Med 2018; 199:321-32. doi:10.1164/rccm.201803-0402OC
8. Esquinas C, Serreri S, Barrecheguren M, et al. Long-term evolution of lung function in individuals with alpha-1 antitrypsin deficiency from the Spanish registry (REDAAT). Int J Chron Obstruct Pulmon Dis 2018; 13:1001-7. doi:10.2147/COPD.S155226
9. Beane J, Vick J, Schembri F, et al. Characterizing the Impact of Smoking and Lung Cancer on the Airway Transcriptome Using RNA-Seq. Cancer Prev Res (Phila Pa.) 2011; 4:803-17. doi:10.1158/1940-6207.CAPR-11-0212
10. Steiling K, van den Berge M, Hijazi K, et al. A Dynamic Bronchial Airway Gene Expression Signature of Chronic Obstructive Pulmonary Disease and Lung Function Impairment. Am J Respir Crit Care Med 2013; 187:933-42. doi:10.1164/rccm.201208-1449OC
11. Perez-Rogers J F, Gerrein J, Anderlind C, et al. Shared Gene Expression Alterations in Nasal and Bronchial Epithelium for Lung Cancer Detection. JNCI J Natl Cancer Inst 2017; 109. doi:10.1093/jnci/djw327
12. Becker E J, Faiz A, Van Den Berge M, et al. A Bronchial Airway Gene Expression Signature of Future Lung Function Decline Is Enriched in XBP1-Regulated Genes. In: D107. MITOCHONDRIA AND ER STRESS IN HOMEOSTASIS AND REPAIR. American Thoracic Society 2019. A7234-A7234. doi:10.1164/ajrccm-conference.2019.199.1_MeetingAbstracts.A7234
13. Becker E J, Faiz A, Alekseyev O, et al. Derivation of a Bronchial Airway Gene Expression Signature Associated with FEV1 Decline. Am Thorac Soc Int Conf Meet Abstr; A7159-A7159.
14. Becker E J, Faiz A, Lenburg M, et al. A Bronchial Airway Gene Expression Signature Of Lung Function Decline. Am Thorac Soc Int Conf Meet Abstr 2017; A7036-A7036.
15. Becker E, Lam S, Berge M van den, et al. Predicting Lung Function Decline in COPD Using Bronchial Airway Gene Expression. CHEST 2016; 150:912A. doi:10.1016/j.chest.2016.08.1012
16. Tammemagi M C, Lam S C, McWilliams A M, et al. Incremental Value of Pulmonary Function and Sputum DNA Image Cytometry in Lung Cancer Risk Prediction. Cancer Prev Res (Phila Pa.) 2011; 4:552-61. doi:10.1158/1940-6207.CAPR-10-0183
17. R: Fitting Linear Models. stat.ethz.ch/R-manual/R-devel/library/stats/html/lm.html (accessed 1 Jun. 2017).
18. RStudio Team. RStudio: Integrated Development for R. Boston, MA: RStudio, Inc 2016. www.rstudio.com
19. Benjamini Y, Hochberg Y. Controlling the false discovery rate: a practical and powerful approach to multiple testing. J R Stat Soc 1995; 57:289-300.
20. Subramanian A, Tamayo P, Mootha V K, et al. Gene set enrichment analysis: A knowledge-based approach for interpreting genome-wide expression profiles. Proc Natl Acad Sci USA 2005; 102:15545-50.
21. Berge M van den, Steiling K, Timens W, et al. Airway gene expression in COPD is dynamic with inhaled corticosteroid treatment and reflects biological pathways associated with disease activity. Thorax 2013; thoraxjnl-2012-202878. doi:10.1136/thoraxjnl-2012-202878
22. Lapperre T S. Effect of Fluticasone With and Without Salmeterol on Pulmonary Outcomes in Chronic Obstructive Pulmonary Disease: A Randomized Trial. Ann Intern Med 2009; 151:517. doi:10.7326/0003-4819-151-8-200910200-00004
23. Xie X, Lu J, Kulbokas E J, et al. Systematic discovery of regulatory motifs in human promoters and 3' UTRs by comparison of several mammals. Nature 2005; 434:338-45. doi:10.1038/nature03441
24. Kelsen S G. The Unfolded Protein Response in Chronic Obstructive Pulmonary Disease. Ann Am Thorac Soc 2016; 13: S138-45. doi:10.1513/AnnalsATS.201506-320 KV
25. Gregor M F, Misch E S, Yang L, et al. The role of adipocyte XBP1 in metabolic regulation during lactation. Cell Rep 2013; 3:1430-9. doi:10.1016/j.celrep.2013.03.042
26. Liu X, Henkel A S, LeCuyer B E, et al. Hepatocyte X-box binding protein 1 deficiency increases liver injury in mice 27 Bhakta N R, Solberg O D, Nguyen C P, et al. A qPCR-based metric of Th2 airway inflammation in asthma. Clin Transl Allergy 2013; 3:24. doi:10.1186/2045-7022-3-24

28 GTEx Consortium, Aguet F, Brown A A, et al. Genetic effects on gene expression across human tissues. Nature 2017; 550:204.

29 Campbell J D, McDonough J E, Zeskind J E, et al. A gene expression signature of emphysema-related lung destruction and its reversal by the tripeptide GHK. Genome Med 2012; 4:67. doi:10.1186/gm367

30 Almansa R, Socias L, Sanchez-Garcia M, et al. Critical COPD respiratory illness is linked to increased transcriptomic activity of neutrophil proteases genes. BMC Res Notes 2012; 5:401. doi: 10.1186/1756-0500-5-401

31 Wang G, Xu Z, Wang R, et al. Genes associated with MUC5AC expression in small airway epithelium of human smokers and non-smokers. BMC Med Genomics 2012; 5:21. doi:10.1186/1755-8794-5-21

32 Gosens R, Zaagsma J, Meurs H, et al. Muscarinic receptor signaling in the pathophysiology of asthma and COPD. Respir Res 2006; 7:73. doi:10.1186/1465-9921-7-73

33 Martinon F, Chen X, Lee A-H, et al. TLR activation of the transcription factor XBP1 regulates innate immune responses in macrophages. Nat Immunol 2010; 11:411-8. doi:10.1038/ni.1857

34 Geraghty P, Baumlin N, Salathe M A, et al. Glutathione Peroxidase-1 Suppresses the Unfolded Protein Response upon Cigarette Smoke Exposure. Mediators Inflamm. 2016. doi:10.1155/2016/9461289

35 Chung K F. Cytokines in chronic obstructive pulmonary disease. Eur Respir J 2001; 18:50s-9s. doi:10.1183/09031936.01.00229701

36 Jorgensen E, Stinson A, Shan L, et al. Cigarette smoke induces endoplasmic reticulum stress and the unfolded protein response in normal and malignant human lung cells. BMC Cancer 2008; 8:229. doi: 10.1186/1471-2407-8-229

37 Min T, Bodas M, Mazur S, et al. Critical role of proteostasis-imbalance in pathogenesis of COPD and severe emphysema. J Mol Med Berl Ger 2011; 89:577-93. doi:10.1007/s00109-011-0732-8

38 Mimura N, Fulciniti M, Gorgun G, et al. Blockade of XBP1 splicing by inhibition of IRE1α is a promising therapeutic option in multiple myeloma. Blood 2012; 119:5772-81. doi:10.1182/blood-2011-07-366633

39 Overley-Adamson B, Artlett C M, Stephens C, et al. Targeting the unfolded protein response, XBP1, and the NLRP3 inflammasome in fibrosis and cancer. Cancer Biol Ther 2014; 15:452-62. doi:10.4161/cbt.27820

40 Molfino N A. Genetic predisposition to accelerated decline of lung function in COPD. Int J Chron Obstruct Pulmon Dis 2007; 2:117-9.

41 Lamb J, Crawford E D, Peck D, et al. The Connectivity Map: Using Gene-Expression Signatures to Connect Small Molecules, Genes, and Disease. Science 2006; 313:1929-35. doi:10.1126/science.1132939

42 Tashkin D P. Variations in FEV1 decline over time in chronic obstructive pulmonary disease and its implications. Curr Opin Pulm Med 2013; 19:116-124. doi: 10.1097/MCP.0b013e32835d8ea4

43 Boudewijn I M, Faiz A, Steiling K, et al. Nasal gene expression differentiates COPD from controls and overlaps bronchial gene expression. Respir Res 2017; 18. doi:10.1186/s12931-017-0696-5

Example 2

Methods: Recruitment

The full details of selection criteria can be found in a previously published paper by Tammemagi et al[1]. as part of the British Columbia Lung Health Study and Pan-Canadian Lung health Study (U01-CA-96109, NO1-CN-85188, NO1-CN65030 and P01 CA096964). As part of a prior cross-section study of airway gene expression in COPD, a total of 267 bronchial brushing samples were selected to ensure matching for covariates between individuals with and without COPD, and analyzed using Affymetrix Human Gene 1.0 ST Arrays [Steiling et al, AJRCCM 2013]. For this secondary analysis, we used the existing publicly available microarray data from the prior study (GSE37147). As in the prior study, we excluded individuals who developed lung cancer or who did not have spirometry measurements within one year of bronchoscopy. We restricted the secondary analysis to individuals with longitudinal spirometry measurements available as part of the parent study.

For this analysis, individuals who developed lung cancer were excluded, as well as those who did not have at least two spirometry measurements at least 4 years apart.

TABLE 2

The coefficients from a Pearson's correlation test between each variable.

|  | ΔFEV1 | age | sex | Smoking status | Pack Years | Baseline FEV1 | COPD status | Follow up time |
|---|---|---|---|---|---|---|---|---|
| ΔFEV1 | 1.0000 | −0.1196 | 0.0801 | 0.0124 | 0.0629 | −0.2997 | 0.1996 | 0.0859 |
| age | −0.1196 | 1.0000 | −0.0332 | 0.2497 | 0.0752 | −0.2098 | 0.0611 | 0.1118 |
| sex | 0.0801 | −0.0332 | 1.0000 | −0.0612 | −0.0895 | −0.4964 | −0.0804 | 0.0186 |
| Smoking status | 0.0124 | 0.2497 | −0.0612 | 1.0000 | 0.1239 | −0.1358 | 0.1740 | 0.0693 |
| Pack years | 0.0629 | 0.0752 | −0.0895 | 0.1239 | 1.0000 | −0.0902 | 0.0742 | 0.0719 |
| Baseline FEV1 | −0.2997 | −0.2098 | −0.4964 | −0.1358 | −0.0902 | 1.0000 | −0.5970 | −0.3535 |
| COPD status | 0.1996 | 0.0611 | −0.0804 | 0.1740 | 0.0742 | −0.5970 | 1.0000 | 0.4656 |
| Follow up time | 0.0859 | 0.1118 | 0.0186 | 0.0693 | 0.0719 | −0.3535 | 0.4656 | 1.000 |

TABLE 3

The p-values as a result of the Pearson's correlation test between each variable.

|  | ΔFEV1 | age | sex | Smoking status | Pack Years | Baseline FEV1 | COPD status | Follow up time |
|---|---|---|---|---|---|---|---|---|
| ΔFEV1 | NA | 0.1688 | 0.3576 | 0.8873 | 0.4843 | 0.0004 | 0.0208 | 0.3234 |
| age | 0.1688 | NA | 0.7033 | 0.0036 | 0.4026 | 0.0150 | 0.4834 | 0.1986 |
| sex | 0.3576 | 0.7033 | NA | 0.4821 | 0.3189 | 0.0000 | 0.3560 | 0.8310 |
| Smoking status | 0.8873 | 0.0036 | 0.4821 | NA | 0.1668 | 0.1178 | 0.0444 | 0.4262 |
| Pack years | 0.4843 | 0.4026 | 0.3189 | 0.1668 | NA | 0.3151 | 0.4090 | 0.4234 |
| Baseline FEV1 | 0.0004 | 0.0150 | <0.0001 | 0.1178 | 0.3151 | NA | <0.0001 | <0.0001 |
| COPD status | 0.0208 | 0.4834 | 0.3560 | 0.0444 | 0.4090 | <0.0001 | NA | <0.0001 |
| Follow up time | 0.3234 | 0.1986 | 0.8310 | 0.4262 | 0.4234 | <0.0001 | <0.0001 | NA |

TABLE 4

Demographics of the training cohort separated by GOLD and COPD status. The mean, standard deviation, and range are shown for continuous traits.

|  | GOLD1 | GOLD2 | GOLD3 | No COPD |
|---|---|---|---|---|
| n | 22 | 40 | 9 | 63 |
| age | 64 +/− 6 (55.08-72.33) years | 65 +/− 6 (54.17-75.17) years | 61 +/− 5 (51.92-66.92) years | 64 +/− 5 (49.33-77.17) years |
| pack years | 43 +/− 20 (12-102) (missing 1) | 47 +/− 18 (20-95.8) (missing 3) | 53 +/− 13 (34.02-72) (missing 0) | 46 +/− 15 (13-102) (missing 4) |
| Smoking Status | 11C/11F | 14C/26F | 2C/7F | 32C/31F |
| Sex | 13M/9F | 24M/16F | 6M/3F | 32M/31F |
| inhaled medication | 4 Yes/18 No | 11 Yes/29 No | 1 Yes/8 No | 4 Yes/59 No |
| Change in $FEV_1$ | −55.33 +/− 43.31 (−140-30) mL | −30.81 +/− 36.35 (−100-40) mL | 21.48 +/− 72.41 (−70-170) mL | −35.91 +/− 46.23 (−170-60) mL |
| Change in $FEV_1$ % predicted | −73.28 +/− 180.29 (−392-253) | −39.1 +/− 130.91 (−250-277) | 91.5 +/− 235.55 (−177-509) | −11.71 +/− 162.78 (−403-338) |
| Baseline $FEV_1$ | 2811.82 +/− 756.03 (1190-4190) mL | 1999.25 +/− 425.91 (1240-2840) mL | 1294.44 +/− 236.07 (950-1700) mL | 2846.03 +/− 687.89 (1730-4520) mL |
| Follow up time | 5.51 +/− 1.72 (4.11-9.13) years | 8.01 +/− 3 (4.24-12.64) years | 7.4 +/− 3.09 (4.14-11.62) years | 5.51 +/− 1.56 (4.08-9.22) years |

TABLE 5

Range of the number of days between baseline spirometry measurement and bronchoscopy.

| Days between spirometry and bronchoscopy | Number of people (% of total) N = 134 |
|---|---|
| 0-90 days | 94 (70.14%) |
| 91-180 days | 31 (15.67%) |
| 181-270 days | 5 (3.73%) |
| 271-365 days | 4 (2.99%) |

TABLE 6

Genes associated with lung function decline (FDR < 0.05).

| cluster | gene name | coefficient | t value | p value | fdr |
|---|---|---|---|---|---|
| 1 | TCN1 | 0.8887 | 6.6921 | 7.6134E−10 | 0.0009 |
| 1 | AHCYL2 | 0.1990 | 6.0518 | 1.7093E−08 | 0.0021 |
| 1 | GALNT4 | 0.1347 | 4.1961 | 5.2596E−05 | 0.0030 |
| 1 | MFSD4 | 0.1451 | 3.6378 | 4.0784E−04 | 0.0030 |
| 1 | PLA2G4A | 0.4539 | 7.8505 | 2.0231E−12 | 0.0036 |
| 1 | TSPAN13 | 0.1012 | 2.4304 | 1.6575E−02 | 0.0039 |
| 1 | TM9SF3 | 0.0538 | 2.2535 | 2.6057E−02 | 0.0039 |
| 1 | GALNT5 | 0.3536 | 4.9970 | 2.0224E−06 | 0.0052 |
| 1 | GALNT7 | 0.2456 | 5.0373 | 1.7013E−06 | 0.0055 |
| 1 | PARM1 | 0.4308 | 6.7067 | 7.0804E−10 | 0.0070 |
| 1 | SURF4 | 0.1296 | 4.0527 | 9.0659E−05 | 0.0088 |

TABLE 6-continued

Genes associated with lung function decline (FDR < 0.05).

| cluster | gene name | coefficient | t value | p value | fdr |
|---|---|---|---|---|---|
| 1 | GALNT12 | 0.2142 | 5.0827 | 1.3985E−06 | 0.0091 |
| 2 | KIF13A | −0.0694 | −3.1520 | 2.0521E−03 | 0.0091 |
| 1 | ARMCX3 | 0.2271 | 5.6519 | 1.1054E−07 | 0.0108 |
| 1 | CEACAM5 | 1.0590 | 6.2098 | 8.0399E−09 | 0.0157 |
| 1 | RDH10 | 0.2619 | 4.6637 | 8.1888E−06 | 0.0157 |
| 2 | TBC1D22B | −0.0573 | −2.7263 | 7.3730E−03 | 0.0157 |
| 2 | CCDC69 | −0.1268 | −3.9545 | 1.3072E−04 | 0.0157 |
| 2 | PRKCE | −0.1915 | −6.1077 | 1.3104E−08 | 0.0157 |
| 2 | BBS1 | −0.0433 | −1.8700 | 6.3947E−02 | 0.0159 |
| 1 | ENTPD4 | 0.1445 | 5.7411 | 7.3305E−08 | 0.0190 |
| 1 | FUT6 | 0.2109 | 5.6158 | 1.3041E−07 | 0.0190 |
| 1 | PTHLH | 0.1749 | 5.2112 | 7.9895E−07 | 0.0190 |
| 1 | ASRGL1 | 0.3407 | 5.0219 | 1.8171E−06 | 0.0190 |
| 1 | S100A16 | 0.2964 | 4.6584 | 8.3684E−06 | 0.0190 |
| 1 | SLC26A2 | 0.3071 | 4.3327 | 3.0944E−05 | 0.0190 |
| 1 | CTSC | 0.1910 | 4.2498 | 4.2752E−05 | 0.0190 |
| 1 | LRRC8A | 0.1339 | 4.1118 | 7.2536E−05 | 0.0190 |
| 1 | TMEM165 | 0.1064 | 3.9814 | 1.1830E−04 | 0.0190 |
| 1 | PDXDC1 | 0.0859 | 3.8893 | 1.6608E−04 | 0.0190 |
| 1 | GNPNAT1 | 0.1688 | 3.7946 | 2.3401E−04 | 0.0190 |
| 1 | TSPAN8 | 0.1827 | 3.4081 | 8.9346E−04 | 0.0190 |
| 1 | SLC39A8 | 0.1607 | 2.7338 | 7.2164E−03 | 0.0190 |
| 1 | MAGT1 | 0.1004 | 2.5909 | 1.0768E−02 | 0.0190 |
| 2 | FAM53B | −0.0365 | −1.3674 | 1.7408E−01 | 0.0190 |
| 1 | ATP13A5 | 0.3690 | 3.5938 | 4.7516E−04 | 0.0198 |
| 1 | CLDN10 | 0.3523 | 4.7489 | 5.7590E−06 | 0.0209 |
| 1 | ENTPD3 | 0.1366 | 2.8824 | 4.6834E−03 | 0.0209 |
| 1 | FER1L6 | 0.2096 | 3.6951 | 3.3349E−04 | 0.0222 |
| 1 | PPAPDC1B | 0.0654 | 2.6785 | 8.4422E−03 | 0.0222 |
| 2 | LINC00341 | −0.2658 | −6.5483 | 1.5502E−09 | 0.0222 |
| 1 | AP2B1 | 0.2532 | 5.3500 | 4.3259E−07 | 0.0224 |
| 1 | S100A14 | 0.3039 | 4.5219 | 1.4584E−05 | 0.0224 |
| 2 | MAML2 | −0.0687 | −2.5595 | 1.1734E−02 | 0.0224 |
| 1 | SCEL | 0.3528 | 4.0001 | 1.1035E−04 | 0.0230 |
| 2 | SRGAP2 | −0.0491 | −1.6052 | 1.1111E−01 | 0.0230 |
| 2 | CCDC170 | −0.0623 | −2.0020 | 4.7562E−02 | 0.0230 |
| 2 | CNNM2 | −0.0869 | −3.3922 | 9.4182E−04 | 0.0230 |
| 1 | GALE | 0.2329 | 5.3202 | 4.9389E−07 | 0.0237 |
| 1 | SEC31A | 0.0830 | 4.5324 | 1.3977E−05 | 0.0237 |
| 1 | AZGP1 | 0.2825 | 3.7904 | 2.3764E−04 | 0.0237 |
| 1 | NNT | 0.1186 | 3.3663 | 1.0264E−03 | 0.0237 |
| 2 | WWC1 | −0.0690 | −2.6665 | 8.7313E−03 | 0.0237 |
| 2 | CD38 | −0.1241 | −3.8009 | 2.2882E−04 | 0.0237 |
| 2 | HIST3H2BB | −0.1131 | −3.0306 | 2.9947E−03 | 0.0243 |
| 2 | KCNB1 | −0.1406 | −3.4488 | 7.7959E−04 | 0.0246 |
| 2 | HEY2 | −0.2682 | −6.1283 | 1.1878E−08 | 0.0246 |
| 1 | ARMCX6 | 0.1339 | 4.9151 | 2.8672E−06 | 0.0246 |
| 1 | UPK1B | 0.7030 | 5.3836 | 3.7239E−07 | 0.0247 |
| 1 | MORC4 | 0.1107 | 4.6763 | 7.7764E−06 | 0.0257 |
| 1 | PRSS23 | 0.1507 | 3.2837 | 1.3456E−03 | 0.0257 |
| 2 | PCNT | −0.0342 | −1.7746 | 7.8516E−02 | 0.0257 |
| 2 | C11orf63 | −0.1213 | −3.5290 | 5.9395E−04 | 0.0257 |
| 1 | EIF2AK3 | 0.1497 | 4.9486 | 2.4868E−06 | 0.0266 |
| 1 | TXNDC11 | 0.0711 | 3.3886 | 9.5325E−04 | 0.0268 |
| 2 | GAB2 | −0.1370 | −4.4744 | 1.7651E−05 | 0.0270 |
| 1 | SLC31A1 | 0.1267 | 3.1891 | 1.8242E−03 | 0.0277 |
| 2 | KIF24 | −0.0034 | −0.1167 | 9.0727E−01 | 0.0278 |
| 2 | ZNF709 | −0.1331 | −3.7141 | 3.1190E−04 | 0.0286 |
| 1 | S100P | 0.3451 | 4.4734 | 1.7718E−05 | 0.0299 |
| 2 | CYP27A1 | −0.2464 | −4.1501 | 6.2707E−05 | 0.0299 |
| 1 | TMPRSS4 | 0.3204 | 6.3268 | 4.5700E−09 | 0.0300 |
| 1 | FZD5 | 0.1599 | 4.9201 | 2.8069E−06 | 0.0300 |
| 1 | CREB3L1 | 0.2775 | 4.8160 | 4.3526E−06 | 0.0300 |
| 1 | FAM177B | 0.6235 | 4.4232 | 2.1645E−05 | 0.0300 |
| 1 | MIA3 | 0.1468 | 4.2183 | 4.8279E−05 | 0.0300 |
| 1 | HMGCS2 | 0.3171 | 3.1023 | 2.3988E−03 | 0.0300 |
| 1 | MUC2 | 0.1958 | 2.7504 | 6.8826E−03 | 0.0300 |
| 1 | EPT1 | 0.1037 | 2.7462 | 6.9666E−03 | 0.0300 |
| 1 | SLC44A3 | 0.0435 | 1.3486 | 1.8002E−01 | 0.0300 |
| 1 | WDR72 | 0.0788 | 1.2563 | 2.1146E−01 | 0.0300 |
| 2 | FHAD1 | −0.0173 | −0.6200 | 5.3646E−01 | 0.0300 |
| 2 | SCAI | −0.0539 | −2.0576 | 4.1813E−02 | 0.0300 |
| 2 | BRF1 | −0.0488 | −2.5239 | 1.2923E−02 | 0.0300 |
| 2 | ZNF382 | −0.2612 | −3.2461 | 1.5198E−03 | 0.0300 |
| 2 | ZNF473 | −0.0716 | −3.2754 | 1.3825E−03 | 0.0300 |
| 2 | ZNF544 | −0.0467 | −2.1874 | 3.0672E−02 | 0.0301 |

TABLE 6-continued

Genes associated with lung function decline (FDR < 0.05).

| cluster | gene name | coefficient | t value | p value | fdr |
|---|---|---|---|---|---|
| 1 | STK38L | 0.1599 | 5.3536 | 4.2577E−07 | 0.0304 |
| 1 | MTHFD2 | 0.2906 | 5.0806 | 1.4112E−06 | 0.0304 |
| 1 | VTCN1 | 0.2400 | 3.8693 | 1.7867E−04 | 0.0304 |
| 1 | PRRC1 | 0.0632 | 2.6847 | 8.2962E−03 | 0.0304 |
| 2 | SNRK | −0.1090 | −4.7096 | 6.7775E−06 | 0.0304 |
| 1 | DISP1 | 0.1657 | 4.2544 | 4.2001E−05 | 0.0307 |
| 1 | KDELR2 | 0.0952 | 2.7757 | 6.3999E−03 | 0.0307 |
| 2 | CEP250 | −0.0226 | −1.1570 | 2.4959E−01 | 0.0307 |
| 2 | USP2 | −0.0668 | −2.5884 | 1.0845E−02 | 0.0309 |
| 1 | SEC24A | 0.0953 | 3.7260 | 2.9896E−04 | 0.0330 |
| 1 | KCNK6 | 0.1344 | 4.3019 | 3.4905E−05 | 0.0343 |
| 2 | STXBP1 | −0.1648 | −5.8005 | 5.5667E−08 | 0.0343 |
| 1 | DGKA | 0.3001 | 5.0450 | 1.6455E−06 | 0.0345 |
| 1 | MYO1C | 0.1606 | 4.8221 | 4.2441E−06 | 0.0345 |
| 1 | RPN2 | 0.0734 | 2.7575 | 6.7432E−03 | 0.0345 |
| 1 | ATP6V0E1 | 0.0096 | 0.2905 | 7.7197E−01 | 0.0345 |
| 1 | FUT2 | 0.3010 | 4.8006 | 4.6433E−06 | 0.0358 |
| 1 | ACBD3 | 0.0311 | 1.8237 | 7.0702E−02 | 0.0358 |
| 1 | CYP2C18 | 0.3683 | 5.7060 | 8.6200E−08 | 0.0358 |
| 1 | B4GALT4 | 0.2220 | 4.2800 | 3.8014E−05 | 0.0358 |
| 1 | ANO10 | 0.1315 | 4.2233 | 4.7358E−05 | 0.0358 |
| 1 | PRSS8 | 0.2071 | 4.1302 | 6.7653E−05 | 0.0358 |
| 1 | VIPR1 | 0.0858 | 2.5092 | 1.3445E−02 | 0.0358 |
| 1 | MFSD1 | 0.0664 | 2.1757 | 3.1552E−02 | 0.0358 |
| 2 | ENO4 | −0.1021 | −3.2743 | 1.3873E−03 | 0.0358 |
| 2 | RGAG4 | −0.1126 | −3.5090 | 6.3587E−04 | 0.0358 |
| 1 | GNE | 0.1788 | 4.8118 | 4.4311E−06 | 0.0360 |
| 1 | TSPAN5 | 0.2675 | 4.5062 | 1.5535E−05 | 0.0360 |
| 1 | TMEM39A | 0.0628 | 2.5526 | 1.1958E−02 | 0.0360 |
| 1 | SLC1A5 | 0.1077 | 2.3482 | 2.0515E−02 | 0.0360 |
| 2 | STPG1 | −0.0642 | −2.2706 | 2.4967E−02 | 0.0363 |
| 1 | FUT3 | 0.3613 | 6.3135 | 4.8759E−09 | 0.0369 |
| 1 | LOC100128816 | 0.1631 | 3.3440 | 1.1048E−03 | 0.0369 |
| 1 | C12orf23 | 0.1078 | 3.0662 | 2.6832E−03 | 0.0369 |
| 1 | IDH1 | 0.1305 | 2.9882 | 3.4094E−03 | 0.0369 |
| 1 | TMEM167A | 0.0583 | 1.5513 | 1.2348E−01 | 0.0369 |
| 2 | IL5RA | −0.1306 | −3.7257 | 2.9937E−04 | 0.0369 |
| 1 | AP4B1 | 0.0981 | 4.3548 | 2.8374E−05 | 0.0371 |
| 1 | PDK1 | 0.1418 | 4.4987 | 1.6013E−05 | 0.0374 |
| 1 | SPTSSA | 0.0826 | 2.0856 | 3.9148E−02 | 0.0379 |
| 1 | SMPDL3A | 0.1006 | 1.9271 | 5.6347E−02 | 0.0391 |
| 2 | ULK2 | −0.1182 | −4.6570 | 8.4187E−06 | 0.0392 |
| 2 | ZBTB44 | −0.0742 | −2.7533 | 6.8247E−03 | 0.0396 |
| 1 | ADAM9 | 0.1733 | 4.4067 | 2.3114E−05 | 0.0400 |
| 1 | SLC16A9 | 0.0808 | 1.5343 | 1.2762E−01 | 0.0401 |
| 1 | SEC61A1 | 0.1313 | 4.1740 | 5.7250E−05 | 0.0402 |
| 2 | NSUN7 | −0.1143 | −3.1793 | 1.8820E−03 | 0.0403 |
| 1 | ANP32E | 0.0090 | 0.2064 | 8.3685E−01 | 0.0409 |
| 2 | KCNJ2 | −0.2242 | −5.4818 | 2.3964E−07 | 0.0411 |
| 1 | CEACAM6 | 0.3212 | 5.4082 | 3.3357E−07 | 0.0414 |
| 1 | TMEM211 | 0.1995 | 3.1445 | 2.1010E−03 | 0.0414 |
| 1 | OPN1LW | 0.0444 | 0.9593 | 3.3937E−01 | 0.0414 |
| 2 | NEK4 | −0.0537 | −2.4690 | 1.4967E−02 | 0.0419 |
| 1 | FGFBP1 | 0.4861 | 5.1120 | 1.2319E−06 | 0.0426 |
| 1 | SLC12A8 | 0.1307 | 3.8853 | 1.6850E−04 | 0.0426 |
| 2 | CEP104 | −0.0057 | −0.3993 | 6.9038E−01 | 0.0427 |
| 1 | SERPINB8 | 0.2376 | 5.1579 | 1.0090E−06 | 0.0428 |
| 1 | CTTNBP2 | 0.1661 | 3.3132 | 1.2224E−03 | 0.0428 |
| 2 | CCDC151 | −0.0118 | −0.3666 | 7.1458E−01 | 0.0428 |
| 2 | LAMC2 | −0.0756 | −2.3678 | 1.9507E−02 | 0.0428 |
| 2 | NEK11 | −0.1008 | −3.4690 | 7.2827E−04 | 0.0428 |
| 2 | ZFP82 | −0.1466 | −3.5803 | 4.9786E−04 | 0.0428 |
| 1 | BCL2L15 | 0.3704 | 5.5125 | 2.0858E−07 | 0.0429 |
| 1 | ALG14 | 0.0643 | 2.2389 | 2.7020E−02 | 0.0440 |
| 1 | FKBP14 | 0.1638 | 3.6950 | 3.3366E−04 | 0.0442 |
| 1 | ZNF391 | 0.0065 | 0.1334 | 8.9411E−01 | 0.0444 |
| 1 | DHX15 | 0.0360 | 1.6433 | 1.0296E−01 | 0.0449 |
| 2 | EZH1 | −0.0920 | −4.0605 | 8.8059E−05 | 0.0449 |
| 2 | PCSK6 | −0.0455 | −1.0869 | 2.7929E−01 | 0.0453 |
| 1 | TUBA1C | 0.2117 | 3.9781 | 1.1976E−04 | 0.0454 |
| 1 | MOB4 | 0.0793 | 1.4723 | 1.4357E−01 | 0.0454 |
| 1 | PGBD2 | 0.0928 | 2.6609 | 8.8693E−03 | 0.0459 |
| 1 | KCNK1 | 0.0651 | 2.1769 | 3.1464E−02 | 0.0480 |
| 2 | PRSS12 | −0.1103 | −3.5504 | 5.5185E−04 | 0.0488 |
| 1 | MAL2 | 0.0696 | 2.7612 | 6.6732E−03 | 0.0492 |
| 1 | PDIA5 | 0.1182 | 3.1033 | 2.3914E−03 | 0.0498 |

TABLE 6-continued

Genes associated with lung function decline (FDR < 0.05).

| cluster | gene name | coefficient | t value | p value | fdr |
|---|---|---|---|---|---|
| 1 | TPBG | 0.1526 | 5.7027 | 8.7510E−08 | 0.0499 |
| 1 | GPT2 | 0.2308 | 4.5660 | 1.2201E−05 | 0.0499 |
| 1 | TMED3 | 0.1677 | 4.3693 | 2.6801E−05 | 0.0499 |
| 1 | TIMP1 | 0.2585 | 4.3170 | 3.2907E−05 | 0.0499 |
| 1 | CANT1 | 0.1051 | 3.2163 | 1.6724E−03 | 0.0499 |
| 1 | NIPA2 | 0.0041 | 0.1808 | 8.5683E−01 | 0.0499 |
| 2 | PYGO1 | −0.3110 | −4.6256 | 9.5747E−06 | 0.0499 |
| 2 | FXYD6 | −0.2159 | −5.3948 | 3.5424E−07 | 0.0499 |

TABLE 7

Sensitivity Analysis. Linear models were used to identify genes that changed in advance of lung function decline when controlling for age, sex, smoking status, pack years, and baseline $FEV_1$ in subsets of the study population: current smokers, former smokers, and individuals not taking inhaled corticosteroids. There was a significant enrichment identified between the cluster 2 genes from the $FEV_1$ decline signature in genes ranked by their t-value from these linear models.

| Group | N people | Significant genes (FDR < 0.05) | Gene Set | Enrichment score | FDR-q value |
|---|---|---|---|---|---|
| Current Smokers only | 75 | 0 | Cluster 2 (51 genes) | −0.39 | 0.015 |
| Former smokers only | 59 | 0 | Cluster 2 (51 genes) | −0.41 | 0.021 |
| No medications | 114 | 0 | Cluster 2 (51 genes) | −0.39 | 0.024 |

TABLE 8

Demographics of the GLUCOLD cohort. The mean and standard deviation are shown for continuous variables.

| | N = 46 |
|---|---|
| Age | 61.11 +/− 7.97 (46-74) years |
| Smoking Status | 26 Current, 20 Former |
| Sex | 40M, 6F |
| Baseline FEV1 | 2.09 +/− 0.49 (1.33-3.28) L |
| $\Delta FEV_1$ | −60.53 +/− 44.29 (−211.34-57.44) mL/year |
| Follow up time | 6.76 +/− 1.32 (3.5-7.5) years |

TABLE 9

Transcription Factor binding sites enriched in the genes that increase with more severe lung function decline (cluster 1)

| Gene Set Name | # Genes in Gene Set (K) | Description | # Genes in Overlap (k) | k/K | p-value | FDR q-value |
|---|---|---|---|---|---|---|
| TTGTTT_FOXO4_01 | 2061 | Genes having at least one occurence of the highly conserved motif M60 TTGTTT sites. The motif matches transcription factor binding site V$FOXO4_01 (v7.4 TRANSFAC). | 19 | 0.0092 | 8.78E−07 | 3.68E−04 |
| CAGGTG_E12_Q6 | 2485 | Genes having at least one occurence of the highly conserved motif M12 CAGGTG sites. The motif matches transcription factor binding site V$E12_Q6 (v7.4 TRANSFAC). | 21 | 0.0085 | 8.80E−07 | 3.68E−04 |
| HTF_01 | 72 | Genes having at least one occurence of the transcription factor binding site V$HTF_01 (v7.4 TRANSFAC) in the regions spanning up to 4 kb around their transcription starting sites. | 4 | 0.0556 | 3.36E−05 | 8.37E−03 |
| GGGCGGR_SP1_Q6 | 2940 | Genes having at least one occurence of the highly conserved motif M6 GGGCGGR sites. The motif matches transcription factor binding site V$SP1_Q6 (v7.4 TRANSFAC). | 20 | 0.0068 | 4.00E−05 | 8.37E−03 |
| TGANNYRGCA_TCF11MAFG_01 | 301 | Genes having at least one occurence of the highly conserved motif M67 TGANNYRGCA sites. The motif matches transcription factor binding site V$TCF11MAFG_01 (v7.4 TRANSFAC). | 6 | 0.0199 | 1.16E−04 | 1.47E−02 |
| CTTTGT_LEF1_Q2 | 1972 | Genes having at least one occurence of the highly conserved motif M13 CTTTGT sites. The motif matches transcription factor binding site V$LEF1_Q2 (v7.4 TRANSFAC). | 15 | 0.0076 | 1.23E−04 | 1.47E−02 |

TABLE 9-continued

Transcription Factor binding sites enriched in the genes that increase with more severe lung function decline (cluster 1)

| Gene Set Name | # Genes in Gene Set (K) | Description | # Genes in Overlap (k) | k/K | p-value | FDR q-value |
| --- | --- | --- | --- | --- | --- | --- |
| CTTTAAR_UNKNOWN | 972 | Genes having at least one occurence of the highly conserved motif M29 CTTTAAR in the region spanning up to 4 kb around their transcription start sites. The motif does not match any known transcription factor binding site (v7.4 TRANSFAC). | 10 | 0.0103 | 1.73E−04 | 1.80E−02 |
| ATF6_01 | 123 | Genes having at least one occurence of the transcription factor binding site V$ATF6_01 (v7.4 TRANSFAC) in the regions spanning up to 4 kb around their transcription starting sites. | 4 | 0.0325 | 2.69E−04 | 2.49E−02 |
| XBP1_01 | 133 | Genes having at least one occurence of the transcription factor binding site V$XBP1_01 (v7.4 TRANSFAC) in the regions spanning up to 4 kb around their transcription starting sites. | 4 | 0.0301 | 3.61E−04 | 3.02E−02 |
| GGGAGGRR_MAZ_Q6 | 2274 | Genes having at least one occurence of the highly conserved motif M24 GGGAGGRR sites. The motif matches transcription factor binding site V$MAZ_Q6 (v7.4 TRANSFAC). | 15 | 0.0066 | 5.61E−04 | 4.26E−02 |

TABLE 10

Transcription Factor binding sites enriched in the genes that decrease with more severe lung function decline (cluster 2)

| Gene Set Name | # Genes in Gene Set (K) | Description | # Genes in Overlap (k) | k/K | p-value | FDR q-value |
| --- | --- | --- | --- | --- | --- | --- |
| CAGGTG_E12_Q6 | 2485 | Genes having at least one occurence of the highly conserved motif M12 CAGGTG sites. The motif matches transcription factor binding site V$E12_Q6 (v7.4 TRANSFAC). | 14 | 0.0056 | 1.49E−07 | 1.24E−04 |
| GGGAGGRR_MAZ_Q6 | 2274 | Genes having at least one occurence of the highly conserved motif M24 GGGAGGRR sites. The motif matches transcription factor binding site V$MAZ_Q6 (v7.4 TRANSFAC). | 12 | 0.0053 | 2.76E−06 | 7.69E−04 |
| TEF1_Q6 | 226 | Genes having at least one occurence of the transcription factor binding site V$TEF1_Q6 (v7.4 TRANSFAC) in the regions spanning up to 4 kb around their transcription starting sites. | 5 | 0.0221 | 3.97E−06 | 8.29E−04 |
| TTGTTT_FOXO4_01 | 2061 | Genes having at least one occurence of the highly conserved motif M60 TTGTTT sites. The motif matches transcription factor binding site V$FOXO4_01 (v7.4 TRANSFAC). | 11 | 0.0053 | 6.99E−06 | 1.17E−03 |
| SRY_01 | 224 | Genes having at least one occurence of the transcription factor binding site V$SRY_01 (v7.4 TRANSFAC) in the regions spanning up to 4 kb around their transcription starting sites. | 4 | 0.0179 | 9.04E−05 | 1.22E−02 |

TABLE 10-continued

Transcription Factor binding sites enriched in the genes that decrease with more severe lung function decline (cluster 2)

| Gene Set Name | # Genes in Gene Set (K) | Description | # Genes in Overlap (k) | k/K | p-value | FDR q-value |
|---|---|---|---|---|---|---|
| E2A_Q2 | 243 | Genes having at least one occurence of the transcription factor binding site V$E2A_Q2 (v7.4 TRANSFAC) in the regions spanning up to 4 kb around their transcription starting sites. | 4 | 0.0165 | 1.24E-04 | 1.22E-02 |
| S8_01 | 245 | Genes having at least one occurence of the transcription factor binding site V$S8_01 (v7.4 TRANSFAC) in the regions spanning up to 4 kb around their transcription starting sites. | 4 | 0.0163 | 1.28E-04 | 1.22E-02 |
| ZIC2_01 | 247 | Genes having at least one occurence of the transcription factor binding site V$ZIC2_01 (v7.4 TRANSFAC) in the regions spanning up to 4 kb around their transcription starting sites. | 4 | 0.0162 | 1.32E-04 | 1.22E-02 |
| E12_Q6 | 262 | Genes having at least one occurence of the transcription factor binding site V$E12_Q6 (v7.4 TRANSFAC) in the regions spanning up to 4 kb around their transcription starting sites. | 4 | 0.0153 | 1.65E-04 | 1.29E-02 |
| LMO2COM_01 | 264 | Genes having at least one occurence of the transcription factor binding site V$LMO2COM_01 (v7.4 TRANSFAC) in the regions spanning up to 4 kb around their transcription starting sites. | 4 | 0.0152 | 1.70E-04 | 1.29E-02 |
| AP1_Q2_01 | 275 | Genes having at least one occurence of the transcription factor binding site V$AP1_Q2_01 (v7.4 TRANSFAC) in the regions spanning up to 4 kb around their transcription starting sites. | 4 | 0.0145 | 1.98E-04 | 1.38E-02 |
| TGACAGNY_MEIS1_01 | 827 | Genes having at least one occurence of the highly conserved motif M41 TGACAGNY sites. The motif matches transcription factor binding site V$MEIS1_01 (v7.4 TRANSFAC). | 6 | 0.0073 | 2.15E-04 | 1.38E-02 |
| GGGYGTGNY_UNKNOWN | 664 | Genes having at least one occurence of the highly conserved motif M31 GGGYGTGNY in the region spanning up to 4 kb around their transcription start sites. The motif does not match any known transcription factor binding site (v7.4 TRANSFAC). | 5 | 0.0075 | 6.36E-04 | 3.32E-02 |
| TGCCAAR_NF1_Q6 | 722 | Genes having at least one occurence of the highly conserved motif M47 TGCCAAR sites. The motif matches transcription factor binding site V$NF1_Q6 (v7.4 TRANSFAC). | 5 | 0.0069 | 9.25E-04 | 4.30E-02 |

CITATIONS

1 Tammemagi M C, Lam S C, McWilliams A M, et al. Incremental Value of Pulmonary Function and Sputum DNA Image Cytometry in Lung Cancer Risk Prediction. *Cancer Prev Res* (Phila Pa.) 2011; 4:552-61. doi:10.1158/1940-6207.CAPR-10-0183

What is claimed herein is:

1. A method of treating chronic obstructive pulmonary disease (COPD) in a subject in need thereof, the method comprising:
   a) determining the level of expression of one or more genes of a first group of genes, the first group of genes consisting of:
      surfeit 4 (SURF4); S100 calcium binding protein A16 (S100A16); MIA SH3 domain ER export factor 3 (MIA3); and thioredoxin domain containing 11 (TXNDC11);
   in a sample obtained from the subject in need of treatment for COPD; and
   b)
   i) administering to the subject one or more of:
   an inhaled long-acting antimuscarinic; an inhaled long-acting β2 agonist; and an inhaled corticosteroid;
   wherein the subject is determined to have an increased level of expression of one or more genes of the first group of genes relative to a patient who has never been a smoker or an age-matched patient who has never been a smoker; or
   ii) administering to the subject one or more of:
   intensive smoking cessation therapy and an inhaled short-acting β2 agonist; wherein the subject is determined not to have an increased level of expression of one or more genes of the first group of genes relative to a patient who has never been a smoker or an age-matched patient who has never been a smoker.

2. The method of claim 1, further comprising determining the level of expression of one or more of:
      UDP-galactose-4-epimerase (GALE); SEC61 translocon subunit alpha 1 (SEC61A1); KDEL endoplasmic reticulum protein retention receptor 2 (KDELR2); ADAM metallopeptidase domain 9 (ADAM9); and transmembrane p24 trafficking protein 3 (TMED3);
   in the sample obtained from the subject in need of treatment for COPD.

3. The method of claim 1, further comprising determining the level of expression of one or more of:
      ADAM metallopeptidase domain 9 (ADAM9); and transmembrane p24 trafficking protein 3 (TMED3);
   in the sample obtained from the subject in need of treatment for COPD.

4. The method of claim 1, wherein the level of expression of one or more of NOP2/Sun RNA methyltransferase family member 7 (NSUN7); LOC100128816; methylenetetrahydrofolate dehydrogenase (NADP+dependent) 2, (MTHFD2); KDEL endoplasmic reticulum protein retention receptor 2 (KDELR2); solute carrier family 44 member 3 (SLC44A3); solute carrier family 16 member 9 (SLC16A9); transmembrane p24 trafficking protein 3 (TMED3); tetraspanin 13 (TSPAN13); SEC61 translocon subunit alpha 1 (SEC61A1); and family with sequence similarity 177 member B (FAM177B) are not determined.

5. The method of claim 1, wherein the level of expression of one or both of enolase 4 (ENO4) and cAMP responsive element binding protein 3 like 1 (CREB3L1) are not determined.

6. The method of claim 1, wherein the expression of no more than 400 genes is determined.

7. The method of claim 1, wherein the level is the level in a sample obtained from bronchial brushing, bronchial biopsy, bronchial epithelium, airway epithelium, nasal brushing, or nasal epithelium.

8. The method of claim 1, wherein the level is the the level is the level in a sample obtained from nasal epithelium.

9. The method of claim 1, wherein the subject is a current or former tobacco smoker.

10. The method of claim 1, wherein the subject is a human.

11. The method of claim 10, wherein the human subject is at least 49 years old.

12. The method of claim 10, wherein the human subject is at least 58 years old.

13. The method of claim 1, wherein the subject has a Global Initiative for Chronic Obstructive Lung Disease (GOLD) grade of 2 or lower.

14. The method of claim 1, wherein the inhaled long-acting antimuscarinic is selected from the group consisting of: tiotropium; ipratropium; umiclinidium; aclidinium; and diphenhydramine.

15. The method of claim 1, wherein the inhaled long-acting β2 agonist is selected from the group consisting of: fomoterol; salmeterol; arformoterol; bambuterol; clenbuterol abediterol; carmoterol; olodaterol; indacaterol; and vlianterol.

16. The method of claim 1, wherein the inhaled corticosteroid is selected from the group consisting of: budesonide; fluticasone; flunisolide; triamcinolone acetonide; beclomethasone dipropionate; mometasone furoate; and ciclesonide.

17. The method of claim 1, wherein the inhaled short-acting β2 agonist is selected from the group consisting of: albuterol; bitolterol; fenoterol; isoprenaline; isoproterenol; levosalbutamol; levalbuterol; orciprenaline; metaproterenol; pirbuterol; procaterol; ritodrine; salbutamol; and terbutaline.

18. The method of claim 1, wherein the subject has a Global Initiative for Chronic Obstructive Lung Disease (GOLD) grade of 2 or lower and the method comprises administering to the subject two or more of:
   an inhaled long acting antimuscarinic; an inhaled long-acting β2 agonist; and an inhaled corticosteroid;
   wherein the subject is determined to have an increased level of expression of one or more genes of the first group of genes.

19. The method of claim 1, wherein the subject has a Global Initiative for Chronic Obstructive Lund Disease (GOLD) grade of 2 or lower and the method comprises administering to the subject:
   an inhaled long acting antimuscarinic; an inhaled long-acting β2 agonist; and an inhaled corticosteroid;
   wherein the subject is determined to have an increased level of expression of one or more genes of the first group of genes relative to the reference level.

20. The method of claim 1, further comprising determining the level of expression of at least one of:
   Transcobalamin 1 (TCN1); Adenosylhomocysteinease like 2 (AHCYL2); N-acetylgalactosaminyltransferase 4 (GALNT4); major facilitator superfamily domain containing 4A (MFSD4); phospholipase A2 group IVA (PLA2G4A); tetraspanin 13 (TSPAN13); transmembrane 9 superfamily member 3 (TM9SF3); N-acetylgalactosaminyltransferase 5 (GALNT5); N-acetylgalactosaminyltransferase 7 (GALNT7); prostate androgen-regulated mucin-like protein 1 (PARM1);

N-acetylgalactosaminyltransferase 12 (GALNT12); armadillo repeat containing X-linked 3 (ARMCX3); CEA cell adhesion molecule 5 (CEACAM5); retinol dehydrogenase 10 (RDH10); ectonucleoside triphosphate diphosphohydrolase 4 (ENTPD4); fucosyltransferase 6 (FUT6); parathyroid hormone like hormone (PTHLH); asparaginase and isoaspartyl peptidase 1 (ASRGL1); S100 calcium binding protein A16 (S100A16); solute carrier family 26 member 2 (SLC26A2); cathepsin C (CTSC); leucine rich repeat containing 8 VRAC subunit A (LRRC8A); transmembrane protein 165 (TMEM165); pyridoxal dependent decarboxylase domain containing 1 (PDXDC1); glucosamine-phosphate N-acetyltransferase 1 (GNPNAT1); tetraspanin 8 (TSPAN8); solute carrier family 39 member 8 (SLC39A8); Magnesium transporter 1 (MAGT1); ATPase 13A5 (ATP13A5); claudin 10 (CLDN10); ectonucleoside triphosphate diphosphohydrolase 3 (ENTPD3); fer-1 like family member 6 (FER1L6); phospholipid phosphatase 5 (PLPP5 or PPAPDC1B); adaptor related protein complex 2 subunit beta 1 (AP2B1); S100 calcium binding protein A14 (S100A14); Sciellin (SCEL); UDP-galactose-4-epimerase (GALE); SEC31 homolog A, COPII coat complex component (SEC31A); alpha-2-glycoprotein 1, zinc-binding (AZGP1); nicotinamide nucleotide transhydrogenase (NNT); armadillo repeat containing X-linked 6 (ARMCX6); uroplakin 1B (UPK1B); MORC family CW-type zinc finger 4 (MORC4); serine protease 23 (PRSS23); solute carrier family 31 member 1 (SLC31A1); S100 calcium binding protein P (S100P); transmembrane serine protease 4 (TMPRSS4); frizzled class receptor 5 (FZD5); cAMP responsive element binding protein 3 like 1 (CREB3L1); family with sequence similarity 177 member B (FAM177B); 3-hydroxy-3-methylglutaryl-CoA synthase 2 (HMGCS2); mucin 2 (MUC2); selenoprotein I (SELENO1 or EPT1); solute carrier family 44 member 3 (SLC44A3); WD repeat domain 72 (WDR72); serine/threonine kinase 38 like (STK38L); methylenetetrahydrofolate dehydrogenase (NADP+dependent) 2 (MTHFD2); V-set domain containing T cell activation inhibitor 1 (VTCN1); proline rich coiled-coil 1 (PRRC1); dispatched RND transporter family member 1 (DISP1); KDEL endoplasmic reticulum protein retention receptor 2 (KDELR2); SEC24 homolog A (SEC24A); potassium two pore domain channel subfamily K member 6 (KCNK6); diacylglycerol kinase alpha (DGKA); myosin 1C (MYO1C); ribophorin II (RPN2); ATPase H+ transporting V0 subunit el (ATP6VOE1); fucosyltransferase 2 (FUT2); acyl-CoA binding domain containing 3 (ACBD3); cytochrome P450 family 2 subfamily C member 18 (CYP2C18); beta-1,4-galactosyltransferase 4 (B4GALT4); Anoctamin 10 (ANO10); serine protease 8 (PRSS8); vasoactive intestinal peptide receptor 1 (VIPR1); major facilitator superfamily domain containing 1 (MFSD1); glucosamine (UDP-N-acetyl)-2-epimerase/N-acetylmannosamine kinase (GNE); tetraspanin 5 (TSPAN5); transmembrane protein 39A (TMEM39A); solute carrier family 1 member 5 (SLC1A5); fucosyltransferase 3 (FUT3); LOC100128816; an intron or splice variant of EF-hand calcium binding domain 4B (EFCAB4B); transmembrane protein 263 (TMEM263 or C12orf23); isocitrate dehydrogenase 1 (IDH1); transmembrane protein 167A (TMEM167A); adaptor related protein complex 4 subunit beta 1 (AP4B1); pyruvate dehydrogenase kinase 1 (PDK1); serine palmitoyltransferase small subunit A (SPTSSA); sphingomyelin phosphodiesterase acid like 3A (SMPDL3A); ADAM metallopeptidase domain 9 (ADAM9); solute carrier family 16 member 9 (SLC16A9); SEC61 translocon subunit alpha 1 (SEC61A1); acidic nuclear phosphoprotein 32 family member E (ANP32E); CEA cell adhesion molecule 6 (CEACAM6); transmembrane protein 211 (TMEM211); opsin 1, long wave sensitive (OPNILW); fibroblast growth factor binding protein 1 (FGFBP1); solute carrier family 12 member 8 (SLC12A8); serpin family B member 8 (SERPINB8); cortactin binding protein 2 (CTTNBP2); BCL2 like 15 (BCL2L15); UDP-N-acetylglucosaminyltransferase subunit (ALG14); FKBP prolyl isomerase 14 (FKBP14); Zinc finger 391 (ZNF391); DEAH-box helicase 15 (DHX15); tubulin alpha 1c (TUBA1C); MOB family member 4 (MOB4); piggyBac transposable element derived 2 (PGBD2); potassium two pore domain channel subfamily K member 1 (KCNK1); mal, T cell differentiation protein 2 (MAL2); protein disulfide isomerase family A member 5 (PDIA5); trophoblast glycoprotein (TPBG); glutamic—pyruvic transaminase 2 (GPT2); transmembrane p24 trafficking protein 3 (TMED3); TIMP metallopeptidase inhibitor 1 (TIMP1); calcium activated nucleotidase 1 (CANT1); and NIPA magnesium transporter 2 (NIPA2).

21. The method of claim 1, wherein:
step a) of the method further comprises determining the level of expression of one or more genes of a second group of genes, the second group of genes comprising: kinesin family member 13A (KIF13A); TBC1 domain family member 22B (TBC1D22B); coiled-coil domain containing 69 (CCDC69); protein kinase C epsilon (PRKCE); Bardet-Biedl syndrome 1 (BBS1); family with sequence similarity 53 member B (FAM53B); spectrin repeat containing nuclear envelope family member 3 (SYNE3 or LINC00341); mastermind like transcriptional coactivator 2 (MAML2); SLIT-ROBO Rho GTPase activating protein 2 (SRGAP2); coiled-coil domain containing 170 (CCDC170); cyclin and CBS domain divalent metal cation transport mediator 2 (CNNM2); WW and C2 domain containing 1 (WWC1); Cluster of differentiation 38 (CD38); H2B.U histone 1 (H2BU1 or HIST3H2BB); potassium voltage-gated channel subfamily B member 1 (KCNB1); hes related family bHLH transcription factor with YRPW motif 2 (HEY2); pericentrin (PCNT); junctional cadherin complex regulator (JHY or C1lorf63); GRB2 associated binding protein 2 (GAB2); kinesin family member 24 (KIF24); zinc finger protein 709 (ZNF709); cytochrome P450 family 27 subfamily A member 1 (CYP27A1); forkhead associated phosphopeptide binding domain 1 (FHAD1); suppressor of cancer cell invasion (SCAI); BRF1 RNA polymerase III transcription initiation factor subunit (BRF1); zinc finger protein 382 (ZNF382); zinc finger protein 473 (ZNF473); zinc finger protein 544 (ZNF544); SNF related kinase (SNRK); centrosomal protein 250 (CEP250); ubiquitin specific peptidase 2 (USP2); syntaxin binding protein 1 (STXBP1); enolase 4 (ENO4); retrotransposon Gag like 5 (RTL5 or RGAG4); sperm tail PG-rich repeat containing 1 (STPG1); interleukin 5 receptor subunit alpha (IL5RA)' unc-51 like autophagy activating kinase 2 (ULK2); zinc finger and BTB domain containing 44

(ZBTB44); NOP2/Sun RNA methyltransferase family member 7 (NSUN7); potassium inwardly rectifying channel subfamily J member 2 (KCNJ2); NIMA related kinase 4 (NEK4); centrosomal protein 104 (CEP104); outer dynein arm docking complex subunit 3 (ODAD3 or CCDC151); laminin subunit gamma 2 (LAMC2); NIMA related kinase 11 (NEK11); Zinc finger protein 82 (ZFP82); enhancer of zeste 1 (EZH1); proprotein convertase subtilisin/kexin type 6 (PCSK6); serine protease 12 (PRSS12); pygopus family PHD finger 1 (PYGO1); and FXYD domain containing ion transport regulator 6 (FXYD6); and step b) of the method further comprises
i) administering to the subject one or more of:
an inhaled long acting antimuscarinic; an inhaled long-acting β2 agonist; and an inhaled corticosteroid;
wherein the subject is determined to have an increased level of expression of one or more genes of the first group of genes or a decreased level of expression of one or more genes of the second group of genes relative to a patient who has never been a smoker or an age-matched patient who has never been a smoker; or
ii) administering to the subject one or more of:
intensive smoking cessation therapy and an inhaled short-acting β2 agonist; wherein the subject is determined not to have an increased level of expression of one or more genes of the first group of genes or a decreased level of expression of one or more genes of the second group of genes relative to a patient who has never been a smoker or an age-matched patient who has never been a smoker.

22. The method of claim 21, wherein the treatment administered to a subject determined to have an increased level of expression of one or more genes of the first group of genes or a decreased level of expression of one or more genes of the second group of genes further comprises administration of an inhibitor of one or more genes of the first group of genes or an agonist of one or more genes of the second group of genes.

23. A method comprising determining the level of expression of one or more genes of a first group of genes, the first group of genes consisting of:
surfeit 4 (SURF4); S100 calcium binding protein A16 (S100A16); MIA SH3 domain ER export factor 3 (MIA3); and thioredoxin domain containing 11 (TXNDC11);
in a sample obtained from a subject, wherein the sample is a bronchial brushing, bronchial biopsy, bronchial epithelium sample, airway epithelium sample, nasal brushing, or nasal epithelium sample.

24. The method of claim 23, further comprising determining the level of expression of at least one of:
Transcobalamin 1 (TCN1); Adenosylhomocysteinease like 2 (AHCYL2); N-acetylgalactosaminyltransferase 4 (GALNT4); major facilitator superfamily domain containing 4A (MFSD4); phospholipase A2 group IVA (PLA2G4A); tetraspanin 13 (TSPAN13); transmembrane 9 superfamily member 3 (TM9SF3); N-acetylgalactosaminyltransferase 5 (GALNT5); N-acetylgalactosaminyltransferase 7 (GALNT7); prostate androgen-regulated mucin-like protein 1 (PARM1); N-acetylgalactosaminyltransferase 12 (GALNT12); armadillo repeat containing X-linked 3 (ARMCX3); CEA cell adhesion molecule 5 (CEACAM5); retinol dehydrogenase 10 (RDH10); ectonucleoside triphosphate diphosphohydrolase 4 (ENTPD4); fucosyltransferase 6 (FUT6); parathyroid hormone like hormone (PTHLH); asparaginase and isoaspartyl peptidase 1 (ASRGL1); solute carrier family 26 member 2 (SLC26A2); cathepsin C (CTSC); leucine rich repeat containing 8 VRAC subunit A (LRRC8A); transmembrane protein 165 (TMEM165); pyridoxal dependent decarboxylase domain containing 1 (PDXDC1); glucosamine-phosphate N-acetyltransferase 1 (GNPNAT1); tetraspanin 8 (TSPAN8); solute carrier family 39 member 8 (SLC39A8); Magnesium transporter 1 (MAGT1); ATPase 13A5 (ATP13A5); claudin 10 (CLDN10); ectonucleoside triphosphate diphosphohydrolase 3 (ENTPD3); fer-1 like family member 6 (FER1L6); phospholipid phosphatase 5 (PLPP5 or PPAPDC1B); adaptor related protein complex 2 subunit beta 1 (AP2B1); S100 calcium binding protein A14 (S100A14); Sciellin (SCEL); UDP-galactose-4-epimerase (GALE); SEC31 homolog A, COPII coat complex component (SEC31A); alpha-2-glycoprotein 1, zinc-binding (AZGP1); nicotinamide nucleotide transhydrogenase (NNT); armadillo repeat containing X-linked 6 (ARMCX6); uroplakin 1B (UPK1B); MORC family CW-type zinc finger 4 (MORC4); serine protease 23 (PRSS23); solute carrier family 31 member 1 (SLC31A1); S100 calcium binding protein P (S100P); transmembrane serine protease 4 (TMPRSS4); frizzled class receptor 5 (FZD5); cAMP responsive element binding protein 3 like 1 (CREB3L1); family with sequence similarity 177 member B (FAM177B); 3-hydroxy-3-methylglutaryl-CoA synthase 2 (HMGCS2); mucin 2 (MUC2); selenoprotein I (SELENO1 or EPT1); solute carrier family 44 member 3 (SLC44A3); WD repeat domain 72 (WDR72); serine/threonine kinase 38 like (STK38L); 1 methylenetetrahydrofolate dehydrogenase (NADP+dependent) 2 (MTHFD2); V-set domain containing T cell activation inhibitor 1 (VTCN1); proline rich coiled-coil 1 (PRRC1); dispatched RND transporter family member 1 (DISP1); KDEL endoplasmic reticulum protein retention receptor 2 (KDELR2); SEC24 homolog A (SEC24A); potassium two pore domain channel subfamily K member 6 (KCNK6); diacylglycerol kinase alpha (DGKA); myosin 1C (MYO1C); ribophorin II (RPN2); ATPase H+ transporting V0 subunit el (ATP6VOE1); fucosyltransferase 2 (FUT2); acyl-CoA binding domain containing 3 (ACBD3); cytochrome P450 family 2 subfamily C member 18 (CYP2C18); beta-1,4-galactosyltransferase 4 (B4GALT4); Anoctamin 10 (ANO10); serine protease 8 (PRSS8); vasoactive intestinal peptide receptor 1 (VIPR1); major facilitator superfamily domain containing 1 (MFSD1); glucosamine (UDP-N-acetyl)-2-epimerase/N-acetylmannosamine kinase (GNE); tetraspanin 5 (TSPAN5); transmembrane protein 39A (TMEM39A); solute carrier family 1 member 5 (SLC1A5); fucosyltransferase 3 (FUT3); LOC100128816; an intron or splice variant of EF-hand calcium binding domain 4B (EFCAG4B); transmembrane protein 263 (TMEM263 or C12orf23); isocitrate dehydrogenase 1 (IDH1); transmembrane protein 167A (TMEM167A); adaptor related protein complex 4 subunit beta 1 (AP4B1); pyruvate dehydrogenase kinase 1 (PDK1); serine palmitoyltransferase small subunit A (SPTSSA); sphingomyelin phosphodiesterase acid like 3A (SMPDL3A); ADAM metallopeptidase domain 9 (ADAM9); solute carrier family 16 member 9 (SLC16A9); SEC61 translocon subunit alpha 1 (SEC61A1); acidic nuclear phosphoprotein 32 family member E (ANP32E); CEA cell adhesion molecule 6 (CEACAM6); transmembrane protein 211 (TMEM211); opsin 1, long wave sensitive (OPN1LW); fibroblast growth factor binding protein 1 (FGFBP1); solute carrier family 12 member 8 (SLC12A8); serpin family B member 8 (SERPINB8); cortactin binding protein 2 (CTTNBP2); BCL2 like 15 (BCL2L15); UDP-N-acetylglucosaminyltransferase subunit (ALG14); FKBP prolyl isomerase 14 (FKBP14); Zinc finger 391 (ZNF391); DEAH-box helicase 15 (DHX15); tubulin alpha 1c (TUBA1C); MOB family member 4 (MOB4); piggyBac transposable element derived 2 (PGBD2); potassium two pore domain channel subfamily K member 1 (KCNK1); mal, T cell differentiation protein 2 (MAL2); protein disulfide isomerase family A member 5 (PDIA5); trophoblast glycoprotein (TPBG); glutamic—pyruvic transaminase 2 (GPT2); transmembrane p24 trafficking protein 3 (TMED3); TIMP metallopeptidase inhibitor 1 (TIMP1); calcium activated nucleotidase 1 (CANT1); and NIPA magnesium transporter 2 (NIPA2).

25. The method of claim 23, wherein the method further comprises determining the level of expression of one or more genes of a second group of genes, the second group of genes comprising:

kinesin family member 13A (KIF13A); TBC1 domain family member 22B (TBC1D22B); coiled-coil domain containing 69 (CCDC69); protein kinase C epsilon (PRKCE); Bardet-Biedl syndrome 1 (BBS1); family with sequence similarity 53 member B (FAM53B); spectrin repeat containing nuclear envelope family member 3 (SYNE3 or LINC00341); mastermind like transcriptional coactivator 2 (MAML2); SLIT-ROBO Rho GTPase activating protein 2 (SRGAP2); coiled-coil domain containing 170 (CCDC170); cyclin and CBS domain divalent metal cation transport mediator 2 (CNNM2); WW and C2 domain containing 1 (WWC1); Cluster of differentiation 38 (CD38); H2B.U histone 1 (H2BU1 or HIST3H2BB); potassium voltage-gated channel subfamily B member 1 (KCNB1); hes related family bHLH transcription factor with YRPW motif 2 (HEY2); pericentrin (PCNT); junctional cadherin complex regulator (JHY or C11orf63); GRB2 associated binding protein 2 (GAB2); kinesin family member 24 (KIF24); zinc finger protein 709 (ZNF709); cytochrome P450 family 27 subfamily A member 1 (CYP27A1); forkhead associated phosphopeptide binding domain 1 (FHAD1); suppressor of cancer cell invasion (SCAI); BRF1 RNA polymerase III transcription initiation factor subunit (BRF1); zinc finger protein 382 (ZNF382); zinc finger protein 473 (ZNF473); zinc finger protein 544 (ZNF544); SNF related kinase (SNRK); centrosomal protein 250 (CEP250); ubiquitin specific peptidase 2 (USP2); syntaxin binding protein 1 (STXBP1); enolase 4 (ENO4); retrotransposon Gag like 5 (RTL5 or RGAG4); sperm tail PG-rich repeat containing 1 (STPG1); interleukin 5 receptor subunit alpha (IL5RA)' unc-51 like autophagy activating kinase 2 (ULK2); zinc finger and BTB domain containing 44 (ZBTB44); NOP2/Sun RNA methyltransferase family member 7 (NSUN7); potassium inwardly rectifying channel subfamily J member 2 (KCNJ2); NIMA related kinase 4 (NEK4); centrosomal protein 104 (CEP104); outer dynein arm docking complex subunit 3 (ODAD3 or CCDC151); laminin subunit gamma 2 (LAMC2); NIMA related kinase 11 (NEK11); Zinc finger protein 82 (ZFP82); enhancer of zeste 1 (EZH1); proprotein convertase subtilisin/kexin type 6 (PCSK6); serine protease 12 (PRSS12); pygopus family PHD finger 1 (PYGO1); and FXYD domain containing ion transport regulator 6 (FXYD6);

in the sample obtained from the subject.

26. A method of treating chronic obstructive pulmonary disease (COPD) in a subject in need thereof, the method comprising:

a) determining the level of expression of one or more genes of a first group of genes, the first group of genes consisting of:

surfeit 4 (SURF4); S100 calcium binding protein A16 (S100A16); MIA SH3 domain ER export factor 3 (MIA3); and thioredoxin domain containing 11 (TXNDC11);

in a sample obtained from the subject in need of treatment for COPD; and b)

i) administering to the subject one or more of:

an inhaled long acting antimuscarinic; an inhaled long-acting β2 agonist; and an inhaled corticosteroid;

wherein the subject is determined to have an increased level of expression of one or more genes of the first group of genes relative to a reference level selected from:

a level in a control sample or a pooled sample of control individuals; or an average level in a population of current and former smokers; or ii) administering to the subject one or more of:

intensive smoking cessation therapy and an inhaled short-acting β2 agonist; wherein the subject is determined not to have an increased level of expression of one or more genes of the first group of genes relative to a reference level selected from:

a level in a control sample or a pooled sample of control individuals; or an average level in a population of current and former smokers.

27. The method of claim 26, wherein the subject has a Global Initiative for Chronic Obstructive Lung Disease (GOLD) grade of 2 or lower and the method comprises administering to the subject:

an inhaled long acting antimuscarinic; an inhaled long-acting β2 agonist; and an inhaled corticosteroid;

wherein the subject is determined to have an increased level of expression of one or more genes of the first group of genes relative to the reference level.

28. The method of claim 26, further comprising determining the level of expression of at least one of:

Transcobalamin 1 (TCN1); Adenosylhomocysteinease like 2 (AHCYL2); N-acetylgalactosaminyltransferase 4 (GALNT4); major facilitator superfamily domain containing 4A (MFSD4); phospholipase A2 group IVA (PLA2G4A); tetraspanin 13 (TSPAN13); transmembrane 9 superfamily member 3 (TM9SF3); N-acetylgalactosaminyltransferase 5 (GALNT5); N-acetylgalactosaminyltransferase 7 (GALNT7); prostate androgen-regulated mucin-like protein 1 (PARM1); N-acetylgalactosaminyltransferase 12 (GALNT12); armadillo repeat containing X-linked 3 (ARMCX3); CEA cell adhesion molecule 5 (CEACAM5); retinol dehydrogenase 10 (RDH10); ectonucleoside triphosphate diphosphohydrolase 4 (ENTPD4); fucosyltransferase 6 (FUT6); parathyroid hormone like hormone (PTHLH); asparaginase and isoaspartyl peptidase 1 (ASRGL1); solute carrier family 26 member 2 (SLC26A2); cathepsin C (CTSC); leucine rich repeat containing 8 VRAC subunit A (LRRC8A); transmembrane protein 165 (TMEM165); pyridoxal dependent decarboxylase domain containing 1 (PDXDC1); glucosamine-phosphate N-acetyltransferase 1 (GNPNAT1); tetraspanin 8 (TSPAN8); solute carrier family 39 member 8 (SLC39A8); Magnesium transporter 1 (MAGT1); ATPase 13A5 (ATP13A5); claudin 10 (CLDN10); ectonucleoside triphosphate diphosphohydrolase 3 (ENTPD3); fer-1 like family member 6 (FERIL6); phospholipid phosphatase 5 (PLPP5 or PPAPDC1B); adaptor related protein complex 2 subunit beta 1 (AP2B1); S100 calcium binding protein A14 (S100A14); Sciellin (SCEL); UDP-galactose-4-epimerase (GALE); SEC31 homolog A, COPII coat complex component (SEC31A); alpha-2-glycoprotein 1, zinc-binding (AZGP1); nicotinamide nucleotide transhydrogenase (NNT); armadillo repeat containing X-linked 6 (ARMCX6); uroplakin 1B (UPK1B); MORC family CW-type zinc finger 4 (MORC4); serine protease 23 (PRSS23); solute carrier family 31 member 1 (SLC31A1); S100 calcium binding protein P (S100P); transmembrane serine protease 4 (TMPRSS4); frizzled class receptor 5 (FZD5); cAMP responsive element binding protein 3 like 1 (CREB3L1); family with sequence similarity 177 member B (FAM177B); 3-hydroxy-3-methylglutaryl-CoA synthase 2 (HMGCS2); mucin 2 (MUC2); selenoprotein I (SELENO1 or EPT1); solute carrier family 44 member 3 (SLC44A3); WD repeat domain 72 (WDR72); serine/threonine kinase 38 like (STK38L); 1 methylenetetrahydrofolate dehydrogenase (NADP+dependent) 2 (MTHFD2); V-set domain containing T cell activation inhibitor 1 (VTCN1); proline rich coiled-coil 1 (PRRC1); dispatched RND transporter family member 1 (DISP1); KDEL endoplasmic reticulum protein retention receptor 2 (KDELR2); SEC24 homolog A (SEC24A); potassium two pore domain channel subfamily K member 6 (KCNK6); diacylglycerol kinase alpha (DGKA); myosin 1C (MYO1C); ribophorin II (RPN2); ATPase H+ transporting V0 subunit el (ATP6VOE1); fucosyltransferase 2 (FUT2); acyl-CoA binding domain containing 3 (ACBD3); cytochrome P450 family 2 subfamily C member 18 (CYP2C18); beta-1,4-galactosyltransferase 4 (B4GALT4); Anoctamin 10 (ANO10); serine protease 8 (PRSS8); vasoactive intestinal peptide receptor 1 (VIPR1); major facilitator superfamily domain containing 1 (MFSD1); glucosamine (UDP-N-acetyl)-2-epimerase/N-acetylmannosamine kinase (GNE); tetraspanin 5 (TSPAN5); transmembrane protein 39A (TMEM39A); solute carrier family 1 member 5 (SLC1A5); fucosyltransferase 3 (FUT3); LOC100128816; an intron or splice variant of EF-hand calcium binding domain 4B (EFCAG4B); transmembrane protein 263 (TMEM263 or C12orf23); isocitrate dehydrogenase 1 (IDH1); transmembrane protein 167A (TMEM167A); adaptor related protein complex 4 subunit beta 1 (AP4B1); pyruvate dehydrogenase kinase 1 (PDK1); serine palmitoyltransferase small subunit A (SPTSSA); sphingomyelin phosphodiesterase acid like 3A (SMPDL3A); ADAM metallopeptidase domain 9 (ADAM9); solute carrier family 16 member 9 (SLC16A9); SEC61 translocon subunit alpha 1 (SEC61A1); acidic nuclear phosphoprotein 32 family member E (ANP32E); CEA cell adhesion molecule 6 (CEACAM6); transmembrane protein 211 (TMEM211); opsin 1, long wave sensitive (OPNILW); fibroblast growth factor binding protein 1 (FGFBP1); solute carrier family 12 member 8 (SLC12A8); serpin family B member 8 (SERPINB8); cortactin binding protein 2 (CTTNBP2); BCL2 like 15 (BCL2L15); UDP-N-acetylglucosaminyltransferase subunit (ALG14); FKBP prolyl isomerase 14 (FKBP14); Zinc finger 391 (ZNF391); DEAH-box helicase 15 (DHX15); tubulin alpha 1c (TUBA1C); MOB family member 4 (MOB4); piggyBac transposable element derived 2 (PGBD2); potassium two pore domain channel subfamily K member 1 (KCNK1); mal, T cell differentiation protein 2 (MAL2); protein disulfide isomerase family A member 5 (PDIA5); trophoblast glycoprotein (TPBG); glutamic—pyruvic transaminase 2 (GPT2); transmembrane p24 trafficking protein 3 (TMED3); TIMP metallopeptidase inhibitor 1 (TIMP1); calcium activated nucleotidase 1 (CANT1); and NIPA magnesium transporter 2 (NIPA2).

29. The method of claim 26, wherein:
step a) of the method further comprises determining the level of expression of one or more genes of a second group of genes, the second group of genes comprising:
kinesin family member 13A (KIF13A); TBC1 domain family member 22B (TBC1D22B); coiled-coil domain containing 69 (CCDC69); protein kinase C epsilon (PRKCE); Bardet-Biedl syndrome 1 (BBS1); family with sequence similarity 53 member B (FAM53B); spectrin repeat containing nuclear envelope family member 3 (SYNE3 or LINC00341); mastermind like transcriptional coactivator 2 (MAML2); SLIT-ROBO Rho GTPase activating protein 2 (SRGAP2); coiled-coil domain containing 170 (CCDC170); cyclin and CBS domain divalent metal cation transport mediator 2 (CNNM2); WW and C2 domain containing 1 (WWC1); Cluster of differentiation 38 (CD38); H2B.U histone 1 (H2BU1 or HIST3H2BB); potassium voltage-gated channel subfamily B member 1 (KCNB1); hes related family bHLH transcription factor with YRPW motif 2 (HEY2); pericentrin (PCNT); junctional cadherin complex regulator (JHY or C11orf63); GRB2 associated binding protein 2 (GAB2); kinesin family member 24 (KIF24); zinc finger protein 709 (ZNF709); cytochrome P450 family 27 subfamily A member 1 (CYP27A1); forkhead associated phosphopeptide binding domain 1 (FHAD1); suppressor of cancer cell invasion (SCAI); BRF1 RNA polymerase III transcription initiation factor subunit (BRF1); zinc finger protein 382 (ZNF382); zinc finger protein 473 (ZNF473); zinc finger protein 544 (ZNF544); SNF related kinase (SNRK); centrosomal protein 250 (CEP250); ubiquitin specific peptidase 2 (USP2); syntaxin binding protein 1 (STXBP1); enolase 4 (ENO4); retrotransposon Gag like 5 (RTL5 or RGAG4); sperm tail PG-rich repeat containing 1 (STPG1); interleukin 5 receptor subunit alpha (IL5RA)' unc-51 like autophagy activating kinase 2 (ULK2); zinc finger and BTB domain containing 44 (ZBTB44); NOP2/Sun RNA methyltransferase family member 7 (NSUN7); potassium inwardly rectifying channel subfamily J member 2 (KCNJ2); NIMA related kinase 4 (NEK4); centrosomal protein 104 (CEP104); outer dynein arm docking complex subunit 3 (ODAD3 or CCDC151); laminin subunit gamma 2 (LAMC2); NIMA related kinase 11

(NEK11); Zinc finger protein 82 (ZFP82); enhancer of zeste 1 (EZH1); proprotein convertase subtilisin/kexin type 6 (PCSK6); serine protease 12 (PRSS12); pygopus family PHD finger 1 (PYGO1); and FXYD domain containing ion transport regulator 6 (FXYD6); and step b) of the method further comprises
- i) administering to the subject one or more of:
- an inhaled long acting antimuscarinic; an inhaled long-acting β2 agonist; and an inhaled corticosteroid;
- wherein the subject is determined to have an increased level of expression of one or more genes of the first group of genes or a decreased level of expression of one or more genes of the second group of genes relative to a reference level selected from:
  - a level in a control sample or a pooled sample of control individuals; or
  - an average level in a population of current and former smokers; or
- ii) administering to the subject one or more of:
- intensive smoking cessation therapy and an inhaled short-acting β2 agonist; wherein the subject is determined not to have an increased level of expression of one or more genes of the first group of genes or a decreased level of expression of one or more genes of the second group of genes relative to a reference level selected from:
  - a level in a control sample or a pooled sample of control individuals; or
  - an average level in a population of current and former smokers.

\* \* \* \* \*